(12) United States Patent
Wrigg

(10) Patent No.: US 10,441,847 B2
(45) Date of Patent: Oct. 15, 2019

(54) FRAMEWORK, DEVICES, AND METHODOLOGIES CONFIGURED TO ENABLE GAMIFICATION VIA SENSOR-BASED MONITORING OF PHYSICALLY PERFORMED SKILLS, INCLUDING LOCATION-SPECIFIC GAMIFICATION

(71) Applicant: GN IP PTY LTD, Sydney, New South Wales (AU)

(72) Inventor: Darren Wrigg, Sydney (AU)

(73) Assignee: RLT IP Ltd, Gosport (GB)

( * ) Notice: Subject to any disclaimer, the term of this patent is extended or adjusted under 35 U.S.C. 154(b) by 0 days.

(21) Appl. No.: 15/577,001

(22) PCT Filed: May 27, 2016

(86) PCT No.: PCT/AU2016/050415
§ 371 (c)(1),
(2) Date: Nov. 27, 2017

(87) PCT Pub. No.: WO2016/187673
PCT Pub. Date: Dec. 1, 2016

(65) Prior Publication Data
US 2018/0161624 A1 Jun. 14, 2018

(30) Foreign Application Priority Data

May 27, 2015 (AU) .................................. 2015901945
Feb. 2, 2016 (WO) ................. PCT/AU2016/000020

(51) Int. Cl.
*A63B 24/00* (2006.01)
*G09B 5/12* (2006.01)
(Continued)

(52) U.S. Cl.
CPC ...... *A63B 24/0006* (2013.01); *G06F 19/3481* (2013.01); *G09B 5/125* (2013.01);
(Continued)

(58) Field of Classification Search
None
See application file for complete search history.

(56) References Cited

U.S. PATENT DOCUMENTS 7,825,815 B2  11/2010  Shears et al.
2010/0053867 A1  3/2010  Ellis et al.
(Continued)

OTHER PUBLICATIONS

International Search Report and Written Opinion dated Jul. 11, 2016 from International Application No. PCT/AU2016/050415 filed May 27, 2016, 13 pages.
(Continued)

*Primary Examiner* — Ronald Laneau

(57) ABSTRACT

The application relates to technological frameworks whereby user skill performances are monitored using Performance Sensor Units (PSUs), and data derived from those PSUs is processed thereby to determine attributes of the user skill performances. For example, the identification of attributes of performances is used to drive computer processes, such as computer processes described herein. Particular focus is given to technologies which enable the gamification of skills via delivery of competitive challenges, such challenges being driven by data derived from PSUs that monitor physical performances. For example, in one embodiment users compete in the context of performing a particular skill or skills "better" than others (for example in the context of amplitude, power, accuracy, successive completions, and so on).

25 Claims, 34 Drawing Sheets

(51) Int. Cl.
  *G09B 19/00* (2006.01)
  *G06F 19/00* (2018.01)
  *H04W 4/021* (2018.01)
  *A63B 60/46* (2015.01)

(52) U.S. Cl.
  CPC .......... *G09B 19/003* (2013.01); *H04W 4/021* (2013.01); *A63B 60/46* (2015.10)

(56) References Cited

U.S. PATENT DOCUMENTS

| | | |
|---|---|---|
| 2013/0203475 A1 | 8/2013 | Kil et al. |
| 2014/0142459 A1 | 5/2014 | Jayalth et al. |
| 2014/0235230 A1* | 8/2014 | Raleigh ............ G06Q 10/06375 455/419 |
| 2014/0320481 A1* | 10/2014 | Odio Vivi ............. G06F 1/1694 345/214 |
| 2017/0061817 A1* | 3/2017 | Mettler May ........ G09B 19/003 |

OTHER PUBLICATIONS

Extended European Search Report dated Jan. 21, 2019 from European Application No. 16798963.1, 7 pages.
First Office Action dated Apr. 15, 2019, Chinese Patent Application No. 201680044207.6, 15 pages.

* cited by examiner

FRAMEWORK, DEVICES, AND METHODOLOGIES CONFIGURED TO ENABLE GAMIFICATION VIA SENSOR-BASED MONITORING OF PHYSICALLY PERFORMED SKILLS, INCLUDING LOCATION-SPECIFIC GAMIFICATION

CROSS-REFERENCE TO RELATED APPLICATIONS

The present application is a § 371 application of International Application No. PCT/AU2016/050415 filed on May 27, 2016 and titled "FRAMEWORK, DEVICES, AND METHODOLOGIES CONFIGURED TO ENABLE GAMIFICATION VIA SENSOR-BASED MONITORING OF PHYSICALLY PERFORMED SKILLS, INCLUDING LOCATION-SPECIFIC GAMIFICATION," which claims the benefit of Australian Patent Application No. 2015901945 filed on May 27, 2015 and International Application No. PCT/AU2016/000020 filed on Feb. 2, 2016. International Application No. PCT/AU2016/050415, Australian Patent Application No. 2015901945, and International Application No. PCT/AU2016/000020 are incorporated herein.

FIELD OF THE INVENTION

The present invention relates to frameworks, devices and methodologies configured to enable gamification via sensor-based monitoring of physically performed skills, including location-specific gamification. Embodiments of the invention include software and hardware, and associated methodologies, associated with the generation, distribution, and execution of gamified content. A particular focus of the technology described herein is to enable users to define and/or participate in competitive activities which are assessed based on analysis of a plurality of users' respective performances of defined motion-based skills.

BACKGROUND

Any discussion of the background art throughout the specification should in no way be considered as an admission that such art is widely known or forms part of common general knowledge in the field.

Recent years have seen a rise in popularity of competitive activities which are assessed based on tracking technology. For example, cyclists have popularly adopted a range of technologies that enable the tracking of particular rides (for example with start and end points defined via GPS coordinates) thereby to enable a form of timed racing which involves very little in the way of organisational overheads. For example, often all a rider need do in order to compete is complete a specified ride at any convenient time, whilst carrying a GPS-enabled device (often a smartphone) which executes compatible tracking software.

SUMMARY OF THE INVENTION

It is an object of the present invention, at least in some embodiments to overcome or ameliorate at least one of the disadvantages of the prior art, or to provide a useful alternative.

The follow set of summary embodiments are provided to foreshadow potential patent claims based on a selection of technological aspects disclosed in the following Detailed Description. These are not intended to be limiting in any way on the scope of claims that might be pursued.

One embodiment provides a method for enabling a user of end-user hardware including one or more Motion Sensor Units (MSUs) to participate in a competitive activity, the method including:

maintaining, at a server device, a plurality of challenge data sets, wherein each challenge data set is representative of a challenge activity that is configured to be attempted by a user of end-user hardware including one or more MSUs, wherein each challenge data set includes data representative of:

(i) one or more challenge skills, wherein each of the one or more challenge skills is associated with skill-specific configuration data, wherein the skill-specific configuration data is downloadable to the end user hardware thereby to configure the end user hardware to enable identification and analysis of performance events of the challenge skill based on Motion Sensor Data (MSD) derived from the one or more of MSUs; and (ii) data representative of one or more competitive parameters;

enabling a user of the end-user hardware including one or more MSUs to participate in a given challenge activity, wherein enabling the user to participate in the given challenge activity includes:

(i) causing the user's end-user hardware to apply the skill-specific configuration data for the one or more challenge skills; and (ii) causing analysis of data derived from the one or more MSUs, based on the applied skill-specific configuration data, thereby to enable assessment relative to the one or more competitive parameters.

One embodiment provides a method for operating user of end-user hardware including one or more Motion Sensor Units (MSUs), the method including:

identifying a challenge data sets, wherein the challenge data set is representative of a challenge activity that is configured to be attempted by a user of end-user hardware including one or more MSUs, wherein each challenge data set includes data representative of:

(i) one or more challenge skills, wherein each of the one or more challenge skills is associated with skill-specific configuration data, wherein the skill-specific configuration data is downloadable to the end user hardware thereby to configure the end user hardware to enable identification and analysis of performance events of the challenge skill based on Motion Sensor Data (MSD) derived from the one or more of MSUs; and (ii) data representative of one or more competitive parameters;

enabling a user of the end-user hardware including one or more MSUs to participate in a given challenge activity, wherein enabling the user to participate in the given challenge activity includes:

(i) causing the user's end-user hardware to apply the skill-specific configuration data for the one or more challenge skills; and (ii) causing analysis of data derived from the one or more MSUs, based on the applied skill-specific configuration data, thereby to enable assessment relative to the one or more competitive parameters.

One embodiment provides a method for providing a multi-user competitive activity, the method including:

providing an authoring interface that is configured to enable an activity-author user to define a challenge data set for a competitive activity, wherein each challenge data set includes:

(i) data representative of location information for a challenge location;

(ii) data representative of one or more challenge skills, wherein each of the one or more challenge skills are selected from a repository of challenge skills that are configured to be identified via end-user worn motion sensor units; and (iii) data representative of one or more competitive parameters;

making the competitive activity available to a plurality of activity-participant users, wherein a given activity-participant participates in the competitive activity based on analysis of data derived from a motion-sensing garment associated with the user.

One embodiment provides a method for providing a multi-user competitive activity, the method including:

identifying location information associated with an activity-participant user;

identifying one or more predefined competitive activities associated with the location information, wherein each competitive activity is associated with a respective challenge data set, wherein each challenge data set includes:

(i) data representative of location information for a challenge location;

(ii) data representative of one or more challenge skills, wherein each of the one or more challenge skills are selected from a repository of challenge skills that are configured to be identified via end-user worn motion sensor units; and (iii) data representative of one or more competitive parameters;

processing data derived from a set of worn motion sensor units associated with the activity-participant user thereby to determine, for a given one of the identified predefined competitive activities, assess the activity-participant user relative to the one or more competitive parameters.

One embodiment provides a computer program product for performing a method as described herein.

One embodiment provides a non-transitory carrier medium for carrying computer executable code that, when executed on a processor, causes the processor to perform a method as described herein.

One embodiment provides a system configured for performing a method as described herein.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

The contents of PCT/AU2016/000020 is hereby incorporated by cross reference in its entirety.

BRIEF DESCRIPTION OF THE DRAWINGS

Embodiments of the invention will now be described, by way of example only, with reference to the accompanying drawings in which.

DETAILED DESCRIPTION

Figure 1A:
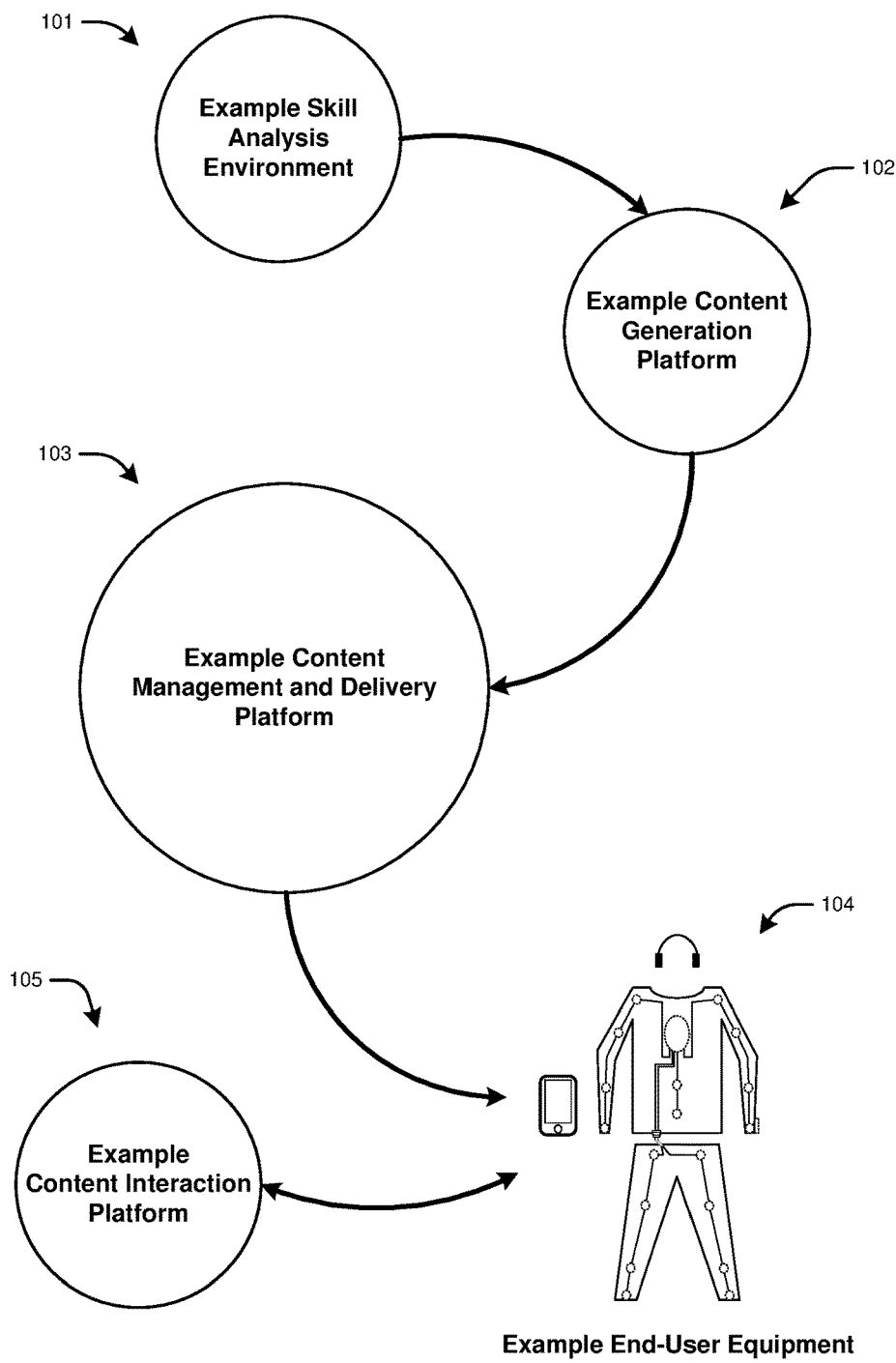
FIG. 1A schematically illustrates a framework configured to enable generation and delivery of content according to one embodiment.

Embodiments described herein relate to technological frameworks whereby user skill performances are monitored using Performance Sensor Units (PSUs), and data derived from those PSUs is processed thereby to determine attributes of the user skill performances. For example, the identification of attributes of performances is used to drive computer processes, such as computer processes described herein. Particular focus is given to technologies which enable the gamification of skills via delivery of competitive challenges, such challenges being driven by data derived from PSUs that monitor physical performances. For example, in one embodiment users compete in the context of performing a particular skill or skills "better" than others (for example in the context of amplitude, power, accuracy, successive completions, and so on).

Technology described herein is related to technology described in PCT/AU2016/000020, which is incorporated by cross reference in its entirety, and provided useful content and additional detail relating to supporting technological aspects. More specifically, technological frameworks described herein make use of PSUs to collect data representative of performance attributes, and utilise that data for downstream processing purposes. These purposes may include skills training purposes (described in detail PCT/AU2016/000020) and other purposes. A purpose specifically considered here is skill-based gamification, including location-specific gamification. In essence, this includes enabling users to participate in games/challenges that are scored (or otherwise assessed) based on analysis of performance-based skills via motion-sensor derived data.

The nature of the skill performances varies between embodiments, and the following two general categories are used for the purpose of examples considered herein:

Human motion-based skill performances. These are performances where human motion attributes are representative of defining characteristics of a skill. For example, motion-based performances include substantially any physical skill which involves movement of the performer's body. A significant class of motion-based performances are performances of skills that are used in sporting activities.

Audio-based skill performances. These are performances where audibly-perceptible attributes are representative of defining characteristics of a skill. For example, audio-based skill performances include musical and/or linguistic performances. A significant class of audio-based performances are performances of skills associated with playing musical instruments.

Although the examples provided below focus primarily on the comparatively more technologically challenging case of motion-based skills performances, it will be appreciated that principles applied in respect of motion-based skills are readily applied in other situations. For example, the concept of using Observable Data Conditions (ODCs) in data received from PSUs is applicable equally between motion, audio, and other forms of performances.

Terminology

For the purpose of embodiments described below, the following terms are used:

Performance Sensor Unit (PSU). A performance sensor unit is a hardware device that is configured to generate data in response to monitoring of a physical performance. Examples of sensor units configured to process motion data and audio data are primarily considered herein, although it should be appreciated that those are by no means limiting examples.

Performance Sensor Data (PSD). Data delivered by a PSU is referred to as Performance Sensor Data. This data may comprise full raw data from a PSU, or a subset of that data (for example based on compression, reduced monitoring, sampling rates, and so on).

Audio Sensor Unit (ASU). An audio sensor unit is a category of PSU, being a hardware device that is configured to generate and transmit data in response to monitoring of sound. In some embodiments an ASU is configured to monitor sound and/or vibration effects, and translate those into a digital signal (for example a MIDI signal). One example is an ASU is a pickup device including a transducer configured to capture mechanical vibrations in a stringed instrument and concert those into electrical signals.

Audio Sensor Data (ASD). This is data delivered by one or more ASUs.

Motion Sensor Unit (MSU). A motion sensor unit is a category of PSU, being a hardware device that is configured to generate and transmit data in response to motion. This data is in most cases defined relative to a local frame of reference. A given MSU may include one or more accelerometers; data derived from one or more magnetometers; and data derived from one or more gyroscopes. A preferred embodiment makes use of one or more 3-axis accelerometers, one 3-axis magnetometer, and one 3-axis gyroscope. A motion sensor unit may be "worn" or "wearable", which means that it is configured to be mounted to a human body in a fixed position (for example via a garment).

Motion Sensor Data (MSD). Data delivered by a MSU is referred to as Motion Sensor Data (MSD). This data may comprise full raw data from a MSU, or a subset of that data (for example based on compression, reduced monitoring, sampling rates, and so on).

MSU-enabled garment. A MSU enabled garment is a garment (such as a shirt or pants) that is configured to carry a plurality of MSUs. In some embodiments, the MSUs are mountable in defined mountain zones formed in the garment (preferably in a removable manner, such that individual MSUs are able to be removed and replaced), and coupled to communication lines.

POD Device. A POD device is a processing device that receives PSD (for example MSD from MSUs). In some embodiments it is carried by a MSU-enabled garment, and in other embodiments it is a separate device (for example in one embodiment the POD device is a processing device that couples to a smartphone, and in some embodiments POD device functionality is provided by a smartphone or mobile device). The MSD is received in some cases via wired connections, in some cases via wireless connections, and in some cases via a combination of wireless and wired connections. As described herein, a POD device is responsible for processing the MSD thereby to identify data conditions in the MSD (for example to enable identification of the presence of one or more symptoms). In some embodiments the role of a POD device is performed in whole or in part by a multi-purpose end-user hardware device, such as a smartphone. In some embodiments at least a portion of PSD processing is performed by a cloud-based service.

Motion Capture Data (MCD). Motion capture data (MCD) is data derived from using any available motion capture technique. In this regard, "motion capture" refers to a technique whereby capture devices are used to capture data representative of motion, for example using visual markers mounted to a subject at known locations. An example is motion capture technology provided by Vicon (although no affiliation between the inventors/applicant and Vicon is to be inferred). As discussed further below, MCD is preferably used to provide a link between visual observation and MSD observation.

Skill. In the context of a motion-based activity, a skill is an individual motion (or set of linked motions) that is to be observed (visually and/or via MSD), for example in the context of coaching. A skill may be, for example, a rowing motion, a particular category of soccer kick, a particular category of golf swing, a particular acrobatic manoeuvre, and so on. Reference is also made to "sub-skills". This is primarily to differentiate between a skill being trained, and lesser skills that form part of that skill, or are building blocks for that skill. For example, in the context of a skill in the form of juggling, a sub-skill is a skill that involves throwing a ball and catching it in the same hand.

Symptom. A symptom is an attribute of a skill that is able to be observed (for example observed visually in the context of initial skill analysis, and observed via processing of MSD in the context of an end-user environment). In practical terms, a symptom is an observable motion attribute of a skill, which is associated with a meaning. For example, identification of a symptom may trigger action in delivery of an automated coaching process. A symptom may be observable visually (relevant in the context of traditional coaching) or via PSD (relevant in the context of delivery of automated adaptive skills training as discussed herein).

Cause. Symptoms are, at least in some cases, associated with one causes (for example a given symptom may be associated with one or more causes). A cause is also in some cases able to be observed in MSD, however that is not necessarily essential. From a coaching perspective, one approach is to first identify a symptom, and then determine/predict a cause for that symptom (for example determination may be via analysis of MSD, and prediction may be by means other than analysis of MSD). Then, the determined/predicted cause may be addressed by coaching feedback, followed by subsequent performance assessment thereby to determine whether the coaching feedback was successful in addressing the symptom.

Observable Data Condition (ODC). The term Observable Data Condition is used to describe conditions that are able to be observed in PSD, such as MSD (typically based on monitoring for the presence of an ODC, or set of anticipated ODCs) thereby to trigger downstream functionalities. For example, an ODC may be defined for a given symptom (or cause); if that ODC is identified in MSD for a given performance, then a determination is made that the relevant symptom (or cause) is present in that performance. This then triggers events in a training program.

Training Program. The term "training program" is used to describe an interactive process delivered via the execution of software instructions, which provides an end user with instructions of how to perform, and feedback in relation to how to modify, improve, or otherwise adjust their performance. In at least some embodiments described below, the training program is an "adaptive training program", being a training program that executes on the basis of rules/logic that enable the ordering of processes, selection of feedback, and/or other attributes of training to adapt based on analysis of the relevant end user (for example analysis of their performance and/or analysis of personal attributes such as mental and/or physical attributes).

As described in more detail below, from an end-user product perspective some embodiments employ a technique whereby a POD device is configured to analyse a user's PSD (such as MSD) in respect of a given performance thereby to identify a particular skill that is performed, and in some cases also symptoms associated with that performance of the particular skill.

Example End-to-End Framework

FIG. 1A provides a high-level overview of an end-to-end framework which is leveraged by a range of embodiments described herein. In the context of FIG. 1A, an example skill analysis environment 101 is utilised thereby to analyse one or more skills, and provide data that enables the generation of end user content in relation to those skills. For instance, this in some embodiments includes analysing a skill thereby to determine ODCs that are able to be identified by PSUs (preferably ODCs that are associated with particular skills, skill symptoms, and the like). These ODCs are able to be utilised within content generation logic implemented by an example content generation platform 102 (such as a training program). In that regard, generating content preferably includes defining a protocol whereby prescribed actions are taken in response to identification of specific ODCs. In embodiments described below, content generation platform 102 is used to generate rules for one or more computing programs, thereby to enable those programs to identify that particular skills have been performed based on PSD (and in some cases symptoms associated with those skill performances).

One or more skill analysis environments and content generation platforms are utilised thereby to provide content to an example content management and delivery platform 103. This platform is in some embodiments defined by a plurality of networked server devices. In essence, the purpose of platform 103 is to make available content generated by content generation platforms to end users. In the context of FIG. 1A, that includes enabling download of content to example end-user equipment 104. The downloading in some embodiments includes an initial download of content, and subsequently further downloads of additional required content. The nature of the further downloads is in some cases affected by user interactions (for instance based on an adaptive progression between components of a skills training program and/or user selections). A particular example of downloaded content considered herein is content configured to identify that particular skills have been performed based on PSD (and in some cases symptoms associated with those skill performances).

Example equipment 104 is illustrated in the form of a MSU-enabled garment that carries a plurality of MSUs and a POD device, in conjunction with user interface devices (such as a smartphone, a headset, HUD eyewear, retinal projection devices, and so on).

In the example of FIG. 1A, a user downloads content from platform 103, and causes that content to be executed via equipment 104. For instance, this may include content that enables monitoring for the performance of particular skills based on PSD (for example skills relevant to a particular form of physical activity, such as snowboarding). In some embodiments, this is provided in conjunction the example of FIG. 1A, equipment 104 is configured to interact one or more content interaction platforms, including a media management platform 105. This is in come embodiments an external (web-based and/or provided via local computing hardware) platform that provides additional functionality relevant to the management of media content, and in particular provides functionality relating to correlation of media data (for example video data) with skill performances identified via PSD generated via one or more instances of hardware 104.

It should be appreciated that FIG. 1A depicts multiple phases of technology delivery, including a skill analysis phase (implemented thereby to analyse a skill that is to be identified and symptom-measured via end-user hardware), a content generation and distribution (which embeds data processing techniques from the skill analysis phase into software products and content for experiencing by end-users) and an end-user deliver phase (where end-user hardware is operated to enable analysis of physical performances, thereby to identify skills and symptoms). Media management functionalities primarily occur as part of the end-user delivery phase.

Gamification Via Challenges and Competitive Activities—Overview

As noted further above, a focus of the present application is gamification of motion-based skills. For example, this allows users of end-user hardware including MSUs (or other forms of PSU) to participate in challenges and the like, which are assessed based on MSD-derived skill performance assessment. Technologies disclosed herein relate to the provision of multi-user competitive activities. This in some embodiments includes tools, for example authoring interfaces, which enable the user-driven generation of competitive activities, and in some platforms includes platforms which make such competitive activities available to distributed users.

In overview, the competitive activities disclosed herein are based upon monitoring of human performances. In the examples considered below, these are performances monitored by way of motion sensing hardware, such MSU-enabled garments. This enables suitably configured processing devices to determine, based on input derived from the motion sensor units, attributes of motion-based performances. By way of example, this includes the like of determining particular skills that are performed, and attributes (e.g. symptoms) of those skills. The attributes may optionally relates to performance factors such as, for instance, power, speed, accuracy, height, and so on.

In some embodiments described below, there is a focus on competitive activates that are location-specific. That is, a particular competitive activity is associated with a specific location. A practical example is that of a skate park; challenges such as a "highest air", "most consecutive successful kickflips" and the like may be defined for a specific park. This allows users of that park to compete with one another, although without the need to attend the facility at a common time, or even know one another at a personal level. Rather, when at the relevant skate park, a user is able to identify challenges that have been defined (for example by other users), and compete via hardware-based monitoring of his/her own physical performances.

One embodiment provides a method for enabling a user of end-user hardware including one or more Motion Sensor Units (MSUs), such as a MSU-enabled garment) to participate in a competitive activity. The method includes maintaining, at a server device, a plurality of "challenge data sets". A challenge data set is a set of data defining a particular "challenge", which is used as a generic term to describe a competitive activity. Each challenge data set is representative of a challenge activity that is configured to be attempted by a user of end-user hardware including one or more MSUs. For example, the challenge includes performing one or more skills in a particular way to meet a defined objective.

Each challenge data set includes data representative of: (i) one or more challenge skills; and (ii) data representative of one or more competitive parameters. In overview, the challenge skills are predefined skills that form part of a challenge (i.e. skills that are to be performed), and the competitive parameters define how users are assessed (for example whether the objective is to perform a given skill multiple times, perform a given skill with a particular attribute maximised, and so on).

Each of the one or more challenge skills is associated with skill-specific configuration data. This skill-specific configuration data is downloadable to the end user hardware thereby to configure the end user hardware to enable identification and analysis of performance events of the challenge skill based on Motion Sensor Data (MSD) derived from the one or more of MSUs. As discussed in more detail further below, the skill-specific configuration data preferably includes sensor configuration data (which configures MSUs to collect MSD in a defined manner) and state engine data (which enables processing of MSD thereby to identify skill performances and determine symptoms/attributes).

The method then includes enabling a user of the end-user hardware including one or more MSUs to participate in a given challenge activity. Enabling the user to participate in a given challenge activity includes: (i) causing the user's end-user hardware to apply the skill-specific configuration data for the one or more challenge skills; and (ii) causing analysis of data derived from the one or more MSUs, based on the applied skill-specific configuration data, thereby to enable assessment relative to the one or more competitive parameters.

Some embodiments include providing an authoring interface that is configured to enable an activity-author user to define a challenge data set for a competitive activity. In this way, challenge content is defined by users, enabling user-driven coordination of multi-user competitive activities.

Figure 1B:
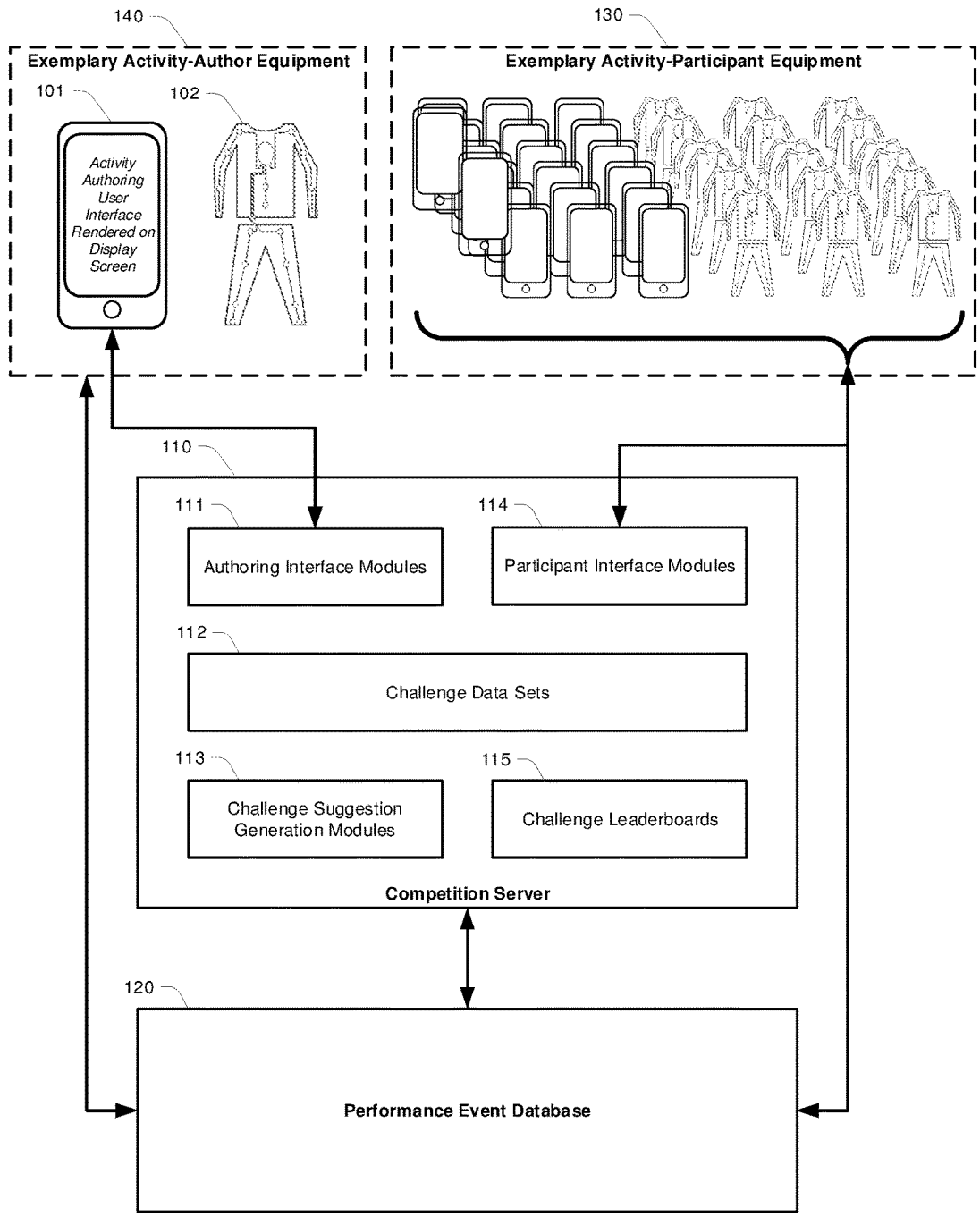
FIG. 1B schematically illustrates a framework configured to enable generation and delivery of challenge content according to a further embodiment.

An exemplary framework is illustrated in FIG. 1B. Box 140 represents exemplary activity author equipment, including a client device 101 and a motion sensor enable garment 102.

Client device 101 is configured to render an activity-authoring user interface, for example via a proprietary app or via a web browser application. Although client device 101 is illustrated as a mobile device, various forms of client devices are used across implementations, including the likes of smartphones, tablets, notebook/laptop PCs, desktop PCs, gaming consoles, and so on. Client device 101 is also, in this embodiment, configured to communicate with sensor enabled garment 102. Exemplary hardware and technology relating to sensor enabled garment 102 is described further below.

Box 130 represents exemplary activity-participant users' equipment, which also includes client devices and MSU-enabled garments. These users make use of their respective client devices to view available activities, and review their results of participation in those activities. The participation is enabled by utilisation of the sensor enabled garments, which enable performance analysis (either by on-board processing capabilities as described below, or by alternate means).

As described in more detail further below, activity-author users and activity participant users, via their respective equipment, interact with a competition server 110, which enables activities authored by a given user (acting as an activity-author user) to become available for participation by other users (acting as activity-participant users).

In the illustrated embodiment, client device 101 interacts (directly or indirectly) with authoring interface modules 111 of server 110. These authoring interface modules enable interaction between server 100 and an activity authoring user interface displayed by device 101. The authoring process includes:

A user, referred to as an "activity-author user" is able to author a competitive activity. This is a process which includes interacting with an interface, for example by way of a user interface rendered on a client terminal either via a web browser or a proprietary app, thereby to define a challenge data set for a competitive activity. A challenge data set includes:

(i) Data representative of location information for a challenge location. For example, this may be defined by reference to GPS coordinates (or another coordinate system), or by reference to a location marker (for example an RFID tag, BLE tag, 2D barcode, or the like, which is able to be read by a client device at the challenge location).

(ii) Data representative of one or more challenge skills. These are skills, which are able to be observed and identified using hardware which processes data derived from a user's worn motion sensor units. In the context of authoring, each of the one or more challenge skills are selected from a repository of challenge skills that are configured to be identified via end-user worn motion sensor units. This may, in some embodiments, include user-defined skills that are created subject to a skill recording process, described further below.

(iii) Data representative of one or more competitive parameters. These define how user participation attempts are judged relative to one another.

For a given challenge data set, the one or more competitive parameters define how a first participation in the competitive activity is judged against a second participation in the competitive activity. For example, in some embodiments the one or more competitive parameters include a count of how many times a particular skill is performed in succession (such as a challenge to perform Skill A successfully, or with certain defined attributes, the most times consecutively, or the most times in a minute). In some embodiments the one or more competitive parameters include a count of how many times a particular skill is performed relative to defined timing parameters (for example a challenge to perform Skill A on Y occasions as fast as possible). In some embodiments the one or more competitive parameters include a count of how many unique skills are performed in succession (for example a challenge for a skateboarder to perform multiple different tricks successfully in succession, in some cases being a defined set of different tricks in which case the one or more competitive parameters may include a time period to perform a defined set of skills). In some embodiments the one or more competitive parameters include a count of how many unique skills are performed relative to defined timing parameters (for example most different tricks in one minute). In some embodiments the one or more competitive parameters include a value derived from one or more performance attributes for a given skill performance event. These attributes may be defined based on one or more of: performance of the skill relative to defined optimal performance; one or more motion-based attributes observed in the performance of the skill; a skill performance height attribute; a skill performance distance attribute; a skill performance power attribute; a skill performance speed attribute; a skill performance duration attribute; and various other factors (which may be specific to certain skills).

Challenge suggestion modules 113 are configured to assist in operation of the authoring interface by providing, to an author user, suggestions of skills and/or competitive parameters. This, in preferred embodiments, includes accessing data representative of skill performance events associated with the challenge location (which, in the illustrated embodiments, is available in a performance event database 120 which maintains historical data representative of user skill performance events, derived in some embodiments from skills training, and in some embodiments from users engaging in competitive activities). For example, modules 113 may determine that, for a Location A, a common skill performed is Skill B, .and hence Skill B is suggested. Then, based on data stored in relation to Skill B, suggestions are made in relation to competitive parameters for Skill B, for example: consecutive performances, speed, height, power distance, and so on. For example, such data may be derived from attributes that are monitored (or able to be monitored) for the relevant skill.

In some embodiments suggestion modules are responsive to skill performance data associated with the activity-author user, such that the author is assisted in defining a challenge data set corresponding to an activity completed by the activity-author user. For example, based on analysis of performance event data 120, modules 113 identify that User A has previously successfully performed Skill B on C consecutive occasions at Location D. Therefore, a suggestion is provided to define a challenge data set for performing Skill C consecutively at Location D. In some cases modules 113 perform additional analysis to assist the activity-author user to define a challenge data set corresponding to an activity (i) completed by the activity-author user; and (ii) for which the activity-author user is a current competition leader. For instance, continuing with the previous example, modules 113 analyse data 120 to determine whether another user has performed Skill B at Location D on more than C consecutive occasions. It will be appreciated that a user often has a desire to define challenges in respect of which they are a current challenge leader. In further embodiments, an activity-author user generates competitive activities as a non-competitor, for example on behalf of a venue manager or the like.

In some embodiments the authoring interface is available in a local mode, whereby the interface is presented on a local user interface device, and the interface accesses skill performance data associated with the activity-author user from a local storage repository. However, it will be appreciated that a more functional arrangement is for the authoring interface to be provided in an online mode, whereby the authoring interface accesses skill performance data associated with the activity-author user from a central storage repository such as database 120. The latter approach allows for accessing of a wider range of centrally accessible data to assist with authoring.

In some embodiments, the authoring process makes use of a recording functionality, whereby a user is in essence enabled to record a particular performance, and define a challenge accordingly. This, in some embodiments, includes recording a wide range of sensor data, and uploading that for processing at a server device that has access to a range of processing techniques that are not locally available at a POD device (for example to enable identification of a wider range of skills). Such a recording functionality may be used to define custom skills, based on the user's actual performance (for example defining custom tricks, specialist yoga poses, location-specific rock climbing moves, and so on). In some embodiments the authoring interface provides a model (for example a kinetic, kinematic, skelematic, or other model) to enable a user in visualising what has been recorded.

In some embodiments server 11O executes an automated process thereby to define, without user input, one or more competitive activities for a given location based on performances identified at that location. That is, challenge data sets may be computer- authored using the suggestion modules.

Once an activity-author user has defined a challenge data set for a given competitive activity, that. challenge data set is loaded into data repository 112. Each challenge data set is associated with various additional aspects of data beyond those specifically authored by a user, for example references to data that is to be loaded onto a POD device thereby to enable monitoring for skills (and/or skill attributes) relevant to a particular competitive activity, and a reference to a table in a challenge leaderboard 115 which stores results of attempts at competitive activities by various users, including top results.

Participant interface modules 114 enable user to participate in competitive activities defined in data 112. For example, a user selects one or more challenges in which they wish to compete (either upon arriving at a location, based on a database query, or via other means), and causes a download of challenge data to either or both of the POD device and the user's client device. For example, in one embodiment the user utilises the client device as a user interface to navigate available challenges, and then causes data required for that challenge to be downloaded to the POD device (this may leverage a network connection provided by the mobile device).

In some embodiments there is a need to download additional state engine data thereby to enable monitoring for specific skills and/or skill attributes. In some embodiments there is a defined set of activity-specific state engine data configured to enable monitoring of a given activity type, which includes a plurality of skills. For example, this may be a "skateboarding monitoring pack", which enables the user's POD device to identify a set of skateboarding skills (for example specific tricks) and attributes of those tricks (e.g. identifying that a user has successfully performed a "kick-flip" maneuver, and a height measurement for that kickflip maneuver).

In some embodiments making the competitive activity available to a given activity-participant user includes configuring a device local to the activity-participant user to monitor performance of the challenge skills relative to the competitive parameters in an offline mode. This may include (i) determining a location for an activity participant user; and (ii) displaying to the user-activity user data representative of one or more predefined competitive activities associated with the determined location. The user is then enabled to select one or more competitive activities, and cause a download to their POD device of relevant state engine data required to enable monitoring for the relevant skills and/or skill attributes.

The terms "competitive activity" and "challenge" are used generally interchangeably herein. That is, the term "challenge" is used to describe a competitive activity. However, the terms "competitive activity" is used to indicate that the scope of activities able to be provided by various embodiments might extend beyond activities that are conventionally associated with the term "challenge".

Skill Analysis Phase—Overview

As noted above, a skill analysis phase is implemented thereby to analyse a skill that is to be identified and analysed in an end-user delivery phase (for example in the context of challenge participation). That is, there is a preliminary phase whereby a skill is examined, thereby to determine how it is to be automatically identified and analysed via PSD (such as MSD). The outcomes of this phase are used to enable configuration of end-user hardware (for example MSU-enabled garments and associated processing infrastructure) and/or server-side processing infrastructure that is configured to receive raw and/or partially processed data derived from end-user hardware MSUs.

In some embodiments, the skill analysis phase preferably includes analysis to: (i) determine attributes of a skill, for example attributes that are representative of the skill being performed (which is particularly relevant where the end user functionality includes skill identification), and attributes that are representative of the manner in which a skill is performed, such as symptoms and causes (which are particularly relevant where end user functionality includes skill performance analysis, for instance in the context of delivery of skills training); and (ii) define ODCs that enable automated identification of skill attributes (such as the skill being performed, and attributes of the performance of that skill such as symptoms and/or causes) such that end user hardware (PSUs, such as MSUs) is able to be configured for automated skill performance analysis.

The nature of the skill analysis phase varies significantly depending on the nature of a given skill (for example between the categories of motion-based skills and audio-based skills). For the sake of example, exemplary embodiments are now described in relation to a skill analysis phase in the context of a motion-based skill. That is, embodiments are described by reference to analysing a physical activity, thereby to determine ODCs that are used to configure a POD device that monitors data from body-mounted MSUs. This example is selected to be representative of a skill analysis phased in a relatively challenging and complex context, where various novel and inventive technological approaches have been developed to facilitate the task of generating effective ODCs for motion-based skills. It will be appreciated that not all aspects of the methodologies described herein are present in all embodiments, or used in the context of all activities. The technology is applicable to a wide range of physical activities, with varying levels of complexity (for example in terms of performance, coaching, and monitoring). However, methodologies described herein are applicable across a wide range of activities, for example skills performed in the context of individual and team sports.

The methodologies and technology detailed below are described by reference to specific examples relating to a particular physical activity: rowing. The skill is a standard rowing stroke. Rowing has been selected as an example primarily for the purposes of convenient textual explanation, and it will readily be appreciated how techniques described by reference to that particular activity are readily applied to other activities (for example performing a particular form of kick of a soccer ball, swinging a golf club, performing an acrobatic manoeuvre on a snowboard, and so on).

In general terms, there are a wide range of approaches for determining ODCs for a given physical activity. These include, but are not limited to, the following:

Utilisation of secondary technologies, thereby to streamline understanding of MSD. For example, examples provided below discuss an approach that utilises combination of MCD and MSD. MCD is used primarily due to the established nature of motion capture technology (for example using powerful high speed cameras); motion sensor technology on the other hand is currently continually advancing in efficacy. The use of well-established MCD analysis technology assists in understanding and/or validating MSD and observations made in respect of MSD.

Direct utilisation of MSD, without MCD assistance. For instance, MSD is utilised in a similar manner to MCD, in the sense of capturing data thereby to generate three dimensional body models similar to those conventionally generated from MCD (for example based on a body avatar with skeletal joints) It will be appreciated that this assumes a threshold degree of accuracy and reliability in MCD. However, in some embodiments this is able to be achieved, hence rendering MCD assistance unnecessary.

Machine learning methods, for example where MSD and/or MCD is collected for a plurality of sample performances, along with objectively defined performance outcome data (for example, in the case or rowing: power output; and in the case of golf: ball direction and trajectory). Machine learning method are implemented thereby to enable automated defining of relationships between ODCs and effects on skill performance. Such an approach, when implemented with a sufficient sample size, enables computer identification of ODCs to drive prediction of skill performance outcome. For example, based on machine learning of golf swing motions using sample performance collection of MSD (or, in some embodiments, MCD), ODCs that affect swing performance are automatically identified using analysis of objectively defined outcomes, thereby to enable reliable automated prediction of an outcome in relation to an end-user swing using end-user hardware (for example a MSU-enabled garment).

Remote collection of analysis data from end users. For example, end user devices are equipped with a "record" function, which enables recording of MSD representative of a particular skill as respectively performed by the end users (optionally along with information regarding symptoms and the like identified by the users themselves). The recorded data is transmitted to a central processing location to compare the MSD for a given skill (or a particular skill having a particular symptom) for a plurality of users, and hence identify ODCs for the skill (and/or symptom). For example, this is achieved by identifying commonalities in the data.

Other approaches may also be used, including other approaches that make use of non-MSD data to validate and/or otherwise assist MSD data, and also including other approaches that implement different techniques for defining and analysing a sample user group.

The first example above is considered in more detail below, by reference to specific example embodiments which are directed to enabling subjective expert coaching knowledge to contribute towards the development of ODCs for symptoms and/or causes that are able to be used in the context of skills training programs.

Skill Analysis Phase—Sample Analysis Example

In some example embodiments, for each skill to be trained, there is a need to perform initial analysis of the motions involved in that skill, using one or more sample skill performers, thereby to enable determination of differences between optimal performance and sub-optimal performance (and hence enable coaching towards optimal performance). In general terms, this begins with visual analysis, which is subsequently translated (via one or more intermediary processes) into analysis of motion sensor data (referred to as monitoring for Observable Data Conditions, or ODCs).

The example techniques described herein include obtaining data representative of physical skill performances (for a given skill) by a plurality of sample subjects. For each physical skill performance, the data preferably includes:

(i) Video data, captured by one or more capture devices from one or more capture angles. For example, in the context of rowing, this may include a side capture angle and a rear capture angle.

(ii) Motion capture data (MCD), using any available motion capture technique. In this regard, "motion capture" refers to a technique whereby capture devices are used to capture data representative of motion, for example using visual markers mounted to a subject at known locations. An example is motion capture technology provided by Vicon (although no affiliation between the inventors/applicant and Vicon is to be inferred).

(iii) Motion sensor data (MSD), using one or more body-mounted motion sensors.

In each case, a preferred approach is to store both (i) raw data, and (ii) data that has been subjected to a degree of processing. This is particularly the case for motion sensor data; raw data may be re-processed over time as newer/better processing algorithms become available thereby to enhance end-user functionality.

In overview, the general concept is to use the MCD as a stepping stone between video data (which is most useful to real-world coaches) and MSD (which is required for the ultimate end-user functionality, which involves coaching via analysis of data derived from a MSU-enabled garment). MCD presents a useful stepping stone in this regard, as (i) it is a well-developed and reliable technology; and (ii) it is well-suited to monitor the precise relative motions of body parts.

Figure 2A:
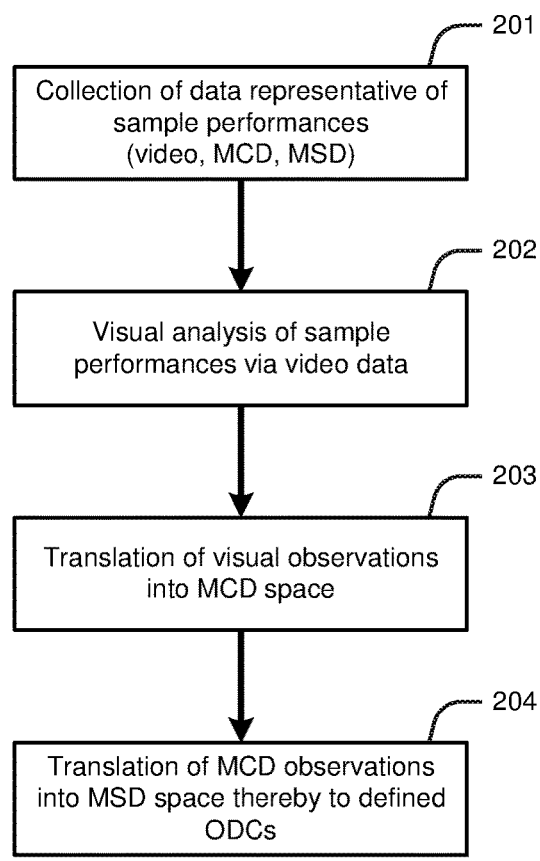
FIG. 2A illustrates a skill analysis method according to one embodiment.

The overall technique includes the following phases: (i) collection of data representative of sample performances by the selected subjects; (ii) visual analysis of sample performances by one or more coaches using video data; (iii) translation of visual observations made by the one or more coaches into the MCD space; and (iv) analysing the MSD based on the MCD observations thereby to identify ODCs in the MSD space that are, in a practical sense, representative of the one or more coaches' observations. Each of these phases is discussed in more detail below. This is illustrated in FIG. 2A via blocks 201 to 204.

Figure 2B:
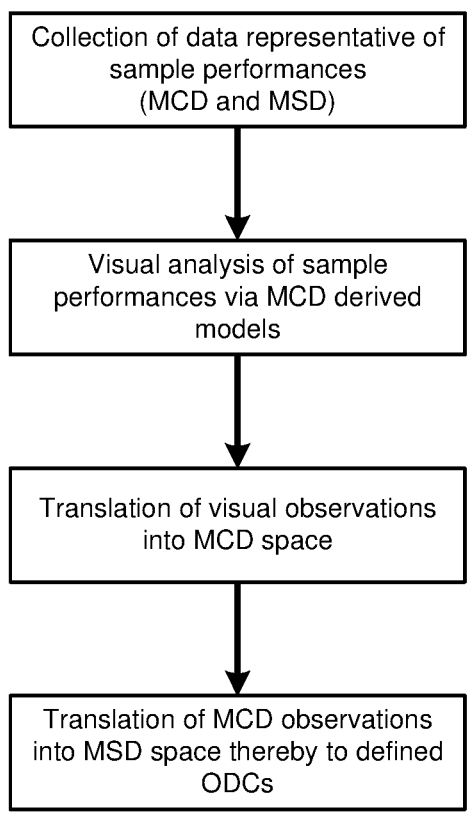
FIG. 2B illustrates a skill analysis method according to one embodiment.
Figure 2C:
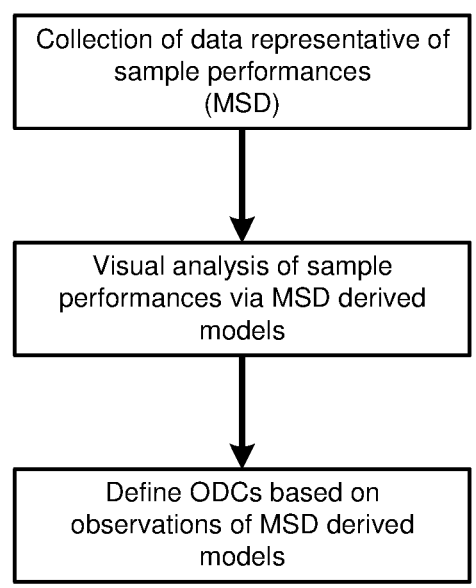
FIG. 2C illustrates a skill analysis method according to one embodiment.
Figure 2D:
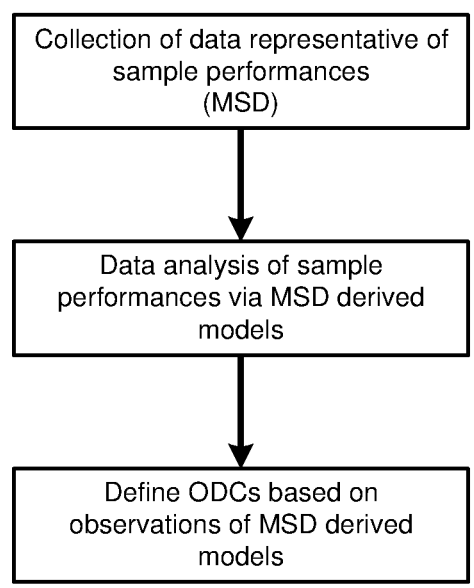
FIG. 2D illustrates a skill analysis method according to one embodiment.
Figure 2E:
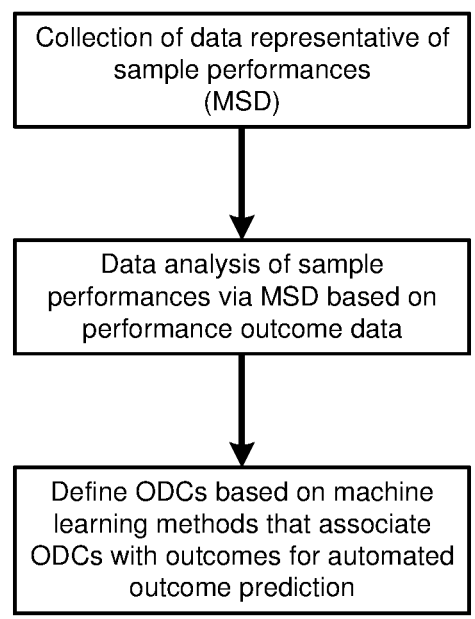
FIG. 2E illustrates a skill analysis method according to one embodiment.

Alternate methods are illustrated in FIG. 2B (which omits collection of video data, and instead visual analysis is performed via digital models generated using MCD), FIG. 2C (in which only MSD is used, and visual analysis is achieved using computer-generated models based on the MSD), FIG. 2D (in which there is no visual analysis, only data analysis of MCD to identify similarities and differences between samples) and FIG. 2E, which makes use of machine learning via MSD (MSD is collected for sample performances, data analysis is performed based on outcome data, such objectively measures one or more outcome parameters of a sample performance, and ODCs are defined based on machine learning thereby to enable prediction of outcomes based on ODCs).

In terms of using "one or more" coaches, in some cases multiple coaches are used thereby to define a consensus position with respect to analysis and coaching of a given skill, and in some cases multiple coaches are alternatively/additionally used to define coach-specific content. The latter allows an end user to select between coaching based on the broader coaching consensus, or coaching based on the particular viewpoint of a specific coach. At a practical level, in the context of a commercial implementation, the latter may be provided as basis for a premium content offering (optionally at a higher price point). The term "coach" may be used to describe a person who is qualified as a coach, or a person who operates in a coaching capacity for the present purposes (such as an athlete or other expert).

Skill Analysis Phase—Subject Selection Example

Subject selection includes selecting a group of subjects that are representative for a given skill. In some example embodiments, sample selection is performed to enable normalisation across one or more of the following parameters:

(i) Ability level. Preferably a plurality of subjects are selected such that there is adequate representation across a range of ability levels. This may include: initially determining a set of known ability levels, and ensuring adequate subject numbers for each level; analysing a first sample group, identifying ability level representation from within that group based on the analysis, and optionally expanding the sample group for under-represented ability levels, or other approaches. In embodiments described herein, user ability level is central to the automated coaching process at multiple levels. For example, as discussed further below, an initial assessment of user ability level is used to determine how a POD device is configured, for example in terms of ODCs for which it monitors. As context, mistakes made by a novice will differ from mistakes made by an expert. Moreover, it is advantageous to provide coaching directed to a user's actual ability level, for instance by first providing training thereby to achieve optimal (or near-optimal) performance at the novice level, and subsequently providing training thereby to achieve optimal (or near-optimal) performance at a more advanced level.

(ii) Body size and/or shape. In some embodiments, or for some skills, body size and/or shape may have a direct impact on motion attributes of a skill (for example by reference to observable characteristics of symptoms). An optional approach is to expand a sample such that it is representative for each of a plurality of body sizes/shapes, ideally at each ability level. As discussed further below, body size/shape normalisation is in some embodiments alternately achieved via a data-driven sample expansion method, as discussed further below. In short, this allows for a plurality of MCD/MSD data sets to be defined for each sample user performance, by applying a set of predefined transformations to the collected data thereby to transform that data across a range of different body sizes and/or shapes.

(iii) Style. Users may have unique styles, which do not materially affect performance. A sample preferably includes sufficient representation to enable normalisation across styles, such that observational characteristics of symptoms are style-independent. This enables coaching in a performance-based manner, independent of aspects of individual style. However, in some embodiments at least a selection of symptoms is defined in a style-specific manner. For example, this enables coaching to adopt a specific style (for example to enable coaching towards the style of a particular athlete).

For the sake of simplicity, the following description focuses on normalisation for multiple ability levels. In an example embodiment, there are "m" ability levels ($AL_1$ to $AL_m$) and "n" subjects ($SUB_1$ to $SUB_n$) at each ability level. That is, there are m*n subjects overall. It will be appreciated that the number of subjects at each individual ability level need not be equal (for example in some embodiments additional subjects are observed at a given ability level thereby to obtain more reliable data).

As noted, in some embodiments a sample is expanded over time, for example based on identification that additional data points are preferable.

Skill Analysis Phase—Performance Regime Definition Examples

In some example embodiments, each test subject ($SUB_1$ to $SUB_n$ at each of $AL_1$ to $AL_m$) performs a defined performance regime. In some embodiments the performance regime is constant across the plurality of ability levels; in other embodiments a specific performance regime is defined for each ability level. As context, in some cases a performance regime includes performances at varying intensity levels, and certain intensity levels may be inappropriate below a threshold ability level.

Some embodiments provide a process which includes defining an analysis performance regime for a given skill. This regime defines a plurality of physical skill performances that are to be performed by each subject for the purpose of sample data collection. Preferably, an analysis performance regime is defined by instructions to perform a defined number of sets, each set having defined set parameters. The set parameters preferably include:

(i) For each set, a number of repetitions. For example, a set may comprise n repetitions (where n≥1), in which the subject repeatedly attempts the skill with defined parameters.

(ii) Repetition instructions. For example, how much rest between repetitions.

(iii) Intensity parameters. For example, a set may be performed at constant intensity (each repetition $REP_1$ to $REP_n$ at the same intensity $I_c$), increasing intensity (performing repetition $R_1$ at intensity $I_1$, then performing $REP_2$ at intensity $I_2$, where $I_1 > I_2$, and so on), or decreasing intensity (performing repetition REP, at intensity $I_1$, then performing $R_2$ at intensity $I_2$, where $I_1 < I_2$, and so on), or more complex intensity profiles. The manner by which intensity is defined is dependent on the activity. For example, intensity parameters such as speed, power, frequency, and the like may be used. Such measures in some cases enable objective measurement and feedback. Alternately, a percentage of maximum intensity (for example "at 50% of maximum"), which is subjective but often effective.

By way of example, a given analysis performance regime for analysing a skill in the form of a rowing motion on an erg machine (a form of indoor rowing equipment) may be defined as follows:

Perform 6 sets ($SET_1$ to $SET_6$), with 5 minutes rest between sets.

For each set, perform 8 continuous repetitions ($REP_1$ to $REP_8$).

Intensity parameters are: $SET_1$ at Intensity=100 W; $SET_2$ at Intensity=250 W; $SET_3$ at Intensity=400 W; $SET_4$ at Intensity=550 W; $SET_5$ at Intensity=700 W; and $SET_6$ at Intensity=850 W.

Reference to the example of rowing is continued further below. However, it should be appreciated that this is a representative skill only provided for the sake of illustration, and that the underlying principles are applicable to a wide range of skills.

Skill Analysis Phase—Example Data Collection Protocol

Data is collected and stored in respect of each user's completion of the performance regime. As noted, for the present example. In the primary example considered herein, the data includes:

(i) Video data, captured by one or more capture devices from one or more capture angles. For example, one or more of a front, rear, side, opposite side, top, and other camera angles may be used.

(ii) Motion capture data (MCD), using any available motion capture technique.

(iii) Motion sensor data (MSD), using one or more body-mounted motion sensors.

It is preferable to control conditions under which data collection is performed, thereby to achieve a high degree of consistency and comparability between samples. For example, this may include techniques such as ensuring consistent camera placement, using markers and the like to assist in subject positioning, accurate positioning of MSUs on the subject, and so on.

Collected data is organised and stored in one or more databases. Metadata is also preferably collected and stored, thereby to provide additional context. Furthermore, the data is in some cases processed thereby to identify key events. In particular, events may be automatically and/or manually tagged in data for motion-based events. For example, a repetition of a given skill may include a plurality of motion events, such as a start, a finish, and one or more intermediate events. Events may include the likes of steps, the moment a ball is contacted, a key point in a rowing motion, and so on. These events may be defined in each data set, or on a timeline that is able to be synchronised across the video data, MCD and MSD.

Skill Analysis Phase—Example Data Synchronisation

Each form of data is preferably configured to be synchronised. For example:

Video data and MCD is preferably configured to be synchronised thereby to enable comparative review. This may include side-by-side video review (particularly useful for comparative analysis of video/MCD captured from different viewing angles) and overlaid review, for example using partial transparency (particularly useful for video/MCD captured for a common angle).

MSD is preferably configured to be synchronised such that data from multiple MSUs is transformed/stored relative to a common time reference. This in some embodiments is achieved by each MSU providing to the POD device data representative of time references relative to its own local clock and/or time references relative to an observable global time clock. Various useful synchronisation techniques for time synchronisation of data supplied by distributed nodes are known from other information technology environments, including for example media data synchronisation.

The synchronisation preferably includes time-based synchronisation (whereby data is configured to be normalised to a common time reference), but is not limited to time-based synchronisation. In some embodiments event-based synchronisation is used in addition to or as an alternative to time-based synchronisation (or as a means to assist time-based synchronisation).

Event-based synchronisation refers to a process whereby data, such as MCD or MSD, includes data representative of events. The events are typically defined relative to a local timeline for the data. For example, MCD may include a video file having a start point at 0:00:00, and events are defined at times relative to that start point. Events may be automatically defined (for example by reference to an event that is able to be identified by a software process, such as a predefined observable signal) and/or manually defined (for example marking video data during manual visual review of that data to identify times at which specific events occurred).

In the context of MCD, data is preferably marked to enable synchronisation based on one or more performance events. For example, in the context of rowing, various identifiable motion points in a rowing motion are marked, thereby to enable synchronisation of video data based on commonality of motion points. This is particularly useful when comparing video data from different sample users: it assists in identifying different rates of movement between such users. In some cases motion point based synchronisation is based on multiple points, with a video rate being adjusted (e.g. increased in speed or decreased in speed) such that two common motion points in video data for two different samples (e.g. different users, different repetitions, different sets, etc) are able to be viewed side-by-side (or overlaid) to show the same rate of progression between these motion points. For example, if one rower has a stroke time of 1 second, and another has a stroke time of 1.2 seconds, motion point based synchronisation is applied such that latter is contracted to one second thereby to enable a more direct comparison between the motion of the two rowers.

Skill Analysis Phase—Example Data Expansion Methodology

In some embodiments, MSD and/or MCD is transformed for each subject via a data expansion process thereby to define a plurality of further "virtual subjects" having different body attributes. For example, transformations are defined thereby to enable each MCD and/or MSD data point to be transformed based on a plurality of different body sizes. This enables capture of a performance from a subject having a specific body size to be expanded into a plurality of sample performances reflective of different body sizes. The term "body sizes" refers to attributes such as height, torso length, upper leg length, lower leg length, hip width, shoulder width, and so on. It will be appreciated that these attributes would in practice alter the movement paths and relative positions of markers and MSUs used for MCD and MSD data collection respectively.

Data expansion is also useful in the context of body size normalisation, in that data collected from all sample performers is able to be expended into a set of virtual performances that include one or more virtual performances by virtual performers having "standard" body sizes. In some embodiments a single "standard" body size is defined. The use of a standard body size, and transformation of MSD and MCD from sample performances to that standard body size, allows for direct comparison of MCD and MSD in spite of body size differences of multiple sample performers.

Skill Analysis Phase—Example Visual Analysis Methodology

As noted above, and shown in block 202 of FIG. 2A, an aspect of an example skill analysis methodology includes visual analysis of sample performances via video data. In other embodiments the video analysis is performed using computer-generated models derived from MCD and/or MSD as an alternative to video data, or in addition to video data. Accordingly, although examples below focus on review based on video data, it should be appreciated that such examples are non-limiting, and the video data is in other examples substituted for models generated based on MCD and/or MSD.

Visual analysis is performed for a variety of purposes, including: preliminary understanding of a skill and components of that skill; initial identification of symptoms; and analysis of individual sample performances based on a defined analysis schema.

Figure 3:
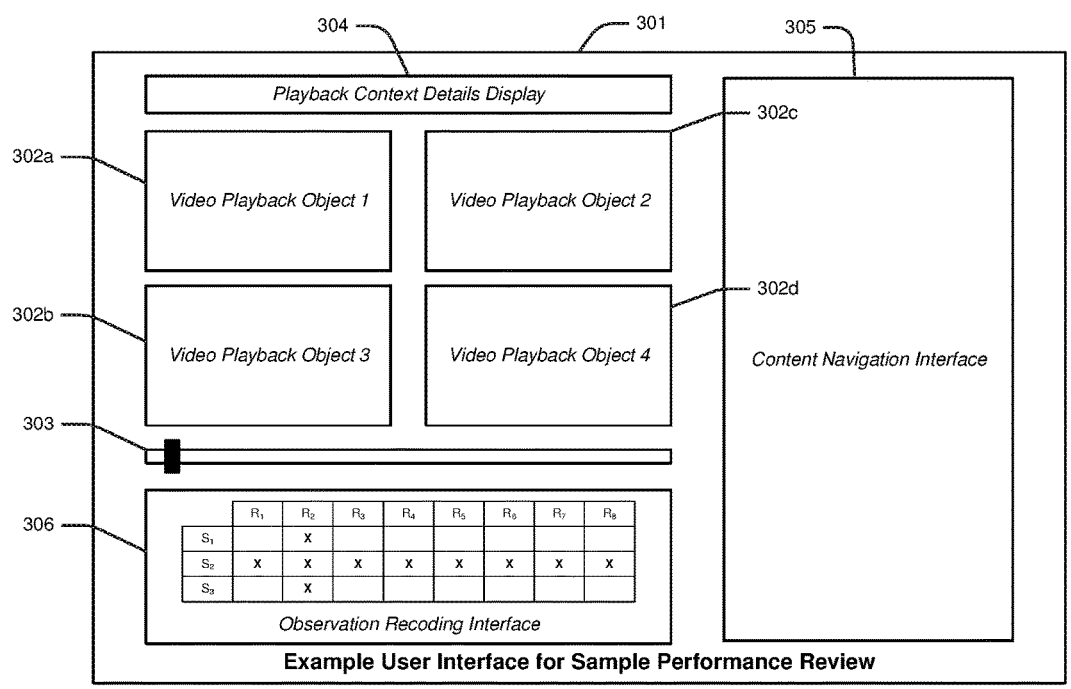
FIG. 3 illustrates a user interface display view for a user interface according to one embodiment.

FIG. 3 illustrates an example user interface 301 according to one embodiment. It will be appreciated that specially adapted software is not used in all embodiments; the example of FIG. 3 is provided primarily to illustrate key functionalities that are of particular use in the visual analysis process.

User interface 301 includes a plurality of video display objects 302a-302d, which are each configured to playback stored video data. In some embodiments the number of video display objects is variable, for example based on (i) a number of video capture camera angles for a given sample performance, with a video display object provided for each angle; and (ii) user control. In terms of user control, a user is enabled to select video data to be displayed, either at the performance level (in which case multiple video display objects are collectively configured for the multiple video angles associated with that performance) or on an individual video basis (for example selecting a particular angle from one or more sample performances). Each video display object is configured to display either a single video, or simultaneously display multiple videos (for example two videos overlaid on one another with a degree of transparency thereby to enable visual observation of overlap and differences). A playback context display 304 provides details of what is being shown in the video display objects.

Video data displayed in objects 302a to 302d is synchronised, for example time-synchronised. A common scroll bar 303 is provide to enable synchronous navigation through the multiple synchronised videos (which, as noted, may include multiple overlaid video objects in each video display object). In some embodiments a toggle is provided to move between time synchronisation and motion event based synchronisation.

A navigation interface 305 enables a user to navigate available video data. This data is preferably configured to be sorted by reference to a plurality of attributes, thereby to enable identification of desired performances and/or videos. For example, one approach is to sort firstly by skill, then by ability level, and then by user. In a preferred embodiment a user is enabled to drag and drop performance video data sets and/or individual videos into video display objects.

FIG. 3 additionally illustrates an observation recording interface 306. This is used to enable a user to record observations (for example complete checklists, make notes and the like), which are able to be associated with a performance data set that is viewed. Where multiple performance data sets are viewed, there is preferably a master set, and one or more overlaid comparison sets, and observations are associated with the master set.

Skill Analysis Phase—Example Symptom Identification via Visual Analysis

In an example embodiment, multiple experts (for example coaches) are engaged to review sample performances thereby to identify symptoms. In some cases this is facilitated by an interface such as user interface 301, which provides an observation recording interface 306. Example methods of extracting knowledge from experts are discussed in PCT/AU2016/000020.

Skill Analysis Phase—Example Determining of ODCs (e.g. for State Engine Data)

Following visual analysis by experts/coaches, the skill analysis phase moves into a data analysis sub-phase, whereby the expert knowledge obtained from visual analysis of sample performances is analysed thereby to define ODCs that enable automated detection of symptoms based on MSD. For example, such ODCs are used in state engine data which is later downloaded to end user hardware (for example POD devices), such that a training program is able to operate based on input representing detection of particular symptoms in the end user's physical performance.

It will be appreciated that a range of different methodologies are used in various embodiments to define ODCs for a given symptom. In some embodiments, a general methodology includes:

(i) Performing analysis of MSD thereby to identify a combination of data attributes (for example based on MSD including acceleration rates and directions), which based on the outcomes of visual analysis are predicted to be indicative of the presence of a symptom;

(ii) Testing those data attributes against data representative of the sample performances (for example using the actual recorded MSD) to verify that those data attributed are present in all sample performances displaying the relevant symptom (optionally at an ability-level specific basis); and (iii) Testing those data attributes against data representative of the sample performances (for example using the actual recorded MSD) to verify that those data attributed are not present sample performances that do not display the relevant symptom (again, optionally at an ability-level specific basis).

Examples include, but are not limited to the following:

Approaches that use MCD as a stepping stone between visual analysis and MSD;

Approaches that move directly from visual analysis to analysis of MSD;

Approaches that define ODCs based on data obtained from individual sensors; and

Approaches that define ODCs based on overall body movement using a virtual body model constructed from MSD.

A selection of examples are described in detail below.

ODCs are also in some embodiments tuned thereby to make efficient use of end-user hardware, for example by defining ODCs that are less processor/power intensive on MSUs and/or a POD device. For example, this may be relevant in terms of sampling rates, data resolution, and the like.

Skill Analysis Phase—Example Translation of Visual Observations into MCD Space

As noted above, in some embodiments the MCD space is used as a stepping stone between visual observations and MSD data analysis. This is useful in avoiding challenges associated with accurately defining a virtual body model based on MSD (for example noting challenges associated with transforming MSD into a common geometric frame of reference).

In overview, the process includes, for a given symptom, analysing MCD associated with performances that have been marked as displaying that symptom. This analysis is in some embodiments performed at an ability level specific basis (noting that the extent to which a symptom is observable from motion may vary between ability levels). For example, the analysis includes comparing MCD (such as a computer generated model derived from MCD) for samples displaying the relevant symptom with MDC for samples which do not display the symptom.

Figure 5:
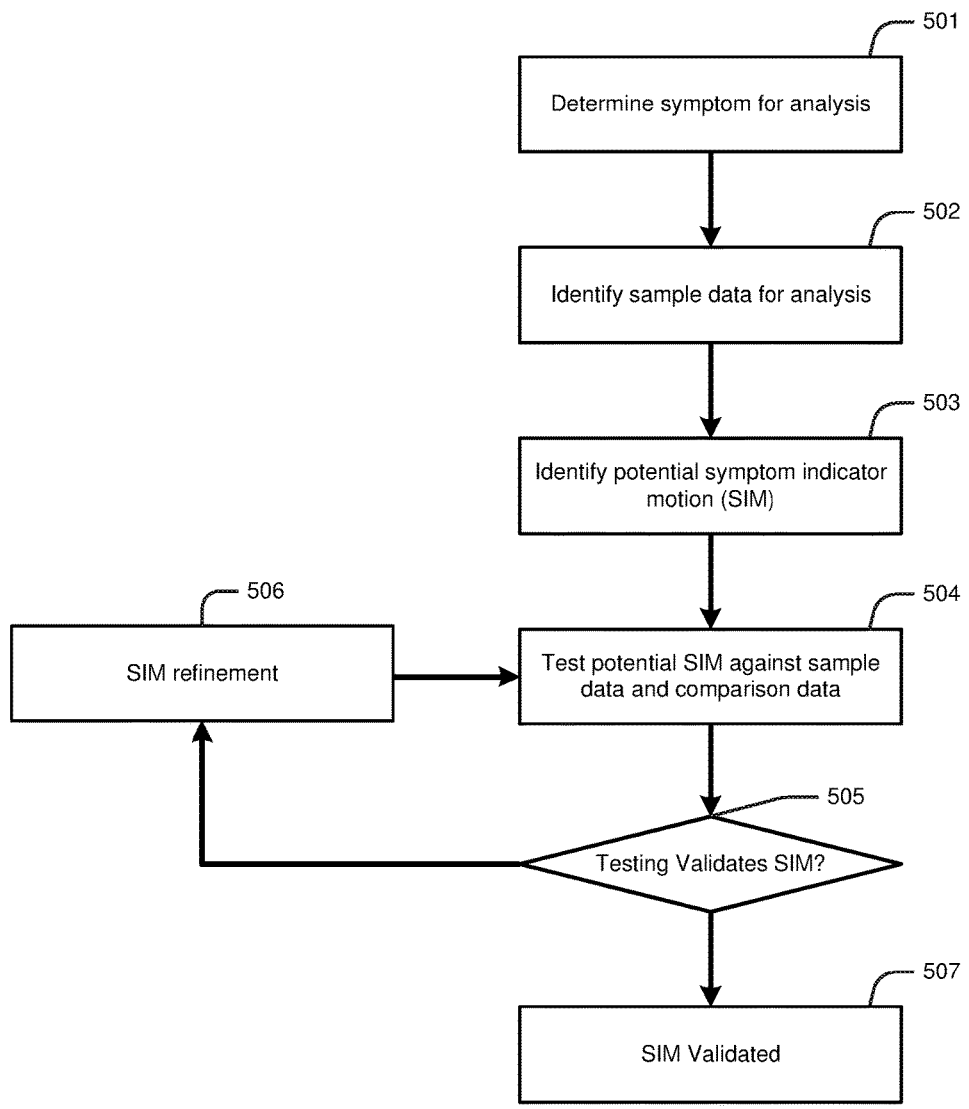
FIG. 5 illustrates a SIM analysis method according to one embodiment.

FIG. 5 illustrates a method according to one embodiment. It will be appreciated that this is an example only, and various other methods are optionally used to achieve a similar purpose. Block 501 represents a process including determining a symptom for analysis. For example, in the context of rowing, the symptom may be "snatched arms". Block 502 represents a process including identifying sample data for analysis. For example, the sample data may include:

MCD for all repetitions associated with the symptom.

MCD for all repetitions associated with the symptom at specific intensity parameters. That is, the analysis considers how a symptom presents at specific intensity parameters (as opposed to other intensity parameters).

MCD for all repetitions associated with the symptom at a specific ability level. That is, the analysis considers how a symptom presents at a specific ability level (as opposed to other ability levels).

MCD for all repetitions associated with the symptom at specific intensity parameters and a specific ability level (i.e. combining the two previous approaches).

Other approaches may also be used. In some cases multiple of the above approaches are used in combination to better understand the effect of factors such as intensity and ability (which may turn out to be relevant or irrelevant to a given symptom).

The MCD used here is preferably MCD normalised to a standard body size, for example based on sample expansion techniques discussed above. Likewise, ODCs derived from such processes are able to be de-normalised using transformation principles of sample expansion thereby to be applicable to a variable (and potentially infinitely variable) range of body sizes.

Functional block 503 represents a process including identifying a potential symptom indicator motion (SIM). For example, this includes identifying an attribute of motion observable in the MCD for each of the sample repetitions which is predicted to be representative of the relevant symptom. An indicator motion is in some embodiments defined by attributes of a motion path of a body part at which a MSU is mounted. The attributes of a motion path may include the likes of angle, change in angle, acceleration/deceleration, change in acceleration/deceleration, and the like. This is referred to herein as "point path data", being data representative of motion attributes of a point defined on a body. In this regard, a potential SIM is defined by one or more sets of "point path data" (that is, in some cases there is one set of point path data, where the SIM is based on motion of only one body part, and in some cases there are multiple sets of point path data, where the SIM is based on motion of multiple body parts such as a forearm and upper arm).

As context, a set of point path data may be defined to include the following data for a given point:

X-axis acceleration: Min: A, Max B.

Y-axis acceleration: Min: C, Max D.

Z-axis acceleration: Min: E, Max F.

Data other than acceleration may also be used. Furthermore, there may be multiple acceleration measurements, and these may be time referenced to other events and/or measurements.

For example, one set of point path data may be constrained by reference to a defined time period following observation of another set of point path data. As context this could be used to define SIM that considers relative movement of a point on the upper leg with a point on the forearm.

Functional block 504 represents a testing process, whereby the potential SIM is tested against comparison data. In some embodiments the testing validates that:

(i) The one or more sets of point path data are observed in the MCD for each of the repetitions in the sample data. This validates that the potential SIM is effective in terms of identifying the presence of the symptom in the sample for which it is designed to operate.

(ii) The one or more sets of point path data are not observed in the MCD for repetitions that are not associated with the relevant symptom. This validates that the potential SIM will not be triggered where the symptom is not present.

Decision 505 represents determination of whether the potential SIM is validated based on testing at 505.

Where a potential SIM is not able to be successfully validated, it is refined (see block 506) and re-tested. In some embodiments refinement and re-testing is automated via an interactive algorithm. For example, this operates to narrow down point path data definitions underlying a previously defined potential SIM to a point where it is able to be validated as unique by reference to MCD for performance repetitions for which the relevant symptom is not present. In some cases a given SIM is not able to be validated following a threshold number of iterations, and a new staring point potential SIM is required.

Block 507 represents validation of a SIM following successful testing.

In some embodiments, where the sample data is a subset of the total MCD data for all repetitions associated with the relevant symptom, data is generated to indicate whether the SIM is validated also for any other subsets of that total MCD data (for example the SIM is derived based on analysis at a first ability level, but also valid at a second ability level).

It should be appreciated that the process of determining potential SIMs may be a predominately manual process (for example based on visual analysis of video and/or MCD derived model data). However, in some embodiments the process is assisted by various levels of automation. For example, in some embodiments an algorithm is configured to identify potential SIMs based on commonality of MCD in symptom-displaying MCD as compared with MCD in symptom-absent MCD. Such an algorithm is in some embodiments configured to define a collection of potential SIMs (each defined by a respective one or more sets of point path data, in the MCD space or the MSD space) which comprehensively define uniqueness of sample set of symptom-displaying sample performances relative to all other sample performances (with the sample performances being normalised for body size). In one embodiment, an algorithm is configured to output data representative of a data set containing all MCD common to a selected symptom or collection of symptoms, and enable filtering of that data set (for example based on particular sensors, particular time windows within a motion, data resolution constraints, and so on) thereby to enable user-guided narrowing of the data set to a potential SIM that has characteristics that enable practical application in the context of end-user hardware (for example based on MCDs of MSU-enabled garments provided to end users).

In some embodiments the testing process is additionally used to enable identification of symptoms in repetitions where visual analysis was unsuccessful. For example, where the number of testing failures is small, those are subjected to visual analysis to confirm whether the symptom is indeed absent, or subtly present.

Skill Analysis Phase—Example Translation from MCD Space Into MSD Space (ODCs)

SIMs validated via a method such as that of FIG. 5 are then translated into the MSD space. As noted, each SIM includes data representative of one or more sets of point path data, with each set of point path data defining motion attributes for a defined point on a human body.

The points on the human body for which point path data is defined preferably correspond to points at which MSUs are mounted in the context of (i) a MSU arrangement worn by subjects during the sample performances; and (ii) a MSU-enabled garment that is utilised by end users. In some embodiments the end user MSU-enabled garment (or a variation thereof) is used for the purposes of sample performances.

In the case that point path data is defined for a point other than that where a MSU is mounted, a data transformation is preferably performed thereby to adjust the point path data to such a point. Alternately, such a transformation may be integrated into a subsequent stage.

In overview, MSD for one or more of the sample performance repetitions in sample data (the sample data of block 502 of FIG. 5) is analysed thereby to identify data attributes corresponding to the point path data. For example, the point path data may be indicative of one or more defined ranges of motion and/or acceleration directions relative to a frame of reference (preferably a gravitational frame of reference).

In some embodiments, the translation from (a) a SIM derived in the MCD space into (b) data defined the MSD space includes:
 (i) For each set of point path data, identifying MSD attributes, present in each of the sample performances to which the SIM relates, that are representative of the point path data. In some cases, the relationship between point path data and attributes of MSD is imperfect, for example due to the nature of the MSD. In such cases, the identified MSD attributes may be broader than the motions defined by the point path data.
 (ii) Validating the identified MSD data attributes by a process similar to the iterative testing of blocks 504-506 of FIG. 5, thereby to validate that the identified MSD attributes are consistently found in the MSD for symptom-displaying sample performances, and absent in all symptom-absent sample performances.

This process of translation into the MSD space results in data conditions which, when observed in data derived from one or more MSUs used during the collection phase (e.g. block 201 of FIG. 2A), indicates the presence of a symptom. That is, the translation process results in ODCs for the symptom.

ODCs defined in this manner are defined by individual sensor data conditions for one or more sensors. For example, ODCs are observed based upon velocity and/or acceleration measurements at each sensor, in combination with rules (for example timing rules: sensor X observes A, and within a defined time proximity sensor X observes B).

The ODCs are then able to be integrated into state engine data, which is configured to be made available for downloading to an end user device, thereby to enable configuration of that end user device to monitor for the relevant symptoms.

It will be appreciated that the ODCs defined by the translation process above are unique to the MSUs used in the data collection phase. For this reason, it is convenient to use the same MSUs and MSU positioning (for example via the same MSU-enabled garment) during the collection phase as will be used by end users. However, in some embodiments there are multiple versions of end-user MSU-enabled garments, for example with different MSUs and/or different MSU positioning. In such cases, the translation into the MSD space is optionally performed separately for each garment version. This may be achieved by applying known data transformations and/or modelling of the collected test data via virtual application of virtual MSU configurations (corresponding to particular end-user equipment). For example, in relation to the latter, a virtual model derived from MCD is optionally used as a framework to support one or more virtual MSUs, and determine computer-predicted MSU readings corresponding to SIM data. It will be appreciated that this provides an ability to re-defined ODCs over time based on hardware advances, given that data collected via the analysis phase is able to be re-used over time in such situations.

Figure 6:
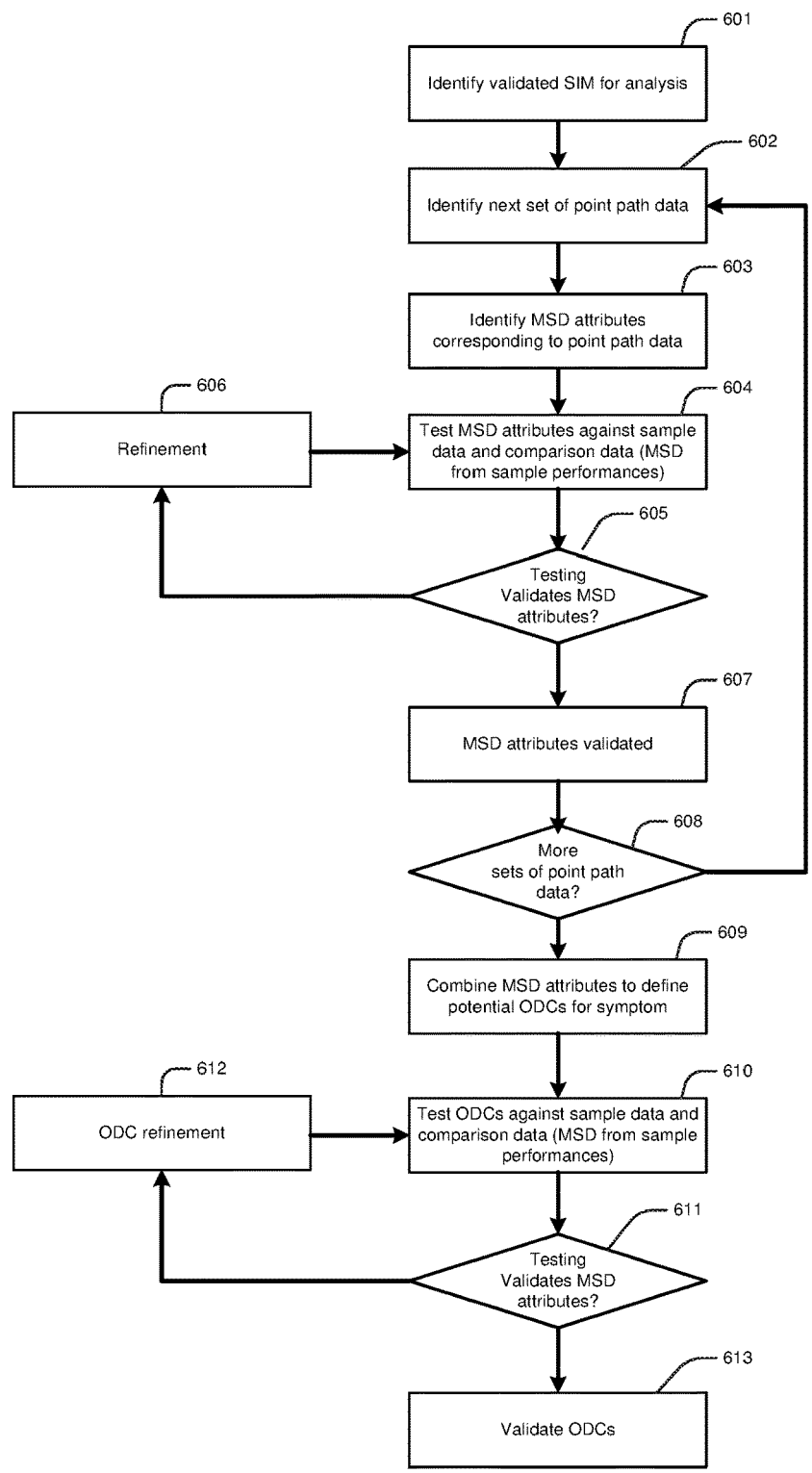
FIG. 6 illustrates a SIM analysis method according to one embodiment.

An example process is illustrated in FIG. 6, being a process for defining ODCs or a SIM generated based on MSC analysis. A validated SIM is identified at 601. A first one of the sets of point path data is identified at 602, and this is analysed via a process represented by blocks 603 to 608, which loops for each set of point path data. This looped process includes identifying potential MSD attributes corresponding to the point path data. For example, in some embodiments this includes processing collected MSD for the same point in time as the point path data for all or a subset of the relevant collected MSD (noting that MCD and MSD is stored in a manner configured for time synchronisation). Testing is then performed at 604, to determine at 605 whether the identified MSD attributes are present in all relevant symptom-present MSD collected from sample performances (and, in some embodiments to ensure it is absent in symptom-absent MSD). Where necessary, refinement is performed at 606, otherwise the MSD attributes are validated to 607.

Once the looped process of blocks 603 to 608 is completed for all sets of point path data in the SIM, the validated MSD attributes are combined at 609, thereby to define potential ODCs for the symptom. These are then also tested, refined and validated via the processes of blocks 610 to 613, thereby to ensure that the potential ODC is: (i) identified in all relevant sample performance MSD for which the relevant symptom is indeed present, and (ii) not identified in all relevant sample performance MSD for which the relevant symptom is absent (the term "relevant" indicating that in some cases analysis is limited by ability level or the like)

It will be appreciated that various alternate methodologies are used in further embodiments thereby to define ODCs for a given symptom. However, in substantially all cases method includes performing analysis thereby to define observable data conditions that are able to be identified in MSD (collected or virtually defined) for sample performances where the symptom is present, but not able to be identified in sample performances where the symptom is absent.

Skill Analysis Phase—Alternate Translation of Visual Observations Into MCD Space Via MCD Space In a further embodiment, MCD is used to generate a virtual body model, and that model is associated with time-synchronised MSD. In that manner, analysis is able to be performed using MSD for a selected one or more MSUs at a particular point in a skill performance motion.

The MSD used at this stage may be either MSD for a particular performance, or MSD aggregated across a subset of like performances (for example performances by a standardized body size at a defined ability level). The aggregation may include either or both of: (i) utilising only MSD that is similar/identical in all of the subset of performances; and (ii) defining data value ranges such that the aggregated MSD includes all (or a statistically relevant proportion) of MSD for the subset of performances. For example, in relation to the latter, MSD for a first performance might have: a value of A for x-axis acceleration of a particular sensor at a particular point in time, and MSD for a second performance might have: a value of B for x-axis acceleration of that particular sensor at that particular point in time. These are able to be aggregated into aggregated MSD where the value for x-axis acceleration of that particular sensor at that particular point in time is defined as being between A and B.

Hence, analysis is able to be performed to determine the likes of:
  (i) Values for one or more aspects of MSD (e.g. accelerometer values) for a particular sensor, at a particular point in a movement, for a specific performance.
  (ii) Comparison data comparing the values at (i) with other performances at the same point in the movement (for example other performances displaying the same symptom at the same ability level).
  (iii) Value ranges for one or more aspects of MSD (e.g. accelerometer values) for a particular sensor, at a particular point in a movement, for set of performances (for example other performances displaying the same symptom at the same ability level).
  (iv) Comparison data for one or more aspects of MSD (e.g. accelerometer values) for a particular sensor, at a particular point in a movement, for a specific performance having a specific symptom, as compared with corresponding MSD for one or more further performances that do not display that specific symptom.

Such analysis is used to determine predicted ODCs for a given symptom.

Figure 7:
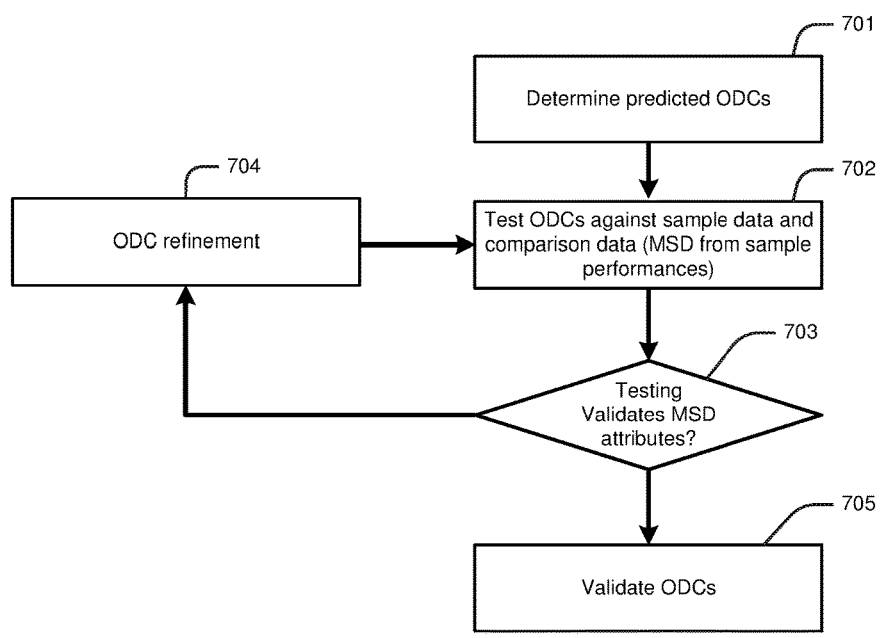
FIG. 7 illustrates an ODC validation method according to one embodiment.

Once predicted ODCs are defined, these are able to be tested using a method such as that shown in FIG. 7. Predicted ODCs for a particular symptom are determined at 701, and these are then tested against MSD for sample performances at 702. As with previous example, this is used to verify that the predicted ODCs are present in MSD for relevant performances displaying that symptom, and that the ODCs are not present in MSD for relevant performances that do not display the symptom. For example, the "relevant" performances are sample performances at a common ability level and in some embodiments normalised to a standard body size. Based on the testing the ODCs are refined at 704, or validated at 705.

Skill Analysis Phase: Alternate Approaches

Various additional alternate approaches and techniques relevant to the skill analysis phase are discussed in PCT/AU2016/000020. Those, and other techniques/approaches, are optionally used in the context of embodiments for media management as considered herein.

Example Downloadable Content Data Structures

In preferred embodiments, downloadable content includes the following three data types:
  (i) Data representative of sensor configuration instructions, also referred to as "sensor configuration data". This is data configured to cause configuration of a set of one or more PSUs to provide sensor data having specified attributes. For example, sensor configuration data includes instruction that cause a given PSU to: adopt an active/inactive state (and/or progress between those states in response to defined prompts); deliver sensor data from one or more of its constituent sensor components based on a defined protocol (for example a sampling rate and/or resolution). A given training program may include multiple sets of sensor configuration data, which are applied for respective exercises (or in response to in-program events which prompt particular forms of ODC monitoring). In some embodiments, multiple sets of sensor configuration data are defined to be respectively optimised for identifying particular ODCs in different arrangements of end-user hardware. For example, some arrangements of end user hardware may have additional PSUs, and/or more advanced PSUs. In preferred embodiments, sensor configuration data is defined thereby to optimise the data delivered by PSUs to increase efficiency in data processing when monitoring for ODCs. That is, where a particular element of content monitors for n particular ODCs, the sensor configuration data is defined to remove aspects of sensor data that is superfluous to identification of those ODCs.
  (ii) State engine data, which configures a performance analysis device for example a POD device) to process input data received from one or more of the set of connected sensors thereby to analyse a physical performance that is sensed by the one or more of the set of connected sensors. Importantly, this includes monitoring for a set of one or more ODCs that are relevant to the content being delivered. For example, content is driven by logic that is based upon observation of particular ODCs in data delivered by PSUs.
  (iii) User interface data, which configures the performance analysis device to perform skill/activity monitoring (via processing of MSD) based functionalities (such as reporting required for media monuments ad discussed herein), and optionally provide feedback and instructions to a user in response to the analysis of a physical performance (for example delivering of a curriculum including training program data). In some embodiments the user interface data is at least in part downloaded periodically from a web server.

The manner in which downloadable content is delivered to end user devices varies between embodiments, for instance based upon the nature of end user hardware devices, cloud-based data organisational frameworks, and so on. Various examples are described below.

In relation to sensor configuration data, the content data includes computer readable code that enables the POD device (or another device) to configure a set of PSUs to provide data in a defined manner which is optimised for that specific skill (or set of skills). This is relevant in the context of reducing the amount of processing that is performed at the POD device; the amount of data provided by sensors is reduced based on what is actually required to identify symptoms of a specific skill or skills that are being trained. For example, this may include:

Selectively (and in some cases dynamically) activating/deactivating one or more of the sensors.
Setting sampling rates for individual sensors.
Setting data transmission rates and/or data batching sequences for individual sensors.
Configuring a sensor to provide only a subset of data it collects.

Figure 11:
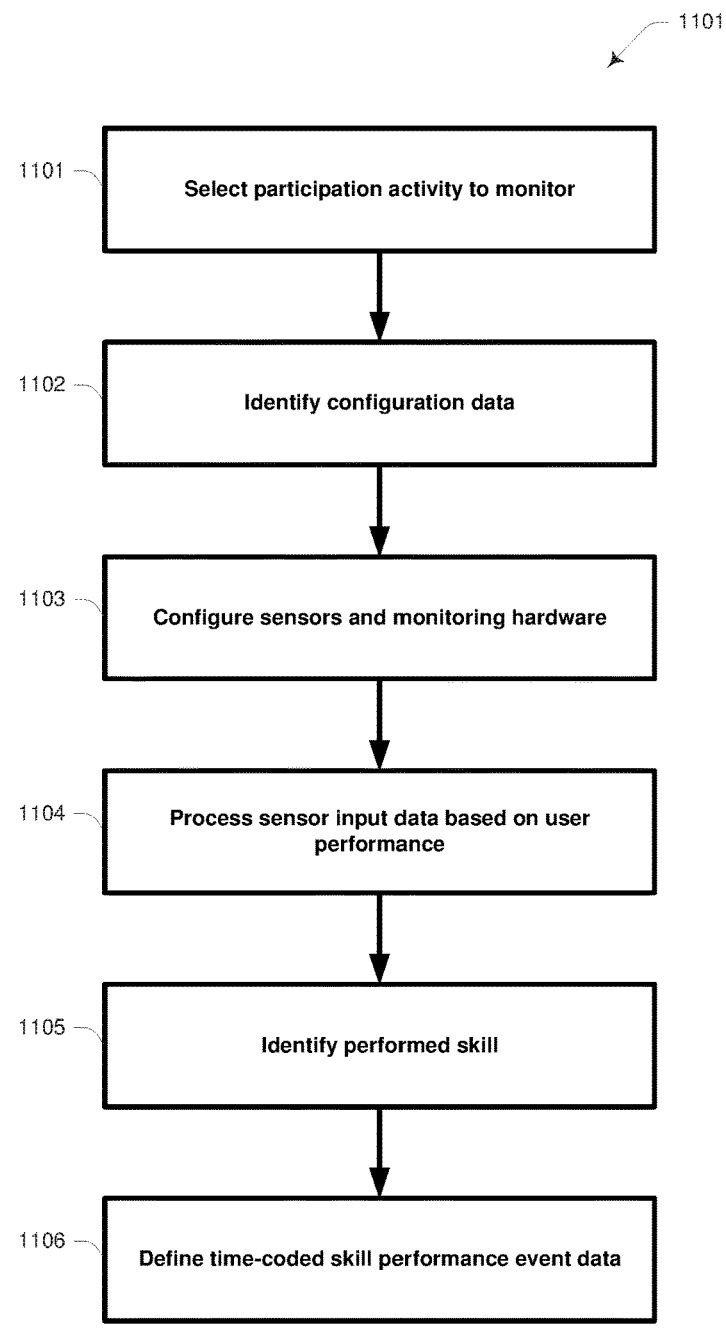
FIG. 11 an example operational method.

The POD device provides configuration instructions to the sensors based on a skill that is to be trained, and subsequently receives data from the sensor or sensors based on the applied configurations (see, by way of example, functional blocks 1101 and 1102 in FIG. 11A) so as to allow delivery of a PSU-driven training program.

The sensor configuration data in some cases includes various portions that loaded onto the POD device at different times. For example, the POD device may include a first set of such code (for example in its firmware) which is generic across all sensor configurations, which is supplemented by one or more additional sets of code (which may be downloaded concurrently or at different times) which in a graduated manner increase the specificity by which sensor configuration is implemented. For example, one approach is to have base-level instructions, instructions specific to a particular set of MSUs, and instructions specific to configuration of those MSUs for a specific skill that is being trained.

Sensors are preferably configured based on specific monitoring requirements for a skill in respect of which training content is delivered. This is in some cases specific to a specific motion-based skill that is being trained, or even to a specific attribute of a motion-based skill that is being trained.

In some embodiments, state engine data configures the POD device in respect of how to process data obtained from connected sensors (i.e. PSD) based on a given skill that is being trained. In some embodiments, each skill is associated with a set of ODCs (which are optionally each representative of symptoms), and the state engine data configures the POD device to process sensor data thereby to make objective determinations of a user's performance based on observation of particular ODCs. In some embodiments this includes identifying the presence of a particular ODC, and then determining that an associated symptom is present. In some cases this subsequently triggers secondary analysis to identify an ODC that is representative of one of a set of causes associated with that symptom. In other embodiments, the analysis includes determinations based on variations between (i) symptom model data determined from sensor data based on the user's performance; and (ii) predefined baseline symptom model data values. This is used, for example, to enable comparison of the user's performance in respect of each symptom with predefined characteristics.

User interface data in some embodiments includes data that is rendered thereby to provide graphical content that is rendered via a user interface. In some embodiments such data is maintained on the POD device (for example video data is streamed from the POD device to a user interface device, such as a smartphone or other display). In other embodiments data defining graphical content for rendering via the user interface is stored elsewhere, including (i) on a smartphone; or (ii) at a cloud-hosted location.

User interface data additionally includes data configured to cause execution of an adaptive training program. This includes logic/rules that are responsive to input including PSD (for example ODCs derived from MSD) and other factors (for example user attributes such as ability levels, learning style, and mental/physical state). In some embodiments, the download of such data enables operation in an offline mode, whereby no active Internet connection is required in order for a user to participate in a training program.

Example Content Delivery Methodologies

As noted, in some embodiments, content is made available to users via an online marketplace (for example an online marketplace delivered by a cloud hosted platform. A user accesses that marketplace (for example via a web browser application executing on a personal computer or mobile device), and obtains desired training content. Based on obtained content, the user configures a POD device to perform functionalities including functionalities relating to provision of training in respect of a desired activity and/or skill (for example by causing a server to download code directly to the POD device via the POD device's Internet connection, which may be to a local WiFi network). Based on this configuration, a set of training program rules are able to be executed on the POD device (or in further embodiments a secondary device coupled to the POD device) to provide an interactive training process. The interactive training process provides, to a user, feedback/instructions responsive to input representative of user performance. This input is derived from the PSUs, and processed by the POD device. The interactive training process is in some embodiments operated based on a set of complex rules, which take into consideration: (i) observed user performance attributes relative to predefined performance attributes; (ii) user attribute data, including historical performance data; (iii) a skill training progression pathway (which may be dynamic variable); and (iv) other factors.

The present disclosure focuses primarily on the example of a POD device that receives user performance data derived from a set of motion sensors (for example including wearable motion sensors coupled to garments; the motion sensors being configured to enable analysis of user body position variations in three dimensions). For example, this is particularly applicable to training in respect of physical activities, such as sports and other activities involving human movements. However, the technology is equally applicable in respect of data derived from other forms of sensor. Examples include sensors that monitor audio, video, position, humidity, temperature, pressure, and others. It will be appreciated that data from such sensors may be useful for skills training across a wide range of activity types. For example, audio sensors are particularly useful for training activities such as language skills, singing, and the playing of musical instruments.

At a general level, technology disclosed herein is in some embodiments configured to enable capture of wisdom of experts, and from this replicating the one-on-one conversation between coach and student. In this regard, features in some cases include:

Two way exchange. The digital technology is versatile and highly scalable and can be applied to virtually any skill or activity. Using sensors and associated technology, there is an ability to teach better with each interaction, adapting to individual users' style and physiology in a real-time coaching experience.

Real-time instruction. Sensors diagnose mistakes in movement and technique, and enable automated (and substantially instantaneous) delivery of personalised, tactile and/or audiovisual feedback and/or instructions.

Advanced performance. More than just tracking, users are constantly coached. A resulting measurable lift in performance helps a user hit milestones and reach your goals sooner with greater certainty.

How these features are achieved by various embodiments will be appreciated based on the description herein.

Skills training content is rendered via a user interface (for example in a graphical and/or audible form). As noted above, there are various technical arrangements by which this is achieved. A preferred approach is for training content to be downloaded directly to POD device 150, and rendered via a separate device that includes video and/or audio outputs which allow a user to experience rendered content. The separate device may include one or more of a mobile device such as a smartphone (which in some embodiments executes an application configured to render content provided by POD device 150), a headset, a set of glasses having an integrated display, a retinal display device, and other such user interface devices.

In some embodiments where a mobile device (such as a smartphone) is used, the POD device provides a local web server configured to deliver content to the mobile device. The mobile device executes a web browser application (or in some cases a proprietary app), which navigates to a web address in respect of which code is obtained from the POD device as a local web server.

Skills training content is in preferred embodiments obtained from an online marketplace. This marketplace preferably enables a user to select and procure various different skills training packages, and manage the downloading of those to the user's POD device (or POD devices). The term "skills training package" describes an obtainable set of skills training content. This may relate to a single skill, a variety of skills relating to a common activity, or various other arrangements. The present disclosure should not be limited by reference to any specific implementation option for structuring how skills training data is organised, made available for procurement, monetised, or the like.

Example Content Delivery Frameworks

The following section describes various exemplary technological frameworks for the delivery of content, such as adaptive skills training content which is driven by processing of PSD (such as MSD), to end user devices.

In overview, any one or more of the following approaches, or combinations thereof, may be used:

Browsing and selection of downloadable content via a first web-enabled device, with content download subsequently being effected to a second web-enabled device. For example, content is browsed via a smartphone, and then caused to be downloaded directly from a web source to a POD device.

Browsing and selection of downloadable content via a first web-enabled device, with content download subsequently being effected to that first web-enabled device. There may then be a secondary downloading of some or all of the content from the first web-enabled device to a second device, such as a POD device (for instance sensor configuration data and state engine data is first downloaded to a mobile device, and then delivered to a POD device).

Utilisation of a POD device that is separate from a user interface device. For example, a mobile device is used to provide a user interface, and a POD device is a processing unit mounted in a MSU-enabled garment.

Utilisation of a POD device that is integrated with a user interface device. For example, in some embodiments a smartphone takes the role of a POD device.

Utilisation of a POD device that is physically coupled to an existing end-user mobile device. For example, a POD device is defined as a processing unit which couples to a smartphone, for example via a cradle type mount.

Figure 9A:
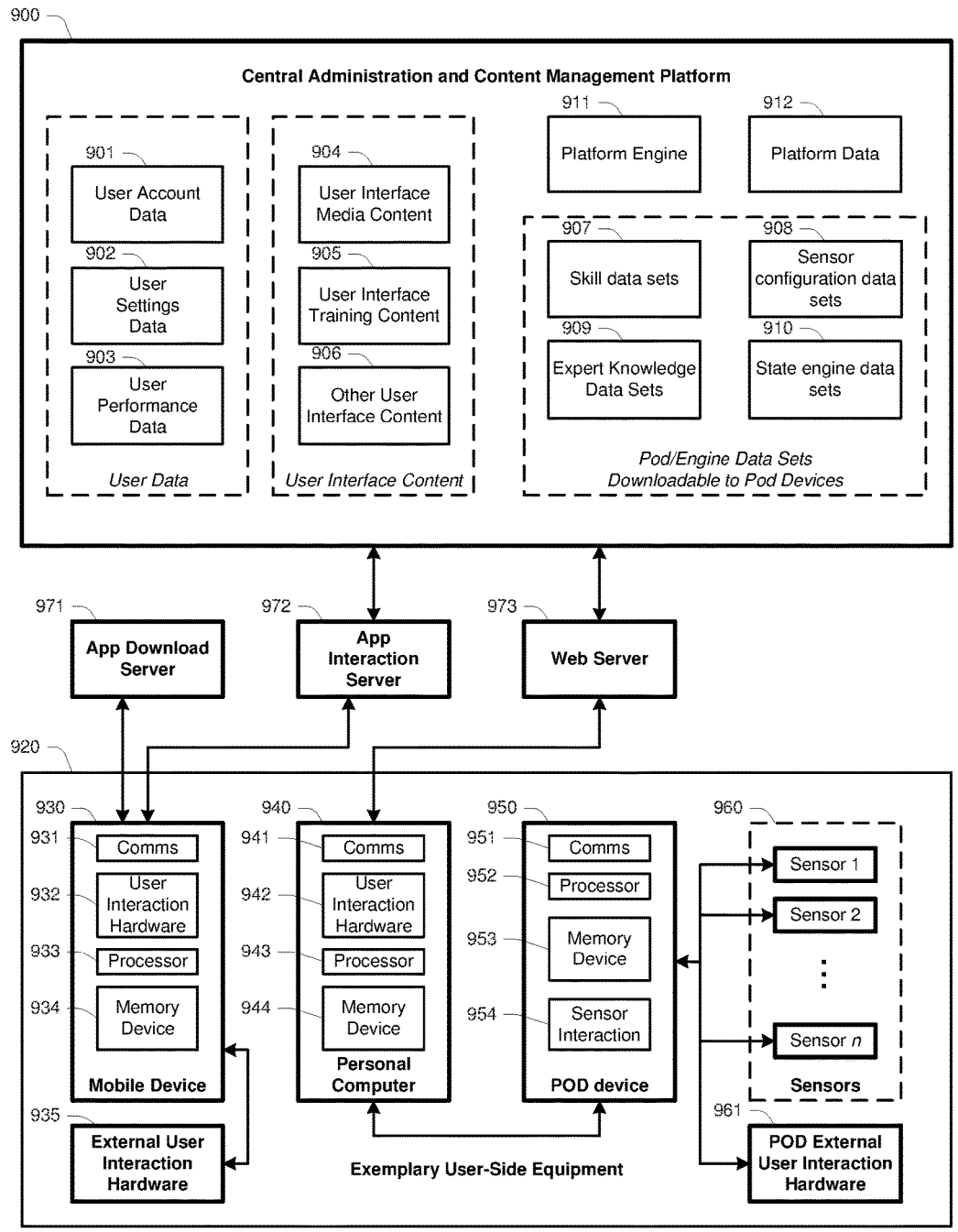
FIG. 9A illustrates an example framework including server-side and client-side components.
Figure 9B:
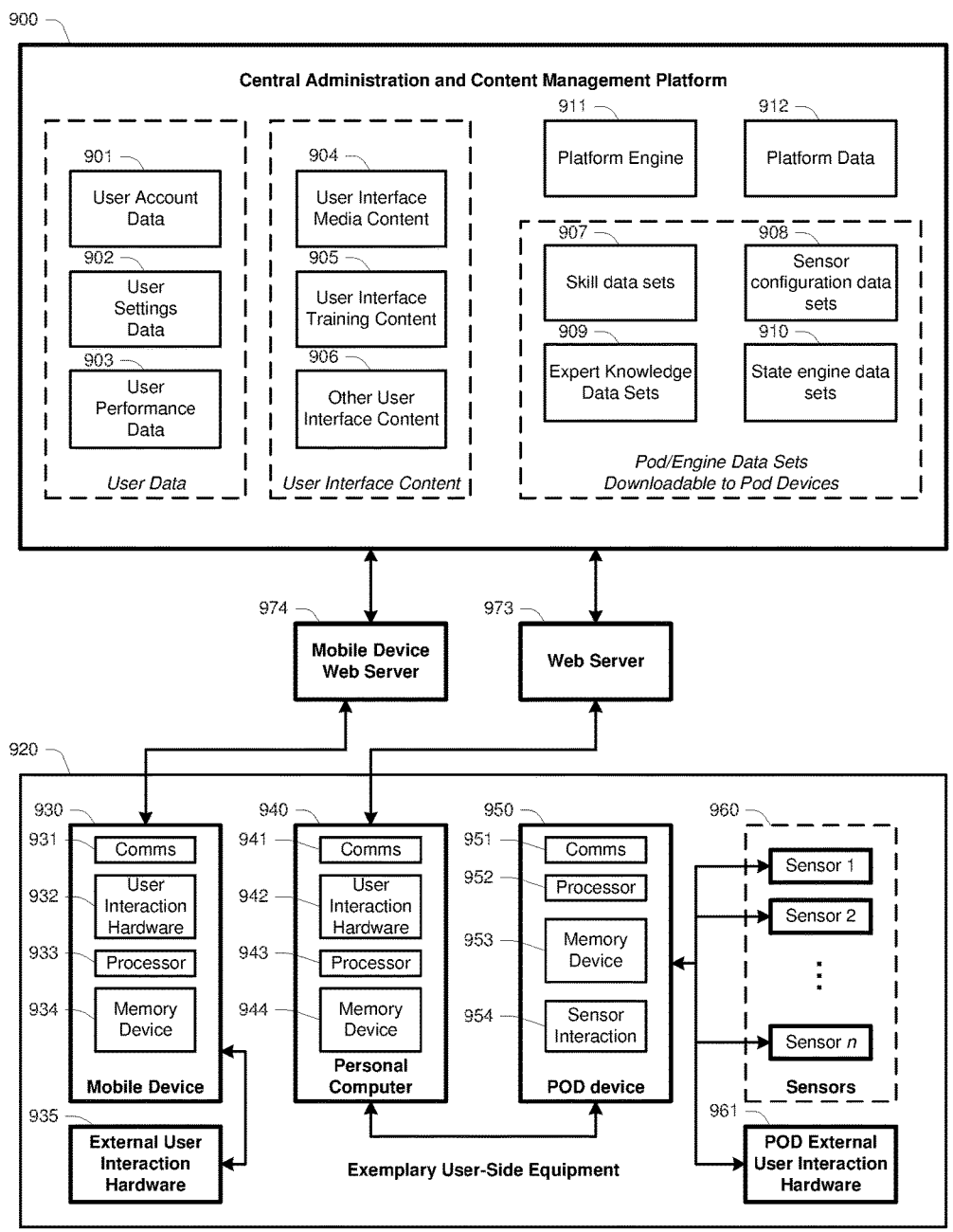
FIG. 9B illustrates a further example framework including server-side and client-side components.
Figure 9C:
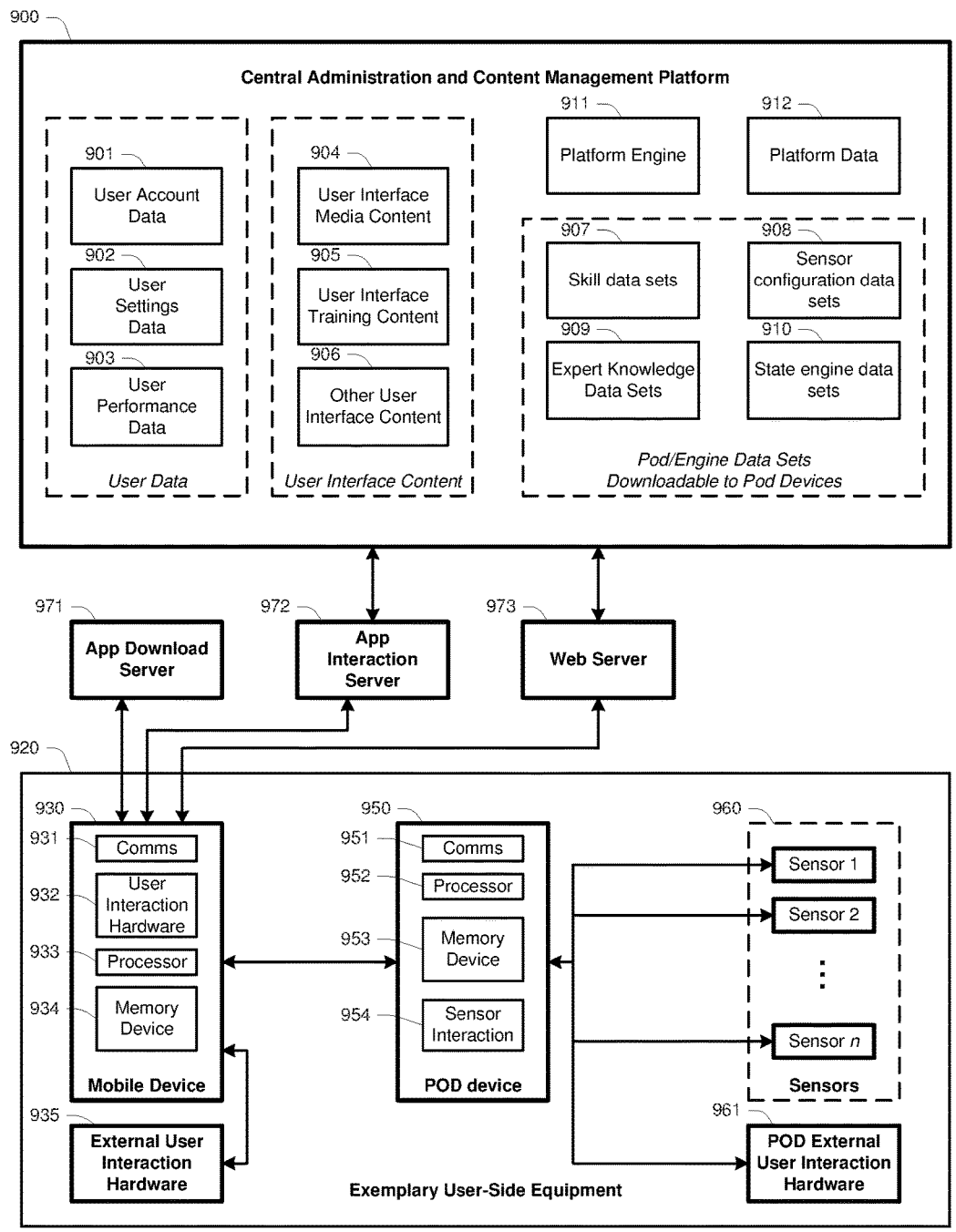
FIG. 9C illustrates a further example framework including server-side and client-side components.
Figure 9D:
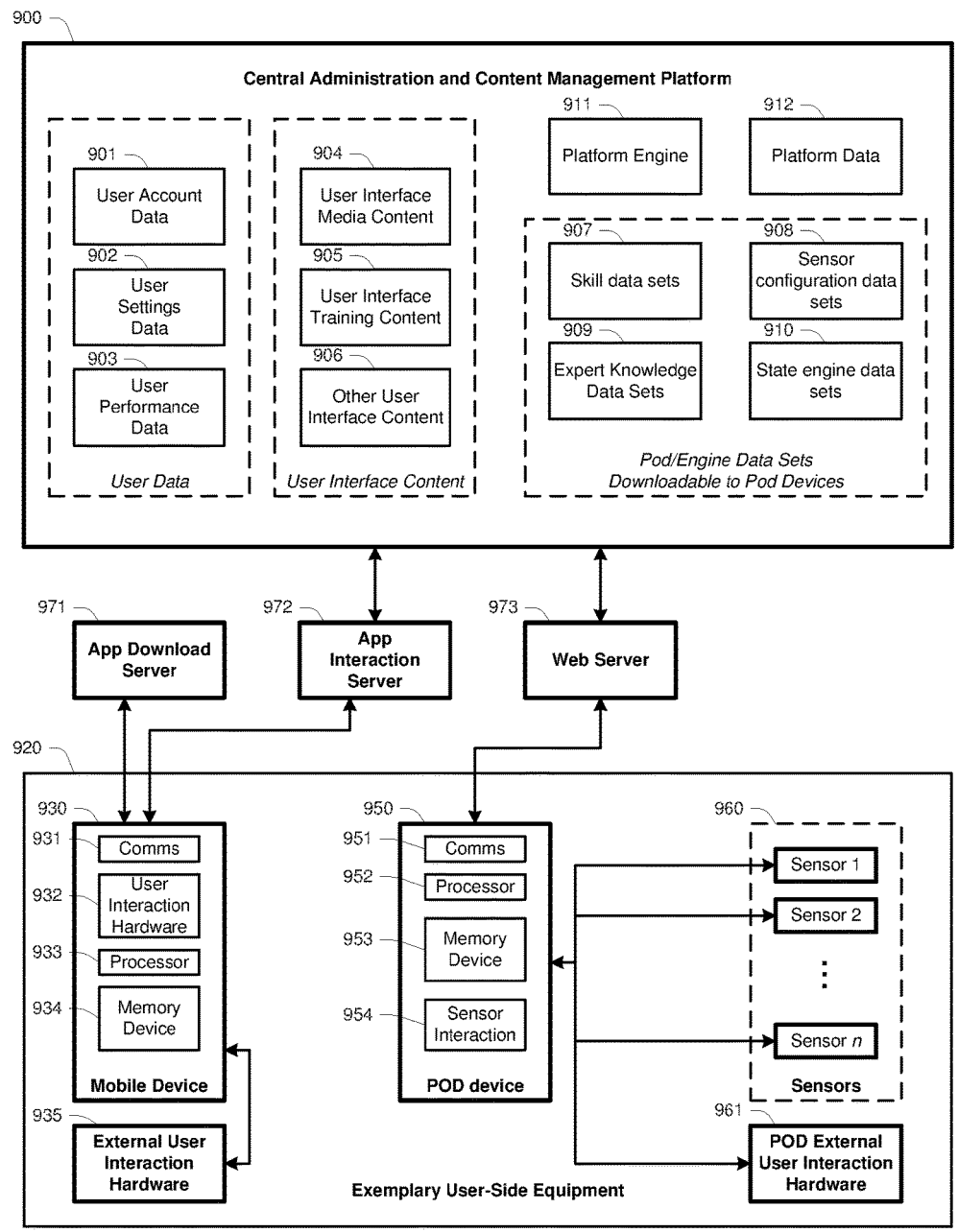
FIG. 9D illustrates a further example framework including server-side and client-side components.

FIG. 9A shows an exemplary computer implemented framework according to one embodiment. Various alternate embodiments are illustrated in FIG. 9B to FIG. 9D, where similar features have been designated corresponding reference numerals.

Each illustrated framework includes multiple computing devices (also referred to as "machines" or "terminals"), which are each configured to provide functionality (for example performance of "computer implemented methods") by executing computer-executable code (which may be stored on a computer-readable carrier medium) via one or more microprocessors (also referred to simply as "processors"). It will be appreciated that the various computing devices include a range of other hardware components, which are not specifically illustrated.

The example of FIG. 9A illustrates a central administration and content management platform 900. This platform is able to be defined by a single computing device (for example a server device), or more preferably by a plurality of networked computing devices. Components of a server are described functionally, without specific reference to various constituent computing devices that are configured to individually or collectively provide the relevant functionalities. It should be appreciated that such matters are an issue of design choice, with a wide range of network and server architectures being well known in the art. Furthermore, in some embodiments there are multiple instances of platform 900 operating in parallel.

Platform 900 is configured to provide functionalities that are accessed by a plurality of users (such as the subjects referred to above) via computing devices operated by those users. FIG. 9A illustrates a set of user-side equipment 920 operated in relation to an exemplary user. In practice, each of a plurality of users operates respective sets of similar equipment 920 (not shown).

Equipment 920 includes a mobile device 930. For example, in this embodiment mobile device 930 takes the form of a Smartphone. However, in other embodiments different mobile devices are used such as a tablet, a PDA, a portable gaming device, or the like. In some embodiments mobile device 930 is defined by purpose-configured hardware, specifically intended to provide functionalities relevant to the described overall framework. In overview, a primary function of mobile device 930 is to deliver, via a user interface, content that is obtained from platform 900. This content is able to be downloaded on an "as required" basis (in an online mode), downloaded in advance (thereby to enable operation in an offline mode), or both.

Mobile device 930 is able to be coupled to one or more pieces of external user interaction hardware, such as external headphones, microphones, a wearable device that provides a graphical display (for example glasses configured to provide augmented reality displays, retina projection displays), and so on.

In the example of FIG. 9A, mobile device 930 is configured to interact with platform 900 via a mobile app (for example an iOS or Android app), which is downloaded from an app download server 971. (In this embodiment server 971 is a third party operated server, although other embodiments make use of first party servers). Such a mobile app is stored on a memory device 934 and executed via a processor 933. The mobile app configures mobile device 930 to communicate with an app interaction server 972 via an available Internet connection, with app interaction server 972 in turn providing a gateway to data available via platform 900.

In the example of FIG. 9B, mobile device 930 is configured to interact with platform 900 via a web browser application, which upon navigation to a predefined web address configures mobile device 930 to communicate with a mobile device web server 974 via an available Internet connection. Web server 974, in turn, provides a gateway to data available via platform 900. The web browser application is executed based on code stored in memory 934 of mobile device 930, and provides a user interface specific to platform 900 via browser-renderable user interface code that is downloaded to device 930 via server 974.

Equipment 920 additionally includes a personal computer (PC) 940. This is able to be substantially any computing device that is correctly and adequately configured to enable a further hardware device, in the form of a POD device 950, to communicate with platform 900. For example, in one embodiment the POD device connects to PC 940 via a wired connection (such as a USB connection) or a wireless connection (such as a WiFi or a Bluetooth connection). Functionally, this allows downloading of data from platform 900 to POD device 950. Alternate arrangements and connections are able to be implemented thereby to enable communications between POD device 950, for example:

POD device 950 accessing platform 900 via mobile service 930, and a web server 973 (see FIG. 9C). This involves accessing specific functionalities of device 930 relevant to operation of POD device 950 or, in some embodiments, merely accessing an Internet connection provided through mobile device 930.

POD device 950 accessing platform 900 via web server 973 (see FIG. 9D).

In some such cases, for example where POD device 950 does not inherently provide a user interface, a given user operates mobile device 930 (or another suitable configured computing device) to access a user interface (for example via a mobile app or a web page), thereby to instruct platform 900 to deliver particular data to a POD device 950 associated with that user. In such an embodiment the data is directly downloaded to POD device 950 via an available Internet connection.

In some embodiments, skills training content to be rendered on mobile device 930 is first downloaded to POD device 950. This is implemented such that mobile device 930 is able to provide skills training data in an offline mode (with no Internet connection), with necessary content being provided by POD device 950. This is particularly relevant in examples where there is no mobile device 930, and the user interface is provided via a user interface delivery device 990 which communicates only with POD device 950 (for example a headset, set of glasses having an inbuilt display, retinal projection device, or the like).

Exemplary POD Device and Sensor Arrangements

POD device 950 is configured to perform processing of data collected from one or more PSUs 960. These PSUs are connected to POD 950 via wired and/or wireless connections. For example, in one embodiment a POD device is connected to a first set of PSUs via a direct wired coupling, and to a second set of PSUs via a RF-link to a bridging component, the bridging component in turn being connected to the second set of PSUs via a direct wired coupling.

A range of PSUs are used across various embodiments depending upon the nature of the data being collected. In turn, the nature of the data being collected is dependent upon the skill or activity being undertaken by the user. For instance, the following user cases are relevant to a number of examples and embodiments considered herein:

Wearable MSUs. MSUs are integrated into clothing articles (MSU-enabled garments) that are configured to be worn by a subject. Examples of such clothing articles include compression-type clothing (such as a shirt or pants) which each includes a plurality of spaced apart MSUs at known positions. In some cases the clothing includes preformed mounting locations for releasably receiving respective MSUs to enable movement of MSUs between the available mounting locations. In one embodiment, a compression shirt supports a plurality of motion MSUs and has a mounting to complementarily releasably receive a POD device, such that the mounting couples the POD device to the MSUs via wired connections that extend through and which are enveloped by the shirt. The shirt is able to be coupled with a complementary set of compression pants that include further plurality of motion MSUs which are wired to a common RF communication module. That RF communication module communicates MSD to a further RF module provided on the shirt, or by the POD device, thereby to enable the POD device to receive data from all MSUs on the shirt and pants.

ASUs. In different embodiments different audio sensors are used. Examples of available sensors include microphone-based sensors, sensors that plug into audio input ports (for example via 2.5 mm or 3.5 mm jack connectors), thereby to receive audio signals, pickups that generate MIDI signals, and so on.

It will be appreciated that POD device 950 is able to be configured via software to process data from substantially any form of PSU that provides an output signal (for example a digital output signal) that is received by the POD device.

Some embodiments provide multiple different hardware configurations of POD devices, each being manufactured to interact with specific PSUs. For example, exemplary POD devices may include:

A POD device configured to be carried by a garment, which physically couples to a plurality of MSUs also carried by that garment (and in some cases wirelessly couples, directly or indirectly, to one or more further MSUs).

A POD device that includes a microphone.

A POD device that includes an audio input port (such as a 3.5 mm headphone jack).

It will additionally be appreciated that the various forms of PSU allow for training in respect of a wide range of skills. For example, a POD device coupled to one or more ASUs is in some cases used to provide training in various musical skills (for example singing, playing of instruments, and the like).

Example Arrangements for Delivery of User Interface

The manner by which the user interface provides feedback and/or instructions varies based on hardware configurations. In some embodiments the user interface is audio-only (for example using headphones), in which case instructions and feedback are audio-based. In some embodiments the user interface includes visual information, which requires a display screen (for example a display screen provided by a smartphone device, appropriate glasses and/or retinal display devices, and so on).

Figure 10A:
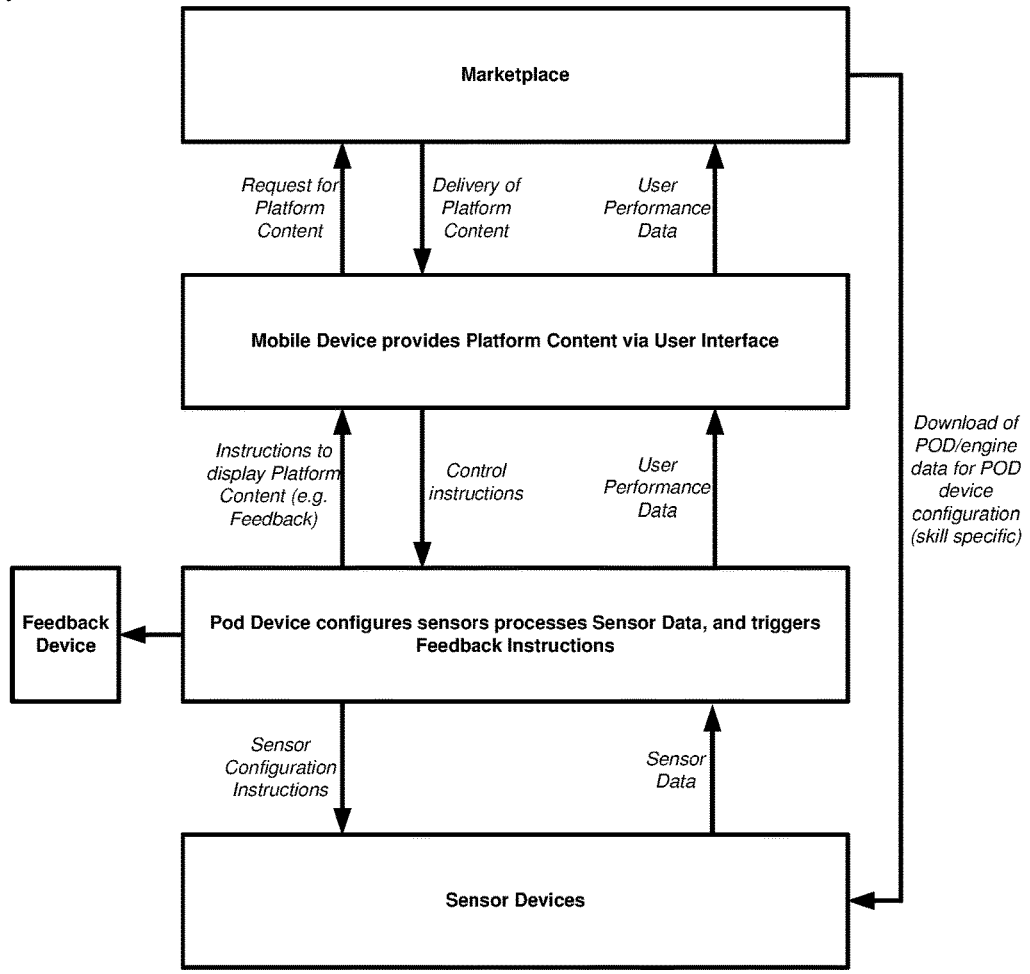
FIG. 10A illustrates operation of an example framework.

The arrangement of user-side equipment in FIG. 9A is able to be configured to function as shown in FIG. 10A. More particularly, a marketplace platform is technically configured for delivering POD/engine data to a POD device to, in turn, allow configuration of the POD device to deliver training content in respect of a specific skill (or set of skills). The POD device is configured to process received data from the sensors based on POD/engine data that was previously downloaded from the marketplace. Based on this processing, the POD device provides instructions to a mobile device to display platform content via its user interface (for example thereby to provide feedback, instruct the user to perform a specific task, and so on). The mobile device downloads platform content, where relevant, from the platform.

A further feedback device is used in other embodiments (for example an audio device, glasses with digital displays, and so on), and in FIG. 10A this is illustrated as being directly coupled to the POD device.

Figure 10B:
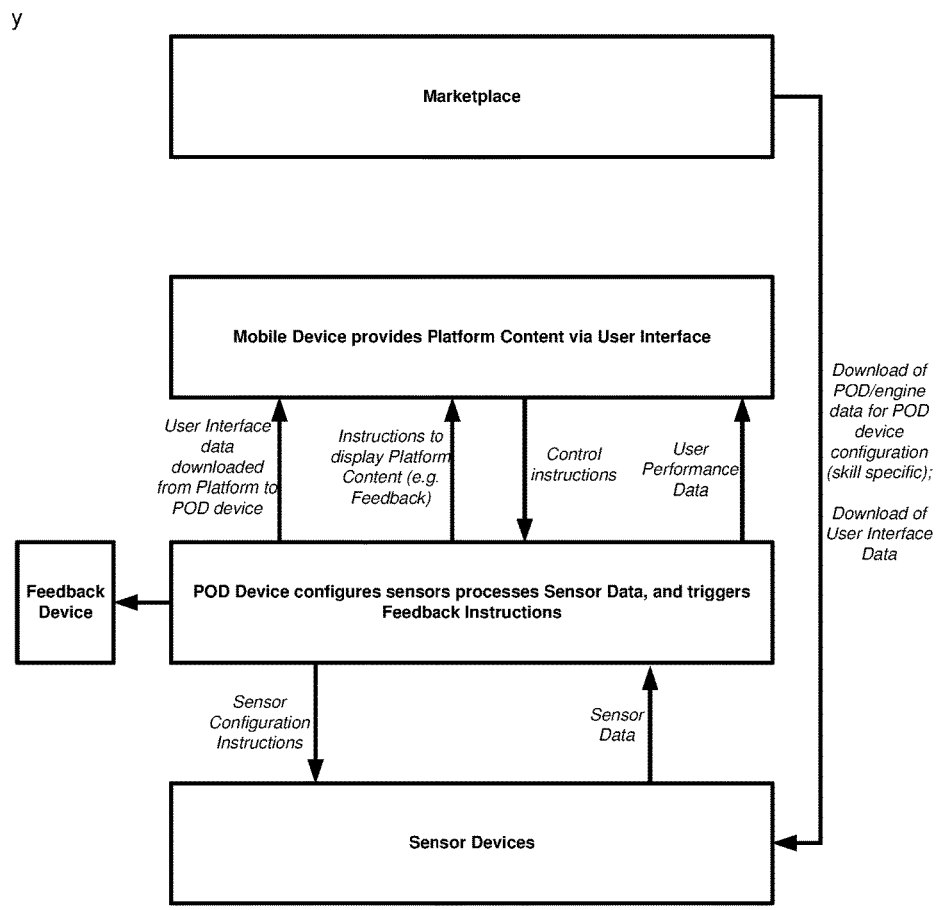
FIG. 10B illustrates operation of a further example framework.
Figure 10C:
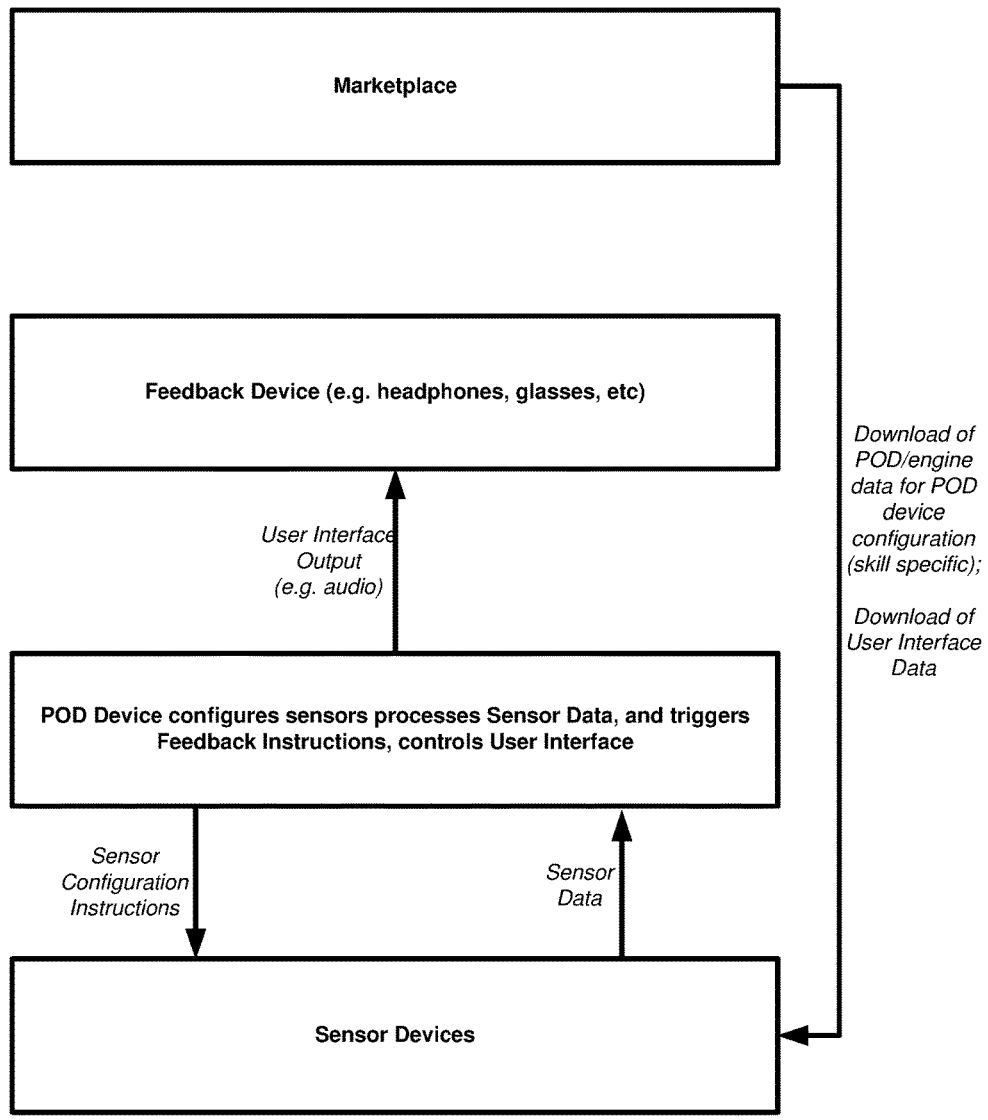
FIG. 10C illustrates operation of a further example framework.

FIG. 10B illustrates an alternate arrangement whereby the mobile device operates in an offline mode. In this example, user interface data is downloaded to the POD device, and provided to the mobile device via the POD device. A further alternate arrangement is illustrated in FIG. 10C, where there is no mobile device, and the POD device provides feedback/instructions directly via a feedback device (such as headphones, glasses with a screen, a retina projection device, or another feedback device).

Example End-User Hardware Arrangements Incorporating MSUs

Described below are various hardware configurations implemented in embodiments there to enable monitoring of an end-user's attempted performance of a given skill, which includes identification of predefined observable data conditions (for example observable data conditions defined by way of methodologies described above) in sensor data collected during that attempted performance.

It should be appreciated that: (i) these are examples only, and technology disclosed herein may be implemented via alternate hardware arrangements; (ii) provided diagrams are schematic and not to scale; and (iii) the diagrams provide functional representations showing key components, and do not represent aspects of PCB design, sensor unit positioning, connective wiring, and the like.

Various embodiments provide a wearable garment. For example, these may include any one or more of: bodysuits, shirts (short or long sleeve), pants (short or long), gloves, footwear, hats, and so on. In some cases a wearable garment is defined by multiple separable garment items (for example a shirt and pants) which are configured to communicate with one another (for example via wired couplings or wireless communication). The garments are preferably manufactured from resilient materials, for example as compression garments. This assists in maintaining sensor components stationary relative to a wearer's body. The garments are preferably manufactured to enable removal of electrical components (such as sensor units and a POD device), for example to enable maintenance or the like.

The garments include a plurality of sensor strands, each sensor strand including one or more sensor units. The sensor strands each commence from sensor strand connection port 1208, wherein the sensor strand connection port is configured to couple a plurality of sensor strands to a central processing device, which is referred to as a POD device in a manner consistent to disclosure further above. The sensor strands may include a single sensor unit, or multiple sensor units.

Where a sensor strand includes multiple sensor units, they are preferably connected in-line. That is, where a strand includes n sensor units $SU_1 \ldots SU_n$, a communication addressed to a sensor unit $Su_i$ is received by and re-transmitted by each of $SU_1 \ldots SU_{i-1}$. Various addressing protocols may be used, however these are configured such that communications are addressed based on sensor unit mounting locations. This allows sensor units to be installed without a need to ensure a given specific sensor unit is installed at a specific mounting location (which is particularly useful if sensor units are removed for garment washing), and also allows swapping out of sensor units (for example in the case of a fault).

In some cases addressing protocols are in part based on identifiers associated with individual sensor units, in which case the POD device performs an auto-configuration step upon recognising a sensor unit thereby to identify the mounting location at which that sensor unit is installed and associate the sensor's identifier with that mounting location. In some embodiments, addressing is achieved by techniques that do not require knowledge of sensor identifiers, such as including a retransmission count in messages (for example a message includes a retransmission integer set by the POD device, which is decremented upon each transmission, and the message received and processed by a sensor unit in the case that the decrementing count reaches zero). The latter approach has some advantages in allowing sensor units to be exchanged/replaced without a need for subsequent reconfiguration of addressing parameters at the POD device.

In a preferred embodiment, each sensor unit includes a circuit board component mounted within a sealed container. The sealed container includes two connection ports; one for upstream communication along the sensor strand, one for downstream communication along the sensor strand. In some embodiments the sensor unit is able to identify an installed orientation, such that which of the ports is the upstream and downstream port determined based on installation orientation. In other embodiments there is a predefined installation orientation such that the sensor unit is not able to be installed in reverse. The connection ports are preferably configured for a snap-locking mounting to complementary connection ports on the sensor strands, such that a physically observable coupling correspondingly provides electronic/communicative coupling.

The sensor strands include connecting lines, including one or more lines for communication, and one or more lines for power supply (with power for sensor units being provided by the POD device). The connecting lines are sealed, such that submersion of the garment in water (for example during cleaning) does not cause damage to the lines. Preferably, connector modules that provide connection of the POD device and sensor units to the connecting lines provide watertight seals. Furthermore, in preferred embodiments, when the POD device and sensor units are installed on the garment, all electrical components are provided in a waterproof or water resistant configuration (for example snap-locking engagement of POD device and sensor unit connection ports to sensor strand connection ports provides watertight or water resistant sealing).

On a given sensor strand including a proximal sensor unit and one or more downstream sensor units, the proximal sensor unit is configured to (i) relay, in a downstream direction, sensor instructions provided by the central processing unit and addressed to one or more of the downstream sensor units; and (ii) relay, in an upstream direction, sensor data provided by a given one of the downstream sensor units to the central processing unit. This may include an activation/deactivation instruction. The sensor instruction also include sensor configuration data, wherein the sensor configuration data configures the sensor unit to provide sensor data in a defined manner. The sensor configuration data is in some cases defined by reference to sampling rates, monitoring a reduced selection of information observable by the sensor components, and other configuration attributes defined specifically for a skill that is being observed by the POD device.

Each sensor unit includes (i) a microprocessor; (ii) a memory module; and (iii) a set of one or more motion sensor components. More detailed disclosure of exemplary sensor hardware is provided further below. However, these basic components enable a sensor component to receive communications from a POD device, and provide observed data from the sensor components in a predefined manner (for example defined by reference to resolution, sample rates, and so on). In some embodiments each sensor unit includes a local power supply, however it is preferably that power is supplied along the sensor strands from the POD device (or another central power supply) rather than requiring individualised charging of sensor unit batteries or the like.

For an exemplary sensor unit, the set of one or more sensor components includes one or more of: (i) a gyroscope; (ii) a magnetometer; and (iii) an accelerometer. In preferred embodiments described below there is one of each of these components, and each is configured to provide three-axis sensitivity. In further embodiments there are multiple components of one or more of the components types, for example two accelerometers. This enables differing configurations, for example such that one is configured to observe course movements at a given resolution, and the other to observe specific fine movements at higher resolution.

The central processing device (POD device) includes (i) a power supply; (ii) a microprocessor; and (iii) a memory module. The memory module is configured to store software instructions executable by the microprocessor that enable the processing device to perform various functionalities, including configuration of sensor units to transmit sensor data in a predefined manner and to identify one or more sets of predefined observable data conditions in sensor data, including sensor data received by the central processing device from the plurality of connected sensor units. In a preferred embodiment the POD device also includes sensor components (for example the same sensor components as a sensor unit) thereby to enable motion observation at the position of the POD device. In some embodiments the POD device is mounted to the garment in a pouch provided in a location that, in use, is proximal the uppercentre of a user's back (for example between shoulder blades).

Figure 12A:
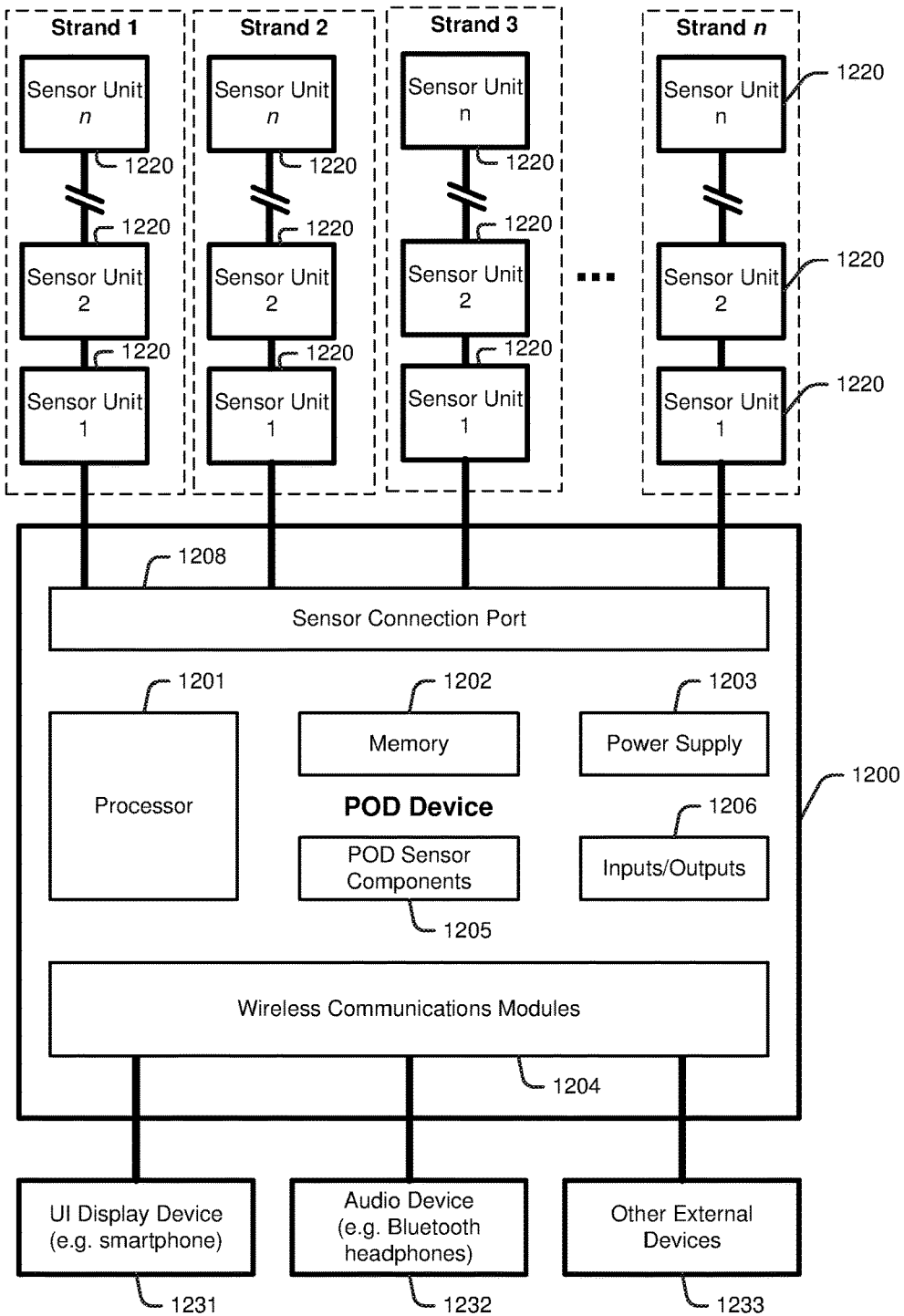
FIG. 12A illustrates performance analysis equipment according to one embodiment.

FIG. 12A illustrates a selection of hardware components of a wearable garment according to one embodiment. It will be appreciated that these are illustrated without reference to geometric/spatial configurations resulting from configuration of the garment itself.

The POD device 1200 of FIG. 12A includes a processor 1201 coupled to a memory module 1202, the memory module being configured to store software instructions thereby to provide functionalities described herein. These include:

Data representative of a training program (or multiple training programs), including logic for progressing through the training program, and user interface data that communicated externally of the POD device rendered by other components (such as a headset, display device, and so on).

For the (or each) training program, a plurality of skills that are to be trained. Each skill is defined by data including sensor configuration instructions, rules for identifying observable data conditions in sensor data, and rules relating to feedback (and/or other actions) that are when particular observable data conditions are identified.

It will be appreciated that various other aspects of software instructions are also provided.

A rechargeable power supply 1203 provides power to POD device 1200, and to one or more connected devices (including sensor units and, where provided, one or more control units). Local sensor components 1205 (for example three-axis magnetometer, three-axis accelerometer, and three-axis gyroscope) enable the POD device to function as a sensor unit. Inputs/outputs 1206 are also provided, and these may include the likes of: power/reset buttons; lights configured to display operational characteristics; and in some embodiments a display screen. However, in embodiments herein described the primary modes of communications between the POD device and a user are by external (and self-powered) user interface devices.

POD device 1200 includes one or more wireless communications modules 1204, thereby to enable communications/interactions with one or more remote devices. For example, the communications modules may include any one or more of the following:

WiFi. For example, WiFi is in some embodiments used to deliver user interface content (including image, text, audio and video data) for rendering at a UI display device 1231. This may include a smartphone, tablet, device with heads-up-display (such as an augmented reality headset or eyewear), and other such devices. The UI display device may be used to select and/or navigate training content available to be delivered via the POD device.

Bluetooth. For example, Bluetooth is in some embodiments used to deliver renderable audio data to a Bluetooth headset or the like, thereby to provide audible instructions/feedback to a user.

ANT+ (or other such communications modules) configured to enable interaction with monitoring devices, such as heart rate monitors and the like.

RF communications modules. In some embodiments one or more such modules are provided thereby to enable communication with wireless sensor units, for example sensor units that are configured to be attached to equipment (such as a skateboard, gold club, and so on). In some cases this includes a wireless sensor strand, defined by a plurality of wired sensor units connected to a common hub that wirelessly communicates with the POD device.

There may be various other wireless communication modules for various other external devices 1233.

The POD device includes a circuit board, and optionally additional hardware components, provided in a sealed or sealable container (water proof or water resistant). This container is able to be mounted to the garment (or example in a specifically configured pouch), and that mounting includes connection of one or more couplings. Preferably, a single coupling connects the POD device to all available sensor strands. Again, this may be a snap-lock coupling (water proof or water resistant), which provides both physical and electronic coupling substantially simultaneously.

FIG. 12A illustrates multiple sensor strands (Strand 1 . . . Strand n) coupled to a sensor connection port 1208. Each sensor strand includes a plurality of sensor units (Sensor Unit 1 . . . Sensor Unit n), however it should be appreciated that in some embodiments a given strand includes only a single sensor unit.

Figure 12B:
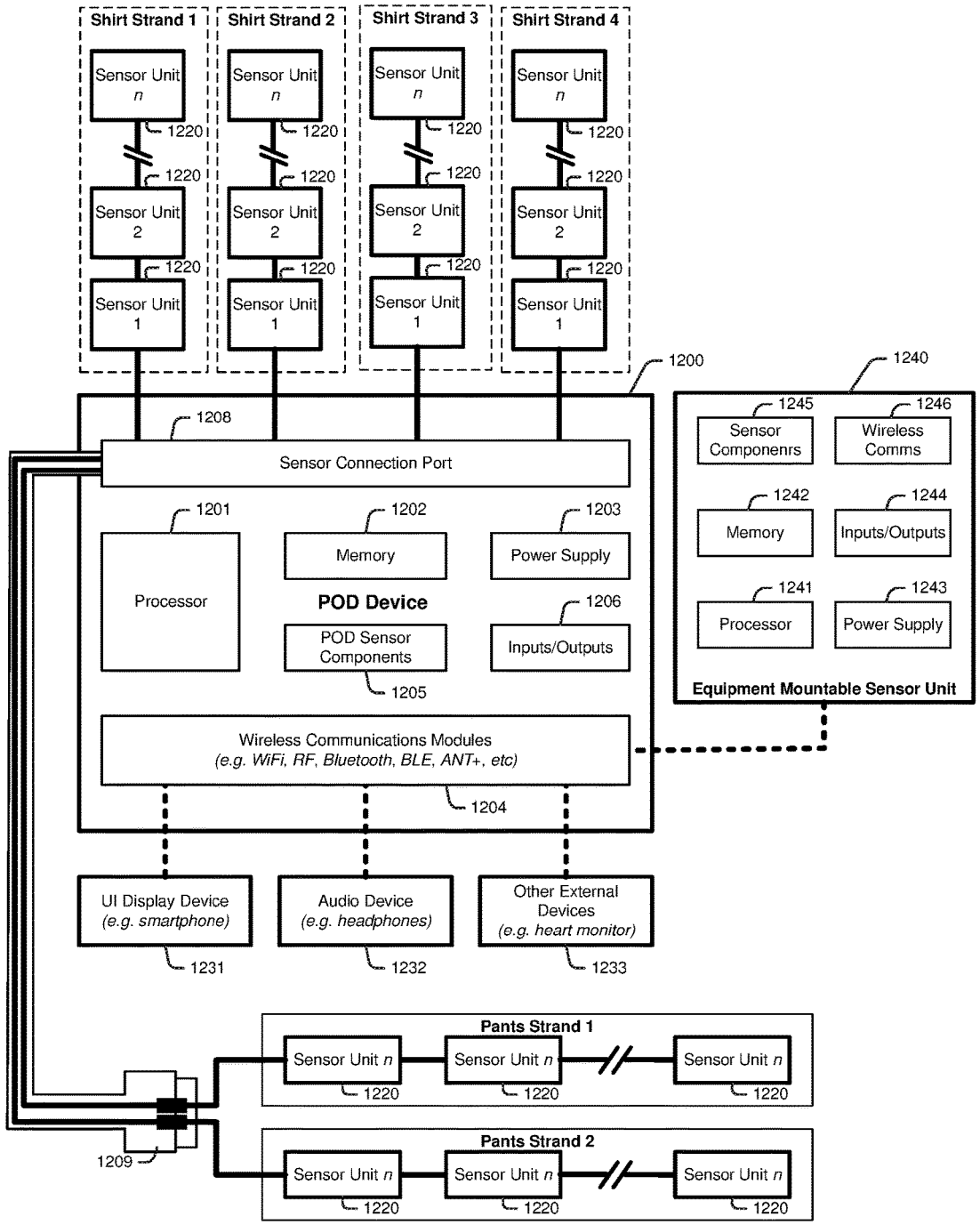
FIG. 12B illustrates performance analysis equipment according to one embodiment.

FIG. 12B illustrates an alternate arrangement of sensor strands. As context, some embodiments provide garments configured with one or more "partial" sensor strands. Each partial sensor strand includes (i) none or more sensors units; and (ii) a connector module that is configured to couple to a complementary connector module provided by a secondary garment. The phrase "none or more" indicates that in some cases a partial sensor strand is defined by a sensor strand line connecting the POD device to a connector module without any intervening sensor units, and on other cases partial sensor strand is defined by a sensor strand line on which one or more sensor units are provided, the strand terminating at a connector module.

Coupling of the connector module to the complementary connector module provided by a secondary garment functionally connects one or more of the partial sensor strands to a corresponding one or more secondary garment partial sensor strands, thereby to enable communication between (i) one or more sensor units provided on the one or more secondary garment partial sensor strands; and (ii) the central processing device.

In the example of FIG. 12B, a garment includes a shirt and pants. There are four shirt sensor strands, and two pants sensor strands. A connector arrangement 1209 couples partial pants strands thereby to enable communication between the sensor units provided on the pants, and the pod device (and powering of those sensor units by the POD device). In further embodiments this sort of arrangement is used to enable connection to sensor units provided on footwear, handwear, headwear, and so on. For example, in some embodiments connector ports are provided proximal arm, neck and foot apertures thereby to enable elongation of a provided sensor strand by one or more further sensor units carried by a further garment item or device.

In some embodiments, sensors carried by secondary garments, such as handwear or footwear, include specialist sensor components that measure attributes other than motion. For example, pressure sensor components may be used (for example thereby to measure grip strength on a gold club, to measure force being applied to the ground or another object, and so on). The POD device is configured to know, for a given training program, the sensor arrangement that is to be provided. For example, a user is provided instructions in terms of the sensor units that should be connected, and the POD device performs a check to ensure that sensors are responding, and expected sensor data is being provided.

FIG. 12B also illustrates an equipment mountable sensor unit 1240. This unit includes a processor 1241, memory 1242 and sensor components 1245 substantially in the same manner as does a sensor unit 1220. However, it additionally includes a wireless communications module 1246, thereby to enable wireless communications (for example RF communication) with POD device 1200, and a local power supply 1243. Inputs/outputs (such as lights, power/reset buttons, and the like) are also provided.

Figure 12C:
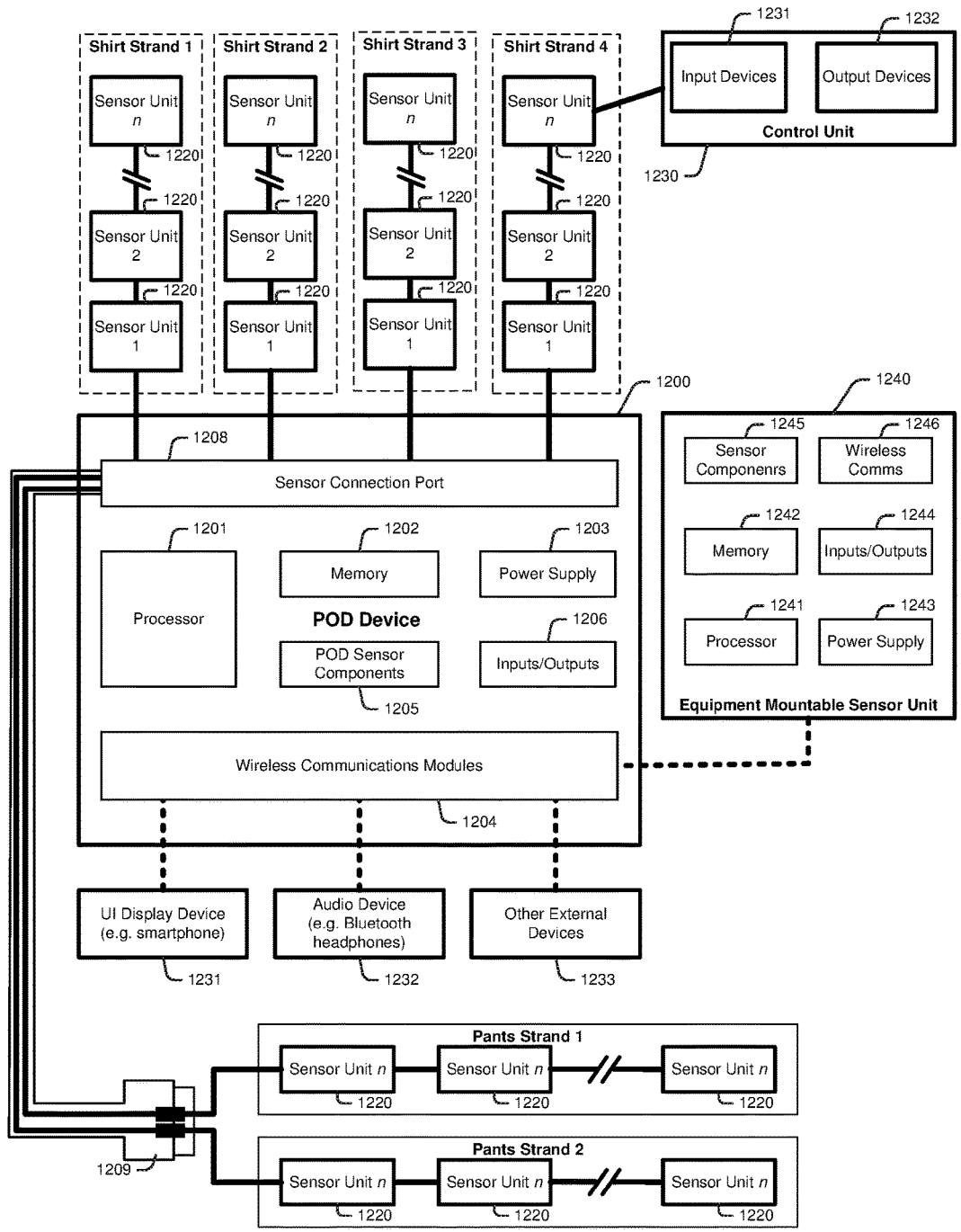
FIG. 12C illustrates performance analysis equipment according to one embodiment.

FIG. 12C expands on FIG. 12B by providing a control unit 1230. This control unit is physically coupled to the distal end of one of the shirt strands, for example as a wrist-mounted control unit. In some embodiments the control unit is integrated with a sensor unit. Control unit 1230 includes input devices 1231, such as one or more buttons, and output devices 1232, such as one or more lights and/or a display screen (preferably a low-power screen). Control unit 1230 is provided to assist a user in providing basic commands to control the provision of training content via the POD device. For example, commands may include "previous" and "next", for example to repeat a previous audible instruction, or skip forward to a next stage in a training curriculum. In some embodiments audible content is provided to assist a user in operating the input devices, for example by audibly providing selectable menu items.

Figure 12D:
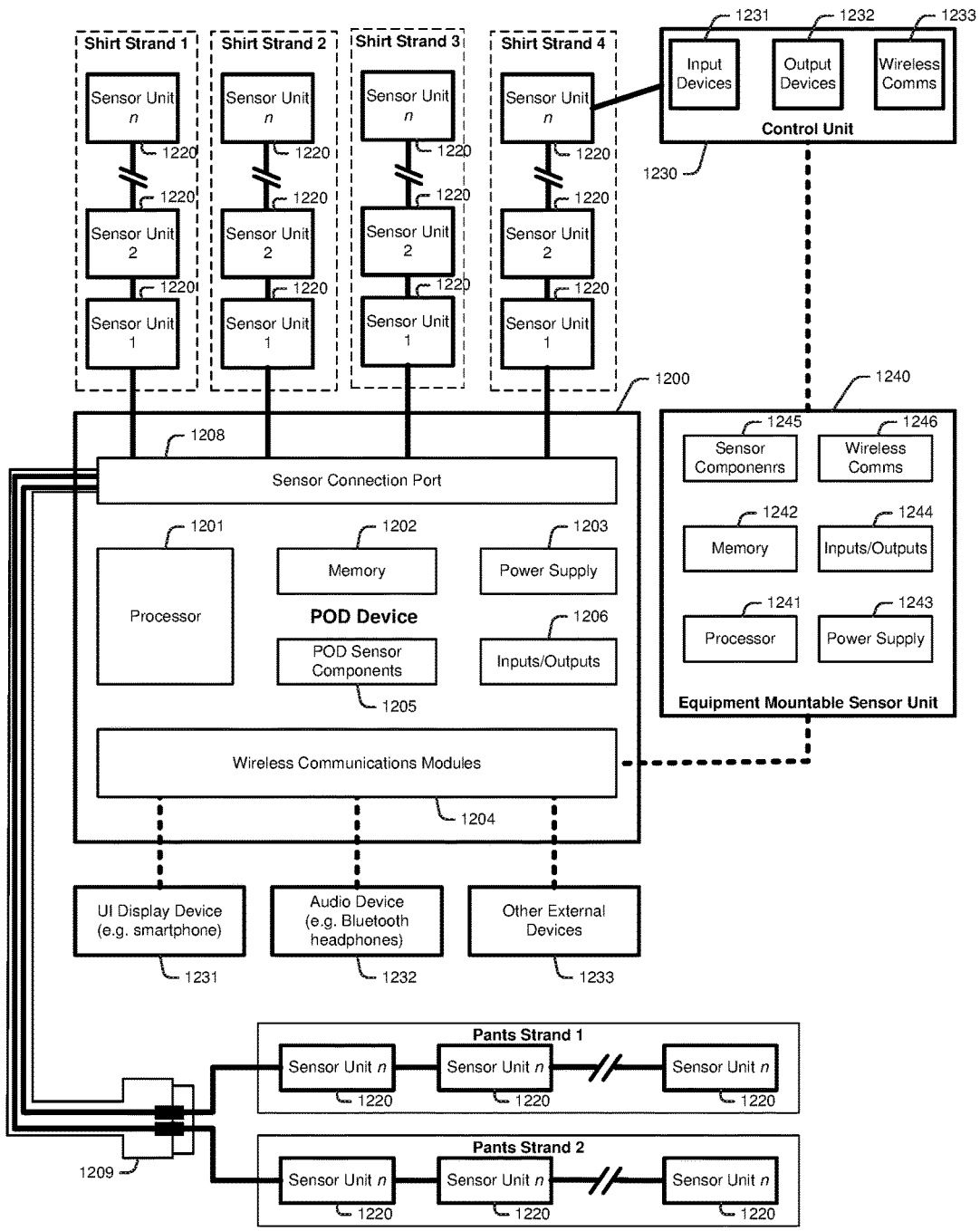
FIG. 12D illustrates performance analysis equipment according to one embodiment.

In the embodiment of FIG. 12D, control unit 1230 additionally includes a wireless communications module (for example RF) configured to receive wireless signals provided by equipment mountable sensor unit 1240. In this manner, wireless sensor unit data is able to be received both at the POD device directly (via modules 1204) and indirectly (via module 1233, via control unit 1230 and along a sensor strand, in this case being shirt sensor strand 4). This provides redundancy for the wireless communications; it should be appreciated that there can be challenges in reliably receiving wireless communications where signals pass through a human body (which is predominately water). Having two spaced apart locations (either as shown in FIG. 12D, or via an alternate arrangement), there is a significantly increased chance that all sensor data from unit 1240 will be received and made available for analysis. The POD device implements a data integrity protocol thereby to determine how to combine/select data provided by each of the two pathways. In some embodiments, for example where there is greater reliance of external sensor units, there may be multiple redundant wireless communications units positioned at various locations on the garment.

In some embodiments unit 1230 is provided on its own strand, rather than on a sensor strand which might otherwise include a terminal connector for attachment of a sensor-enabled handwear component.

Figure 12E:
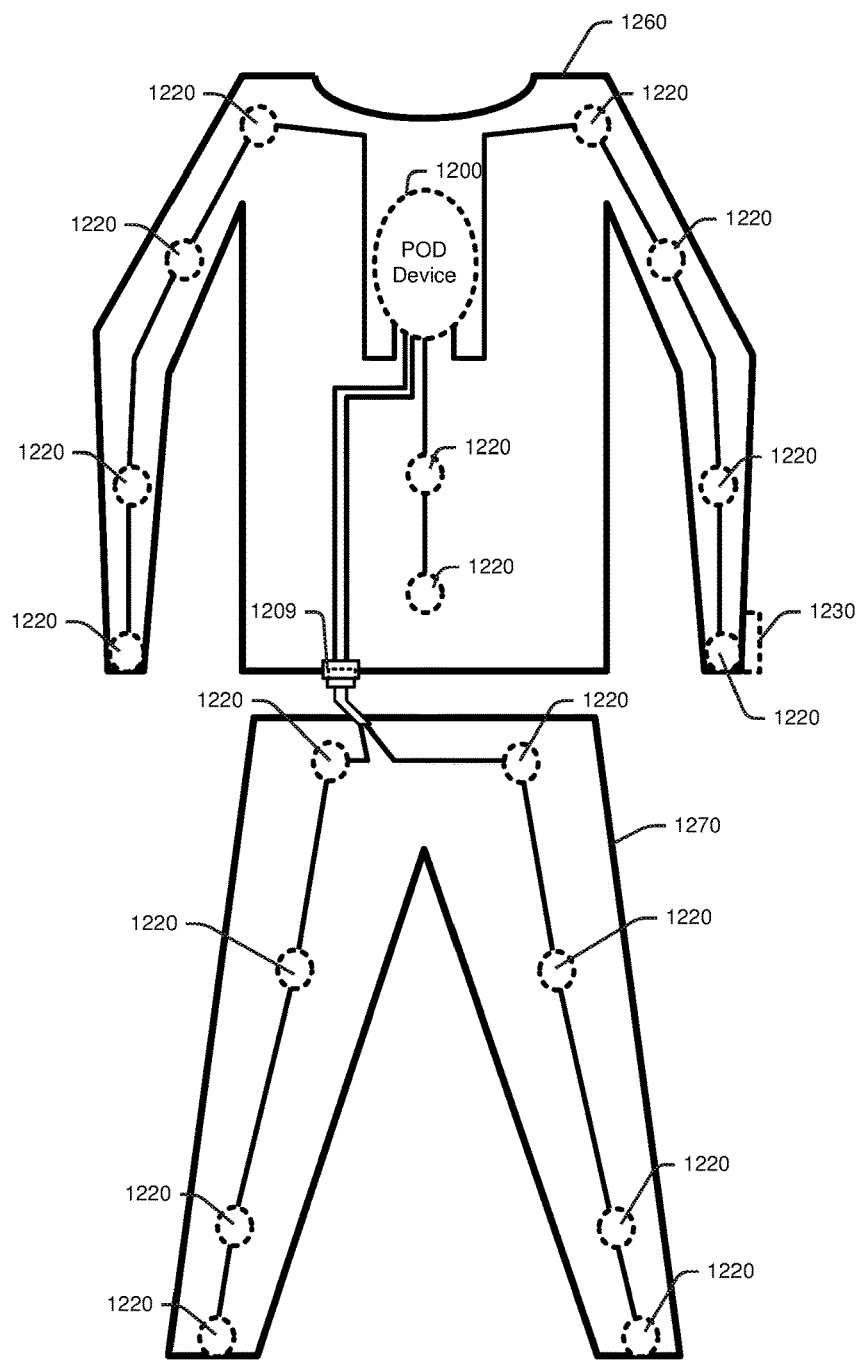
FIG. 12E illustrates a MSU-enabled garment arrangement according to one embodiment.

FIG. 12E provides a schematic representation (not to scale) of a two-piece garment according to one embodiment. This is labelled with reference numerals corresponding to previous figures. The illustrated garment is a two-piece garment, being defined by three sensor strands on the shirt component, and two sensor strands which provide sensor units on the pants component (with a connector 1209 coupling sensor strands between the garment components).

The illustrated positioning of sensor units is by no means intended to be limiting, and instead provides a rough guide as to potential sensor unit locations for a garment having this number of sensor units. A general principle illustrated in FIG. 12E is to provide sensors away from joints. Data collected from the respective sensor units' gyroscopes, accelerometers and magnetometers enables processing thereby to determine relative sensor locations, angles, movements and so on across multiple axis (noting that providing three 3-axis sensors in effect provides nine degrees of sensitivity for each sensor unit). Rich data relating to body movement is hence able to be determined. Furthermore, by way of configuration data provided by the POD device, the sensitivity/operation of each sensor is able to be selectively tuned for particular skills, for example to set levels for each individual sensor component, report only on particular motion artefacts, and so on. This is of utility from a range of perspectives, including reducing power consumption at the sensor units, reducing processing overheads at the POD device, and increasing sensitivity to particular crucial motion artefacts (for example by applying a kinematic model which monitors only motions having particular defined characteristics, for example high resolution monitoring of motion in a rowing action, as opposed to motion of a person walking towards a rowing machine).

Figure 12F:
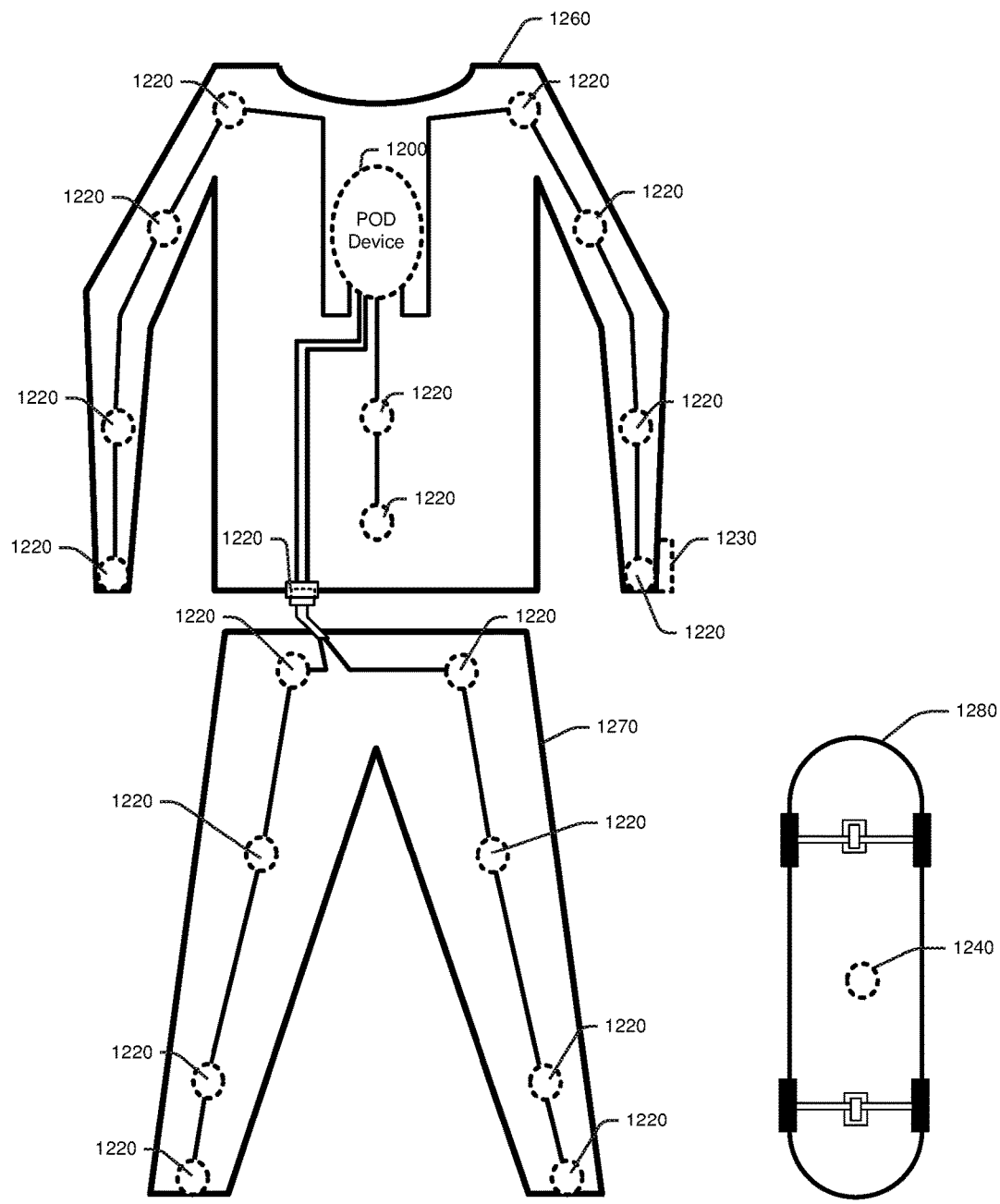
FIG. 12F illustrates a MSU-enabled garment arrangement according to one embodiment, with example connected equipment.

FIG. 12F expands on FIG. 12E by way of illustrating a piece of remote equipment, in this case being a skateboard, which carries a wireless sensor unit 1240. As described above, it is preferable that sensor unit 1240 communicate wirelessly with POD device 1200 via multiple communication pathways, thereby to manage limitations associated with wireless communications. For example, in the illustrated example signals transmitted by sensor unit 1240 are configured to be received by a wireless communications module provided by POD device 1200, and by a wireless communications module provided by wrist control unit 1230 (which transmits the received sensor data via the sensor strand to which it is connected).

Figure 12G:
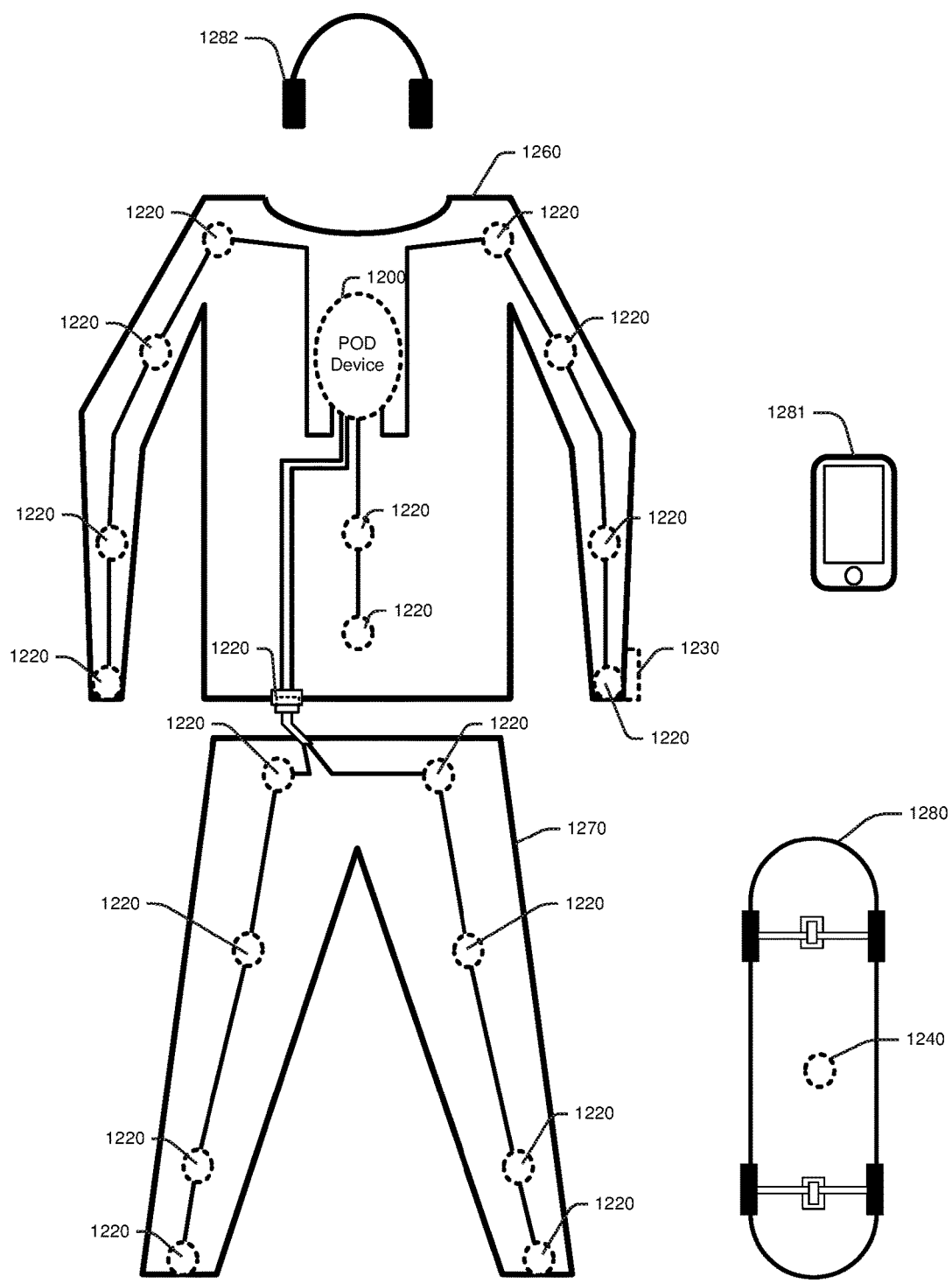
FIG. 12G illustrates a MSU-enabled garment arrangement according to one embodiment, with example connected equipment.

FIG. 12G expands on FIG. 12F by illustrating a mobile device 1281, and a wireless headset 1282.

POD device 1200 communicates with mobile device 1281 (for example a smartphone or tablet, which may operate any of a range of operating systems including iOS, Android, Windows, and so on) thereby to provide to mobile device data configured to enable rendering of content in a user interface display, that content assisting in guiding a user through a skills training program. For example, the content may include video data, text data, images, and so on. In some embodiments POD device 1200 operates as a local web server for the delivery of such content (that is, the mobile device connects to a wireless network advertised by the POD device).

Headset 1282 (which need not be a headset of the design configuration illustrated) enables the user to receive audible feedback and/or instructions from the POD device without a need to carry or refer to a mobile device 1281. This is relevant, for example, in the context of skills where it would be unfeasible or otherwise generally inconvenient to refer to a mobile device, for example whilst rowing, jogging, swimming, snowboarding, and so on. In some embodiments a wired headset may be used, for example via a 3.5 mm headphone jack provided by the garment, which is wire-connected to the POD device.

Figure 12H:
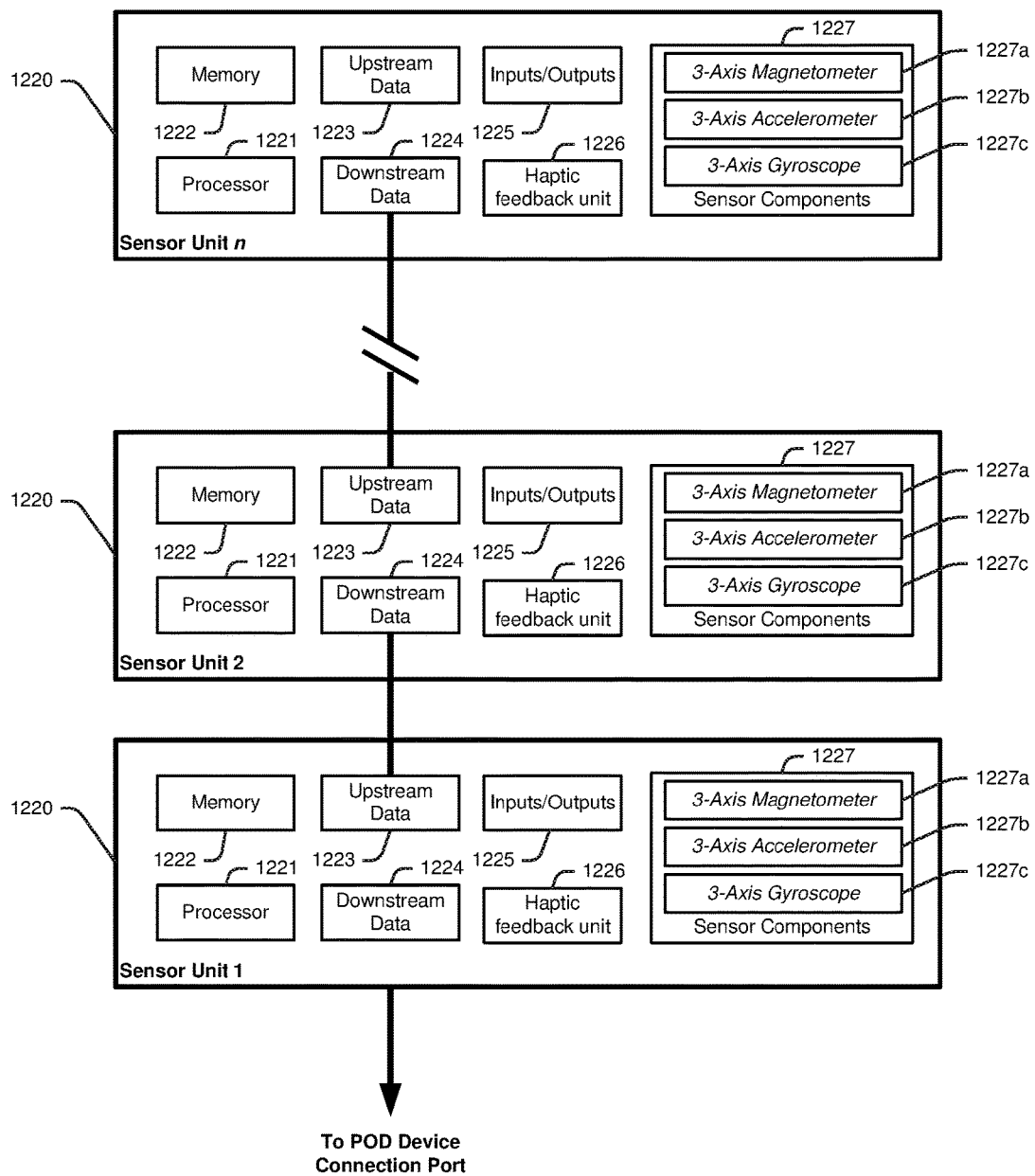
FIG. 12H illustrates MSUs according to one embodiment.

FIG. 12H illustrates a sensor strand according to one embodiment. This includes a plurality of sensor units 1220. Each sensor unit includes a processor 1221 coupled to memory 1222. Upstream and downstream data connections 1223 and 1224 are provided (these may in some embodiments be functionally distinguished based on install orientation). Inputs/outputs 1225 may be provided, such as lights and/or a power/reset button. The illustrated embodiment includes a haptic feedback unit 1226, which may be used to assist in providing feedback to a user (for example activating haptic feedback on a right arm sensor unit corresponding with an instruction to do something with the user's right arm). The illustrated sensor components 1227 are a 3-axis magnetometer 1227a, a 3-axis accelerometer 1227b, and a 3-axis gyroscope 1227c.

Figure 12I:
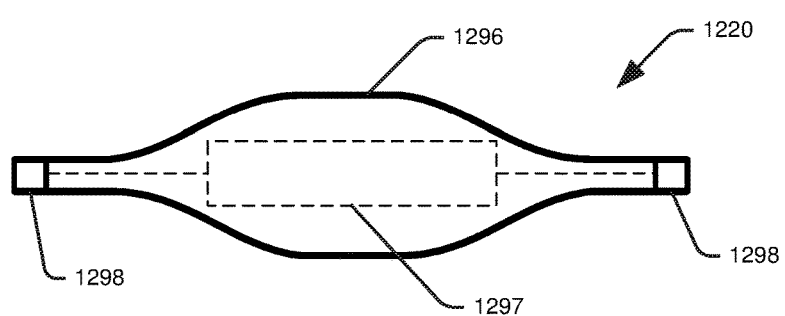
FIG. 12I illustrates a MSU and housing according to one embodiment.

FIG. 12I illustrates an exemplary sensor unit 1220, showing a housing 1296 according to one embodiment. This housing is formed of plastic material, and encloses, in a watertight manner, a circuit board 1297 which provides components illustrated in FIG. 12H. Connectors 1298 enable connection to a sensor strand provided by a garment.

Configuration of MSUs and MSU-Enabled Garments: Overview

Identification of ODCs in end-user equipment in some cases requires: (i) knowledge of the actual positions of MSUs on a given user; and (ii) knowledge of the relative positioning of the MSUs. There are challenges in meaningfully combining data from multiple MSUs, as each MSU conventionally provide motion data with respect to their own frames of reference.

Various embodiments described above make use of data derived from a set of sensor units thereby to enable analysis of a physical performance. These sensor units are mounted to a user's body, for example by way of wearable garments that are configured to carry the multiple sensor units. This section, and those which follow, describe exemplary methodologies that are in some embodiments for configuration of sensor units thereby to enable analysis of movements, such as human body movements, based on data derived from the sensors.

By way of background, a known and popular approach for collecting data representative of a physical performance is to use optical motion capture techniques. For example, such techniques position optically markers observable at various locations on a user's body, and using video capture techniques to derive data representative of location and movement of the markers. The analysis typically uses a virtually constructed body model (for example a complete skeleton, a facial representation, or the like), and translates location and movement of the markers to the virtually constructed body model. In some prior art examples, a computer system is able to recreate, substantially in real time, the precise movements of a physical human user via a virtual body model defined in a computer system. For example, such technology is provided by motion capture technology organisation Vicon.

Motion capture techniques are limited in their utility given that they generally require both: (i) a user to have markers positioned at various locations on their body; and (ii) capture of user performance using one or more camera devices. Although some technologies (for example those making use of depth sensing cameras) are able to reduce reliance on the need for visual markers, motion capture techniques are nevertheless inherently limited by a need for a performance to occur in a location where it is able to be captured by one or more camera devices.

Embodiments described herein make use of motion sensor units thereby to overcome limitations associated with motion capture techniques. Motion sensor units (also referred to as Inertial Measurement Units, or IMUs), for example motion sensor units including one or more accelerometers, one or more gyroscopes, and one or more magnetometers, are able to inherently provide data representative of their own movements. Such sensor units measure and report parameters including velocity, orientation, and gravitational forces.

The use of motion sensor units presents a range of challenges by comparison with motion capture technologies. For instance, technical challenge arise when using multiple motion sensors for at least the following reasons:

Each sensor unit provides data based on its own local frame of reference. In this regard, each sensor inherently provides data as though it defines in essence the centre of its own universe. This differs from motion capture, where a capture device is inherently able to analysis each marker relative to a common frame of reference.

Each sensor unit cannot know precisely where on a limb it is located. Although a sensor garment may define approximate locations, individual users will have different body attributes, which will affect precise positioning. This differs from motion capture techniques where markers are typically positioned with high accuracy.

All sensors act completely independently, as if they were placed in an electronic "bowl of soup", with no bones/limbs connecting them. That is, the sensors' respective data outputs are independent of relative positioning on any sort of virtual body, unlike markers used in motion capture.

Technology and methodologies described below enable processing of sensor unit data thereby to provide a common body-wide frame of reference. For example, this may be achieved by either or both of: (i) defining transformations configured to transform motion data for sensor units SU, to SU, to a common frame of reference; and (ii) determining a skeletal relationship between sensor units SU, to SU,. It will be appreciated that in many cases these are inextricably linked: the transformations to a common frame of reference are what enable determination of skeletal relationships.

In some embodiments, processing of sensor data leads to defining data representative of a virtual skeletal body model. This, in effect, enables data collected from a motion sensor suit arrangement to provide for similar forms of analysis as are available via conventional motion capture (which also provides data representative of a virtual skeletal body model).

Processing techniques described in PCT/AU2016/000020 may be used. In overview, these find application in at least the following contexts:

- Assembling a skeletal model that is suitable for comparison with a model provided via defined motion capture technology. For example, both motion capture data and sensor-derived data may be collected during an analysis phase, thereby to validate whether a skeletal model data, derived from processing of motion sensor data, matches a corresponding skeletal model derived from motion capture technology. This is applicable in the context of a process for objectively defining skills (as described above), or more generally in the context of testing and validating data sensor data processing methods.
- Automated "non-pose specific" configuration of a worn sensor-enabled garment. That is, rather than requiring a user to adopt one or more predefined configuration poses for the purpose of sensor configuration, processing techniques described below allow transformation of each respective sensors' data to a common frame of reference (for example by assembling a skeletal model) by processing sensor data resulting from substantially any motion. That is, the approaches below require fairly generic "motion", for the purpose of comparing motion of one sensor relative to another. The precise nature of that motion is of limited significance.
- Enabling accurate monitoring of a physical performance of a skill (for example in the context of skill training and feedback). For example, this may include monitoring for observable data conditions in sensor data (which are representative of performance affecting factors, as described above).

Additional detail is provided in PCT/AU2016/000020.

Exemplary Challenge Enablement Methodologies

Various exemplary computer implemented methods are discussed below, thereby to provide specific examples of how technology described herein is implemented in practice in the context of challenge enablement. It should be appreciated that further embodiments include variations to these methods, including re-ordering of steps, adding further steps, removing certain steps, and/or implementing steps in manners other than those specifically described.

Figure 4A:
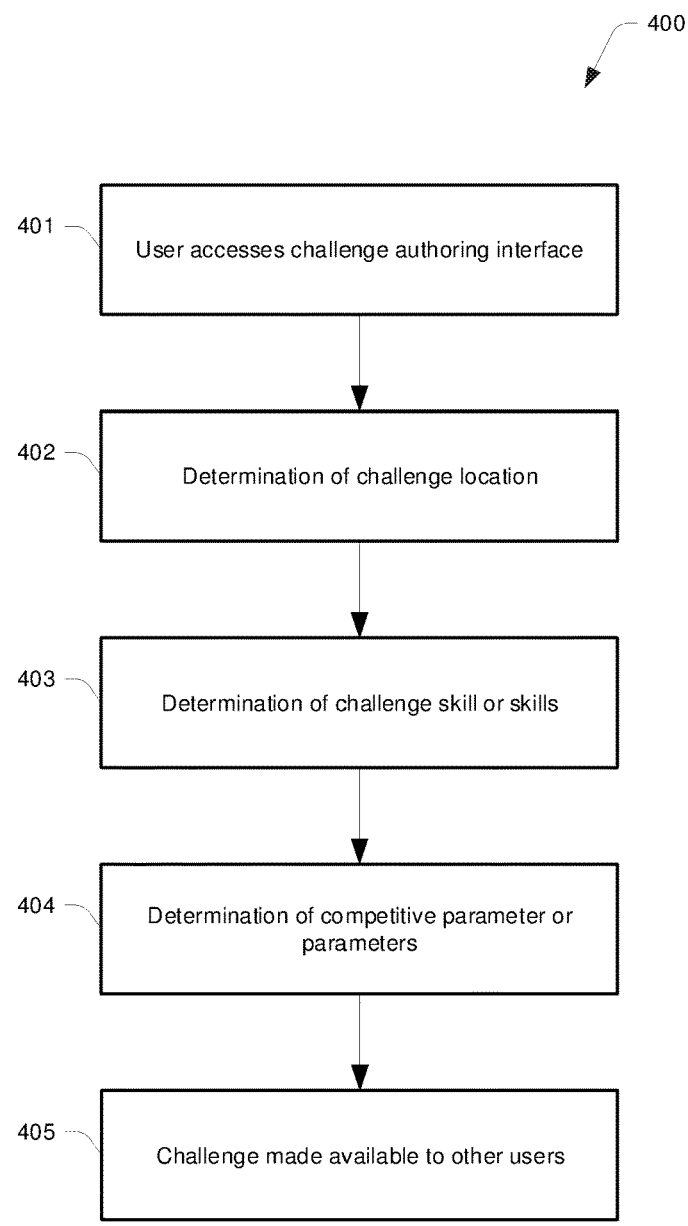
FIG. 4A illustrates a challenge enablement method according to one embodiment.

FIG. 4A illustrates a method 400 according to one embodiment. Method 400 is a method for operating a challenge authoring interface.

Functional block 401 represents a process whereby a specific user accesses a challenge authoring interface. For example, the user operates a computing device (such as a PC, notebook, laptop, gaming console, tablet or smartphone) thereby to render on-screen a user interface that enables interaction between the authoring interface and the user. Preferably the authoring interface itself is in whole or in part cloud-hosted (that is, substantive portions of code and processing operations relating to the authoring of competitive activities are provided via a server device). The user interface is in some embodiments rendered in a web browser application (by way of code downloaded from a web server), and in other embodiments rendered via a proprietary software application stored in local memory. In any case, accessing the challenge authoring interface includes the user providing login credentials (in some cases these are stored locally allowing for automated login), such that the user is able to be uniquely identified.

In some embodiments a challenge location is not defined, enabling participation at any location. In some embodiments there are additionally (or alternately) timing parameters associated with a challenge (for example a defined time period for which the challenge is to be made available).

Functional block 402 represents a process including determination of a challenge location. Various technologies are available to be used for this process, including:

(i) Geolocation, for example using GPS or the like, of the user's current position. This is particularly relevant where a user authors a challenge using a mobile device (such as a smartphone) whilst at the relevant location.

(ii) Location-specific tokens, such as 2D barcodes, BLE tags, RFID tags, and the like. These are each able to be uniquely associated with a defined location, such that a user of a client device is enabled to read the token and hence identify the location.

(iii) Access to former location data associated with a user. For example, a user defines a challenge from a home location, and accesses data representative of locations at which the user previously performed skills (for example based on geolocation, location-specific tokens, and so on).

(iv) Utilisation of search engines, for example search engines that provide results associated with geographically defined locations.

The degree of specificity at which a user defines a challenge location varies between embodiments.

Functional block 403 represents a process including determination of a challenge skill or skills. For example, in one embodiment a user selects an activity (for example by selection of a sport, such as "soccer", "tennis" or "skateboarding"), and then is presented with skills that are available for inclusion in challenges (for instance based on skills that are able to be identified/analysed using MSD). In some embodiments suggestion modules assist a user, for example by filtering skills based on skills that the relevant user has (i) performed; and/or (ii) demonstrated competency in (for example via participation in training programs). In some cases a challenge is defined to require performance of a single skill, in some cases there are multiple skills. It will be appreciated that, in some embodiments, the determination of a skill or skills enables determination of state engine data that is required at a given activity-participant user's POD device in order participate in an activity.

Functional block 404 represents a process including determination of a challenge competitive parameter or parameters. In some embodiments competitive parameters are filtered based on the skill/skills selected at 404. For example, in some embodiments competitive parameters are able to be set based on attributes of a skill: a given skill is in some cases associated with attributes such as "height", "accuracy", "speed", "power" and so on. In one embodiment, for each selected skill, an activity-author user is enabled to set competitive parameters for each attribute. For instance, a skill, Skill A, may have a "height" attribute, and the user sets competitive parameters based on selectable criteria inducing "no height requirement", "minimum height requirement X" or "compete for maximum height". In some embodiments a user builds competitive parameters by combining multiple parameters using AND operators, or by other similar techniques.

Functional block 405 represents a process including finalisation of the challenge by the activity-author user, at which point the challenge is made available to other users. That is, other users are enabled to identify the challenge, and participate if they wish. In some embodiments an activity-author user is enabled to decide with which other users a given challenge is to be shared, for example to "public", to "friends" or "contacts", or to a specific user or group of users. For example, in a sporting context, a coach is able to define a challenge and share it only with players in that coach's team.

Figure 4B:
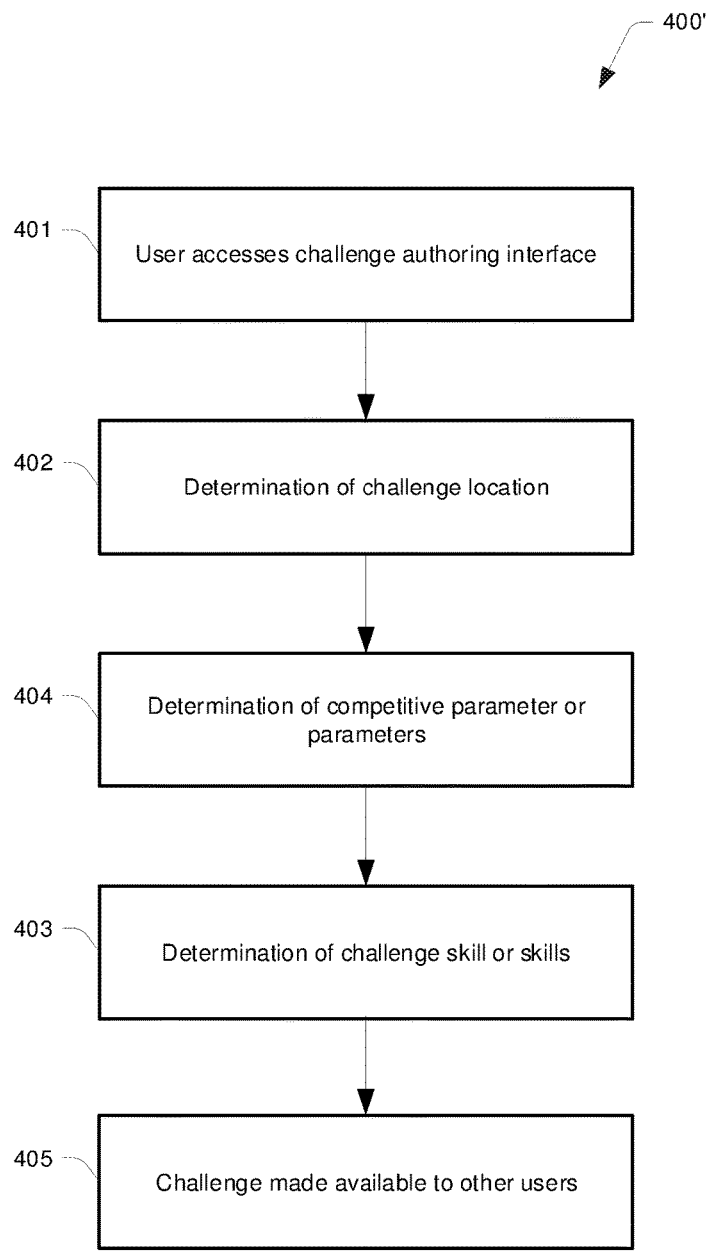
FIG. 4B illustrates a challenge enablement method according to one embodiment.

FIG. 4B illustrates a method 400', which is a variation of method 400. In this instance, functional blocks 403 and 404 are reversed, such that a user first selects one or more competitive parameters, and then selects skills. For example, the user selects a competitive parameter type such as "most in succession", "highest attempt", "longest hold", "fastest time", and then is presented with a filtered set of skills that are appropriate for that competitive parameter. It will be appreciated that in some embodiments a process by which challenge data is defined is iterative between selection of skills and selection of competitive parameters.

Figure 4C:
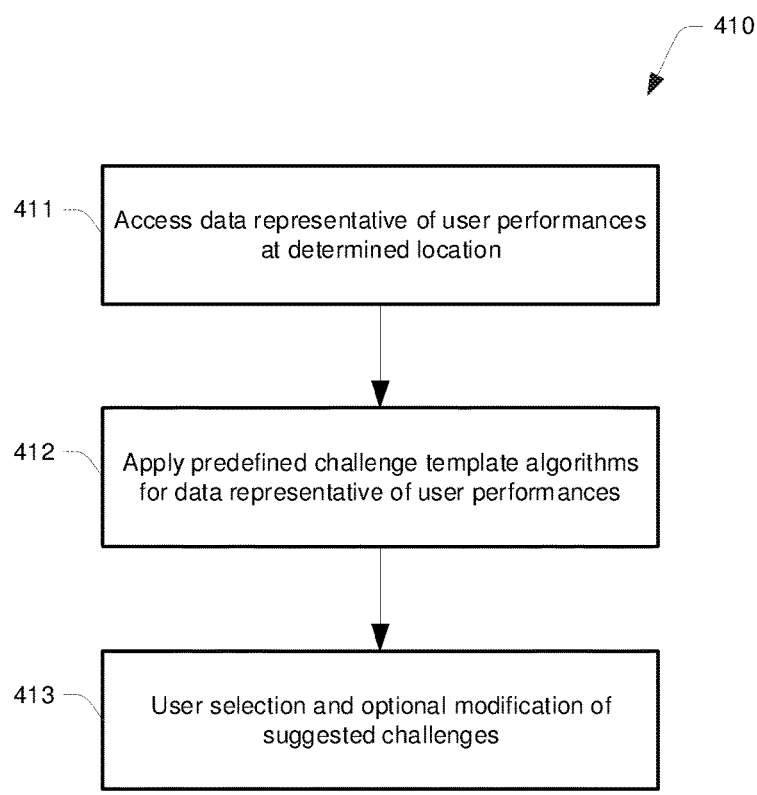
FIG. 4C illustrates a challenge enablement method according to one embodiment.

FIG. 4C illustrates a method 410, being a method enabling intelligent suggestion determination to assist an activity-author user. Functional block 411 represents a process including accessing data representative of user performances at a determined location. In some embodiments, a user previously downloads to their POD device state engine data configured to enable monitoring of a given activity type, which includes a plurality of skills. For example, this may be a "skateboarding monitoring pack", which enables the user's POD device to identify a set of skateboarding skills (for example specific tricks) and attributes of those tricks (e.g. identifying that a user has successfully performed a "kickflip" manoeuvre, and a height measurement for that kickflip manoeuvre). This allows a user to maintain a record of their performances, which are able to be associated with locations, and otherwise subsequently analysed/queried. For example, a user may wish to review their overall results from a session of skateboarding, by reviewing how many tricks were successfully performed, which tricks they were, attributes of those tricks, and so on. Data representative of user performances is preferably stored in a central repository, such as database 120 of FIG. 1.

Functional block 412 represents a process including applying predefined challenge template algorithms in respect of data representative of user performances. For example, challenge templates may be defined on a per-activity basis, or generically. Each template is configured to be associated with one or more specific skills (for example a particular challenge type is defined for a particular skill), or with any skills that have one or more specific attributes (for example a "challenge for highest attempt" is able to be associated with all skills that record a height attribute). The algorithms may be executed in respect of either or both of: (i) skills associated with a predefined challenge location; and (ii) skills associated with a particular activity-author user. For example, in one embodiment a "highest attempt" template algorithm executes in respect of performance data associated with a given user at a given location, Location X, and identifies that a user has performed Skill A, being a skill having a height attribute, at the relevant location, and that the user's height for Skill A is the highest recorded in database 120. The user is informed "you have the highest attempt at Skill A at Location X; would you like to challenge others to beat you?"

Functional block 413 represents a process whereby a user reviews, selects, and optionally modified challenges suggested via the process of block 412. Following that, the challenge is able to be shared with other users (block 405).

Figure 4D:
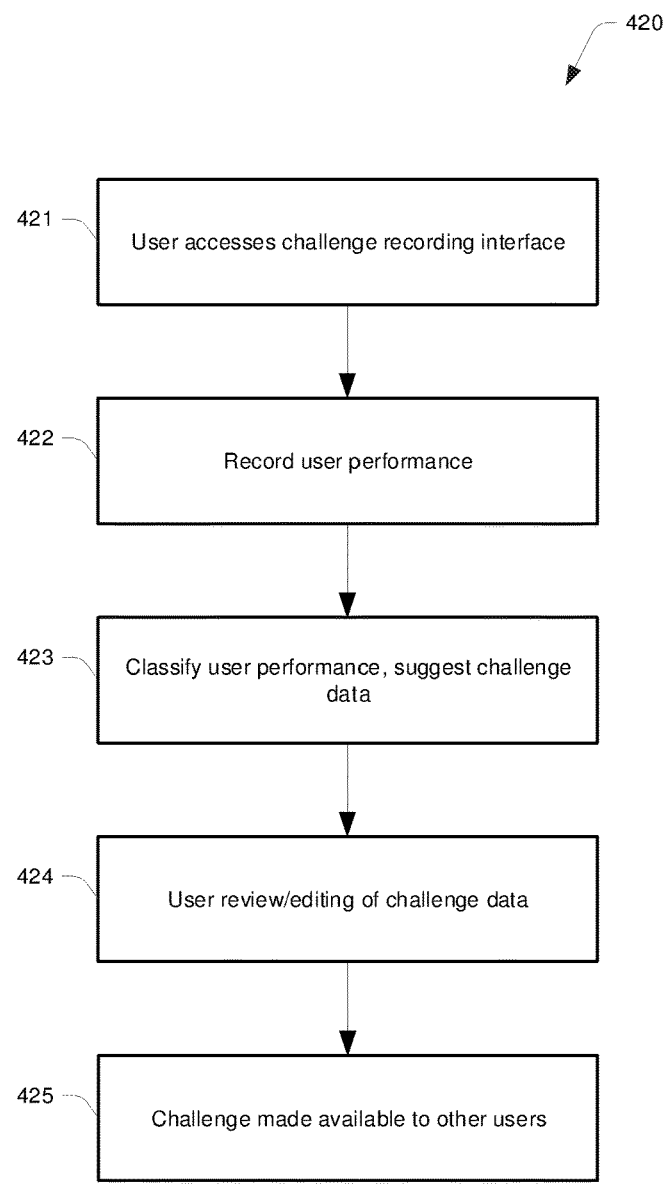
FIG. 4D illustrates a challenge enablement method according to one embodiment.

FIG. 4D illustrates a method 420, which includes functionality for enabling challenge recording functionality. Functional block 421 includes accessing a challenge recording interface, which configures a POD device to record a user performance at 422. For example, the challenge recording interface is in some embodiments accessed using a control device such as a smartphone. The recording at 422 may include recording all or a subset of data collected by sensor units, for example to enable generation of a model (for example kinematic, kinetic or "skelematic" model) that enables subsequent review and/or monitoring (in respect of activity-participant users). Functional block 423 represents a process including classifying the user performance, and suggesting challenge data. For example, attributes such as height, power, and the like may be identified in attribute data. In some embodiments, however, the crux of a recorded performance is derived from specific motion aspects (for example where the recording is of a new skill, such as a yoga pose, a stretch, a skateboarding trick, a parkour manoeuvre, and so on).

Functional block 424 represents a process including enabling user review and/or editing of challenge data for the recorded challenge, before the challenge is made available at 425. The review and/or editing may include review of a three-dimensional graphical model showing what was recorded, and trimming/clipping a time-based portion of the recording which defines the desired skill.

Figure 4E:
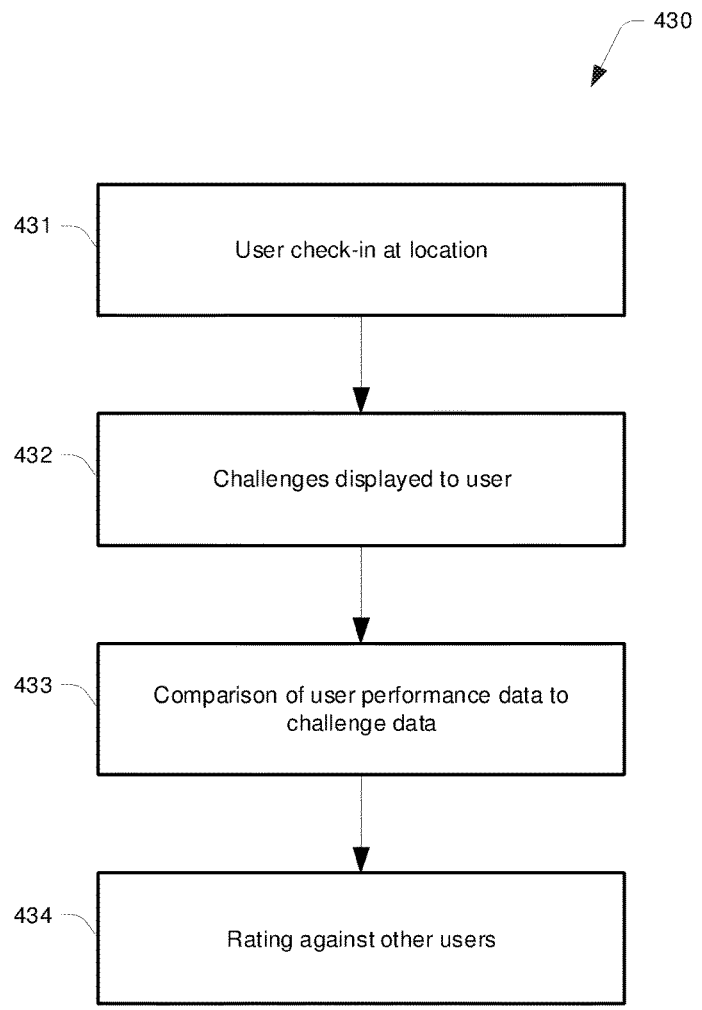
FIG. 4E illustrates a challenge enablement method according to one embodiment.

FIG. 4E illustrates a method 430 for enabling a user to participate in one or more challenges. Functional block 431 represents a user check-in at a location. Based on this check in, the user is enabled to view available challenges. In some embodiments the user positively selects one or more challenges in which to participate, this enables the user's POD device to monitor for the relevant skill or skills (and/or attributes thereof). In some embodiments this triggers a download process in respect of state engine data (and other data, such as sensor configuration data) that is required at the user's local hardware (e.g. on a POD device) device in order to identify skills and/or attributes for a selected challenge. In other embodiments challenges are only displayed as being selectable in the case that the necessary state engine data is already available at the user's POD device.

Functional block 433 represents a process including comparison of user performance data to challenge data. For example, this may include recording data representative of skills performed, and attributes thereof, based on requirements of a given challenge data set. This enables, at 434, rating of the user against other users.

Figure 8:
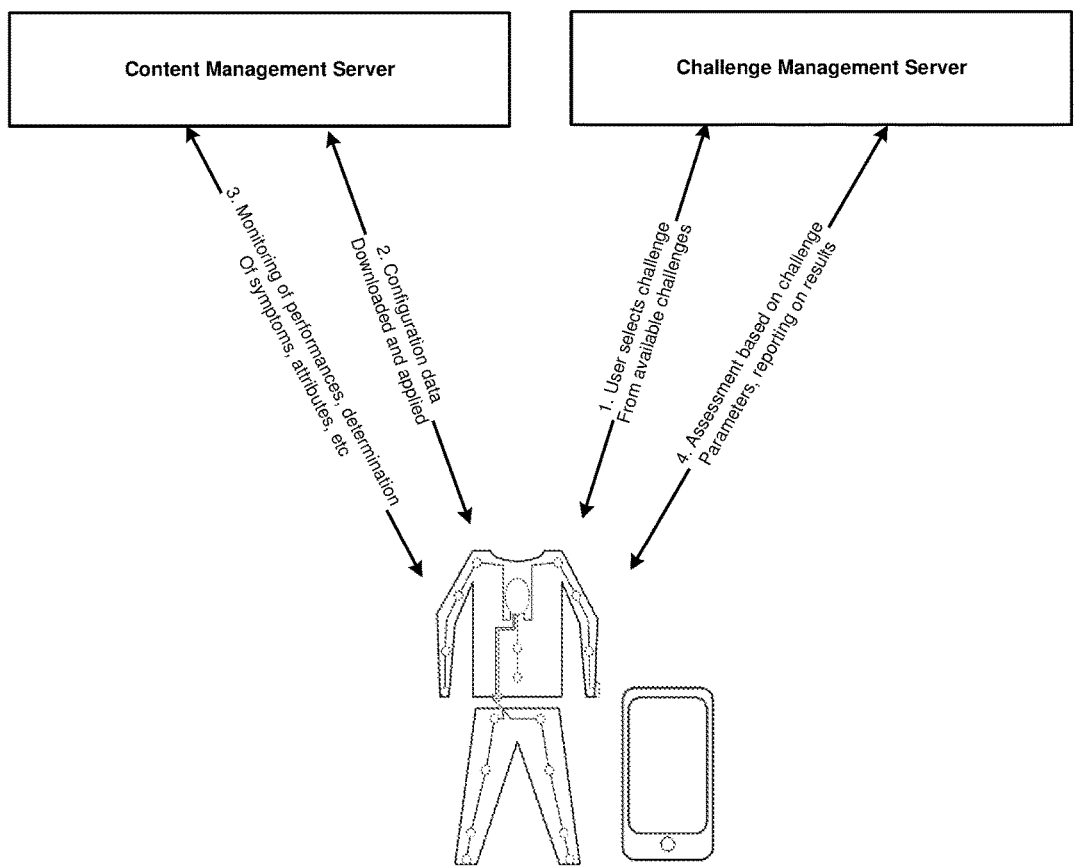
FIG. 8 schematically illustrates an exemplary implementation according to one embodiment.

FIG. 8 provides an alternate schematic representation of a challenge enablement framework, showing an example use case. This shows a content management server, a challenge management server, and end user hardware. The content management server and challenge management server are shown as separate components for the sake of illustration only, and functionalities of these two servers are in some embodiments provided by a single server, or by a larger number of servers.

At a functional level:
- The content management server makes available skill-specific configuration data, including state engine data and sensor configuration data. In some embodiments the content management server is additionally configured to perform at least a portion of processing of data derived from MSUs, thereby to identify skill performance attributes. The content management server is optionally also responsible for delivery of a range of additional content unrelated to challenges, for example skills training content.
- The challenge management server maintains data representative of defined challenges, and manages user participation in those challenges.
- The end-user hardware includes a MSU-enabled garment and a user interface device (such as a smartphone).

FIG. 8 shows an example use case process by which a user participates in a challenge. As indicated by step 1, a user selects a challenge from a list of available challenges. The list is rendered at the user's user interface device based on data provided by the challenge management server (optionally via the content management server). Having selected a challenge, the user's hardware (for example the MSU-enabled garment) is configured such that the MSUs deliver data that enables analysis of physical performance events relevant to the challenge. This, in the example of FIG. 8, includes downloading configuration data (including sensor configuration data and state engine data for one or more skills that form part of the selected challenge. For example, the challenge might be a "biggest punt kick" challenge, in which case configuration data is downloaded (step 2) and applied thereby to enable: (i) analysis to identify that a "punt kick" has been performed; and (ii) analysis to determine a power output measure associated with the performed punt kick (for example based on variations in acceleration of one or more MSUs; for instance using one or more symptoms of the performed skill. Monitoring is designated by step 3; as illustrated there is server-side involvement in monitoring (for example MSD-derived data is transmitted for server-side processing). Based on the monitoring, values for challenge parameters are identified, enabling assessment of a user challenge attempt, and reporting on results. Data representing determined values for the challenge parameters are in some cases transmitted directly from the end-user hardware to the challenge management server; in other cases this data is routed via the content management server.

Conclusions and Interpretation

It will be appreciated that technology described above provides advances across a range of fields, delivery of gamified content. For example, by utilising predefined processing techniques that enable skill performance identification from MSU-enabled garments (and optionally other forms of PSUs), video data is able to be automatically categorised in a rich and effective manner.

Unless specifically stated otherwise, as apparent from the following discussions, it is appreciated that throughout the specification discussions utilizing terms such as "processing," "computing," "calculating," "determining", analysing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a user machine in server-user network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while diagrams only show a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that is for execution on one or more processors, e.g., one or more processors that are part of web server arrangement. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause the processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media; a medium bearing a propagated signal detectable by at least one processor of one or more processors and representing a set of instructions that, when executed, implement a method; and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A method for providing challenges, including:
   providing an authoring interface that enables an author to define a challenge for participants including the author;
   via the authoring interface, receiving a challenge data set for the challenge, wherein the challenge data set includes:
   (i) data representative of a challenge location;
   (ii) data representative of one or more challenge skills, wherein each of the one or more challenge skills are selected from a repository of challenge skills that are configured to be identified via motion sensor units worn by each of the participants; and
   (iii) data representative of one or more competitive parameters for one or more attributes of the one or more challenge skills;
   making the challenge available to the participants, comprising, for each of the participants:
   receiving data representative of a participant location;
   based on the participant location and the challenge location, identifying the challenge among the challenges and providing a participant interface that enables a selection of the challenge;
   via the participant interface, receiving the selection of the challenge; and
   providing configuration data for the motion sensor units worn by each participant to enable monitoring performance of the one or more challenge skills performed by each participant;
   receiving performance data from said monitoring the performance of the one or more challenge skills performed by each participant;
   based on the performance data of each participant, rating the participants; and
   via the participant interface, reporting the participants' ratings.

2. A method according to claim 1, wherein the motion sensor units comprise part of a garment.

3. A method according to claim 1, further comprising suggesting the challenge based on past performance data of skills performed by the author at the challenge location.

4. A method according to claim 3, further comprising:
   processing the past performance data of the skills performed by the author at the challenge location; and
   based on said processing, suggesting one or more values for the one or more competitive parameters.

5. A method according to claim 4, wherein said suggesting the challenge is based on (i) a skill completed by the author and (ii) for which the author is a current leader.

6. A method according to claim 1, wherein the challenge location represents a region at which the challenge is to be completed.

7. A method according to claim 1, wherein the one or more competitive parameters include a count of how many times a particular challenge skill is performed in succession.

8. A method according to claim 1, wherein the one or more competitive parameters include a count of how many times a particular challenge skill is performed relative to a defined time period.

9. A method according to claim 1, wherein the one or more competitive parameters include a count of how many unique challenge skills are performed in succession.

10. A method according to claim 1, wherein the one or more competitive parameters include a count of how many unique challenge skills are performed relative to a defined time period.

11. A method according to claim 1, wherein the one or more competitive parameters include a time period to perform a defined set of challenge skills.

12. A method according to claim 11, wherein the one or more challenge skills include multiple instances of a single challenge skill.

13. A method according to claim 1, wherein the one or more competitive parameters include a competitive parameter affected by a value derived from the one or more performance attributes for a given skill.

14. A method according to claim 13, wherein the one or more performance attributes are defined based on one or more of: performance of the skill relative to defined optimal performance; one or more motion-based attributes observed in the performance of the skill; a skill performance height attribute; a skill performance distance attribute; a skill performance power attribute; a skill performance speed attribute; and a skill performance duration attribute.

15. A method according to claim 1, wherein the authoring interface is available in a local mode, whereby the authoring interface is presented on a local user interface device, and the authoring interface accesses skill performance data associated with the author from a local storage repository.

16. A method according to claim 15 wherein the authoring interface is additionally available in an online mode, whereby the authoring interface accesses the skill performance data associated with the author from a central storage repository.

17. A method according to claim 1, wherein said providing the configuration data for the motion sensor units worn by each participant to enable monitoring of the one or more challenge skills includes configuring a device local to the participant to monitor performance of the one or more challenge skills relative to the one or more competitive parameters in an offline mode.

18. A computer system configured to perform a method according to claim 1.

19. A method for operating end-user hardware including one or more motion sensor units (MSUs), the method including:
   receiving an authoring interface from one or more servers, the authoring interface enabling a user to define a challenge for participants including the user, wherein the challenge is to be attempted by the user with the end-user hardware including the one or more MSUs,
   via the authoring interface, providing a challenge data set for the challenge, the challenge data set includes data representative of:
   (i) a challenge location;
   (ii) one or more challenge skills; and
   (iii) one or more competitive parameters for one or more attributes of the one or more challenge skills;
   via the authoring interface, sending the challenge to the one or more servers;
   sending a participant location of the user to the one or more servers;

receiving a participant interface from the one or more servers, the participant interface enabling the user to select the challenge;

via the participant interface, selecting the challenge and sending the selection to the one or more servers;

enabling the end-user hardware including the one or more MSUs to participate in the challenge, comprising:
  (i) causing the end-user hardware to apply configuration data for the one or more challenge skills; and
  (ii) sending performance data derived from the one or more MSUs or an assessment of the performance data to the one or more servers; and via the participant interface, receiving a rating of the user among the participants of the challenge.

20. A method according to claim 19, wherein the end-user hardware includes a garment comprising the one or more MSUs.

21. A method according to claim 19, wherein the challenge location represents a region at which the challenge is to be completed.

22. A method according to claim 19, wherein the one or more competitive parameters include a count of how many times a particular challenge skill is performed in succession, a count of how many times a particular challenge skill is performed relative to a defined time period, a count of how many unique challenge skills are performed in succession, a count of how many unique challenge skills are performed relative to a defined time period, or a time period to perform a defined set of challenge skills.

23. A method according to claim 22, wherein the one or more challenge skills include multiple instances of a single challenge skill.

24. A method according to claim 19, wherein the one or more competitive parameters include a competitive parameter affected by a value derived from the one or more performance attributes for a given skill.

25. A method according to claim 24, wherein the one or more performance attributes are defined based on one or more of: performance of the skill relative to defined optimal performance; one or more motion-based attributes observed in the performance of the skill; a skill performance height attribute; a skill performance distance attribute; a skill performance power attribute; a skill performance speed attribute; and a skill performance duration attribute.

* * * * *